(12) United States Patent
Broeckling et al.

(10) Patent No.: US 8,809,627 B2
(45) Date of Patent: Aug. 19, 2014

(54) PLANT ISOFLAVONE AND ISOFLAVANONE O-METHYLTRANSFERASE GENES

(75) Inventors: Bettina E. Broeckling, Fort Collins, CO (US); Chang-Jun Liu, Rocky Point, NY (US); Richard A. Dixon, Ardmore, OK (US)

(73) Assignee: The Samuel Roberts Noble Foundation, Inc., Ardmore, OK (US)

( * ) Notice: Subject to any disclaimer, the term of this patent is extended or adjusted under 35 U.S.C. 154(b) by 1075 days.

(21) Appl. No.: 11/840,032

(22) Filed: Aug. 16, 2007

(65) Prior Publication Data

US 2008/0317880 A1    Dec. 25, 2008

Related U.S. Application Data

(60) Provisional application No. 60/838,072, filed on Aug. 16, 2006.

(51) Int. Cl.
| | |
|---|---|
| *A01H 5/00* | (2006.01) |
| *A01H 1/00* | (2006.01) |
| *C12N 5/14* | (2006.01) |
| *C12N 15/82* | (2006.01) |
| *C12N 15/63* | (2006.01) |
| *C07H 21/04* | (2006.01) |

(52) U.S. Cl.
USPC ........ 800/295; 800/278; 800/282; 435/320.1; 435/419; 435/468; 536/23.2; 536/23.6

(58) Field of Classification Search
USPC ....................................................... 800/282
See application file for complete search history.

(56) References Cited

U.S. PATENT DOCUMENTS

| | | | | |
|---|---|---|---|---|
| 6,878,859 B1 * | 4/2005 | Dixon et al. | ................... | 800/279 |
| 2005/0150010 A1 | 7/2005 | Dixon et al. | ................... | 800/278 |

FOREIGN PATENT DOCUMENTS

WO    WO 00/71736    11/2000

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Wells, (Biochemistry 29:8509-8517, 1990).*
Gang et al. (The Plant Cell, 14:505-519, 2002).*
Schroder et al. (Phytochemistry, 59:1-8, 2002.*
Lin et al. (NCBI, GenBank Sequence Accession No. AC146549; Published Mar. 18, 2006).*
Lin et al. (GenBank Accession No. AC146549.1, accessed Sep. 23, 2013, published Aug. 30, 2003).*
Akashi et al., "cDNA cloning and biochemical characterization of S-adenosyl-L-methionine, 2,7,4'-trihydroxyisoflavanone 4'-O-methyltransferase, a critical enzyme of the legume isoflavonoid phytoalexin pathway," *Plant Cell Physiol.*, 44(2):103-112, 2003.
Asamizu et al., "Generation of 7137 non-redundant expressed sequence tags from a legume, *Lotus japonicus*," *DNA Research*, 7:127-130, 2000.
Ferrer et al., "Crystal structures of alfalfa caffeoyl coenzyme A 3-O-methyltransferase," *Plant Physiol.*, 137:1009-1017, 2005.
Frick et al., "Combinatorial biochemistry in plants: the case of O-methyltransferases," *Phytochemistry*, 56:1-4, 2001.
GenBank Accession No. AB091684, dated Mar. 4, 2003.
GenBank Accession No. AB091685, dated Mar. 4, 2003.
GenBank Accession No. AB091686, dated Apr. 20, 2006.
GenBank Accession No. AC146549, dated Aug. 23, 2007.
GenBank Accession No. AW329787, dated Jan. 28, 2000.
GenBank Accession No. AW687093, dated Jun. 14, 2000.
GenBank Accession No. AY127569, dated Dec. 14, 2002.
GenBank Accession No. AY343490, dated May 5, 2004.
GenBank Accession No. AY942158, dated Feb. 2, 2007.
GenBank Accession No. AY942159, dated Jun. 1, 2006.
GenBank Accession No. BE320503, dated Dec. 20, 2000.
GenBank Accession No. BE320546, dated Dec. 20, 2000.
GenBank Accession No. BF637366, dated Dec. 19, 2000.
GenBank Accession No. BG448331, dated Mar. 16, 2001.
GenBank Accession No. CG924089, dataed Dec. 12, 2003.
GenBank Accession No. DQ419910, dated Oct. 27, 2006.
GenBank Accession No. DQ419911, dated Oct. 27, 2006.
GenBank Accession No. DQ419912, dated Oct. 27, 2006.
GenBank Accession No. DQ419913, dated Oct. 27, 2006.
GenBank Accession No. DQ419914, dated Oct. 27, 2006.
GenBank Accession No. DQ419915, dated Oct. 27, 2006.
GenBank Accession No. Q29U70, dated Nov. 28, 2006.
GenBank Accession No. U69554, dated Oct. 29, 1997.
GenBank Accession No. U97125, dated Feb. 25, 1998.
GenBank Accession No. X77467, dated Apr. 18, 2005.
He et al., "Affinity chromatography, substrate/product specificity, and amino acid seq2uence analysis of an isoflavone o-methyltransferase from alfalfa (*Medicago sativa* L.)," *Archives of Biochemistry and Biophysics*, 336(1):121-129, 1996.
He et al., "Stress response in alfalfa (*Medicago sativa* L). XXII. cDNA cloning and characterization of an elicitor-inducible 7-O-methyltransferase," *Plant Mol. Biol.*, 36:43-54, 1998.
Joshi et al., "Conserved sequence motifs in plant S-adenosyl-L-methionine-dependent methyltransferases," *Plant Mol. Biol.*, 37:663-667, 1998.
Kim et al., "Regiospecific methylation of naringenin to ponciretin by soybean O-methyltransferase expressed in *Escherichia coli*," *J. of Biotechnology*, 119:155-162, 2005.
Liu et al., "Structural basis for dual functionality of isoflavonoid O-methyltransferases in the evolution of plant defense responses," *The Plant Cell*, 18:3656-3669, 2006.

(Continued)

*Primary Examiner* — Vinod Kumar
*Assistant Examiner* — Rebecca Coobs
(74) *Attorney, Agent, or Firm* — Dentons US LLP

(57) ABSTRACT

The invention provides enzymes that encode O-methyltransferases (OMTs) from *Medicago truncatula* that allow modification to plant (iso)flavonoid biosynthetic pathways. In certain aspects of the invention, the genes encoding these enzymes are provided. The invention therefore allows the modification of plants for isoflavonoid content. Transgenic plants comprising such enzymes are also provided, as well as methods for improving disease resistance in plants. Methods for producing food and nutraceuticals, and the resulting compositions, are also provided.

19 Claims, 41 Drawing Sheets

(56) References Cited

OTHER PUBLICATIONS

Noel et al., "Structural, functional, and evolutionary basis for methylation of small plant molecules," In: Recent Advances in Phytochemistry, vol. 37, Romeo ed., Oxford, Elseiver Science Ltd., pp. 37-58, 2003.

Schroder et al., "Flavonoid methylation: a novel 4'-O-methyltransferase from *Catharanthus roseus*, and evidence that partially methylated flavanones are substrates of four different flavonoid dioxygenases," *Phytochemistry*, 65:1085-1094, 2004.

Suzuki et al., "Methyl jasmonate and yeast elicitor induced differential transcriptional and metabolic re-programming in cell suspension cultures of the model legume *Medicago truncatula*," *Planta*, 220(5):696-707, 2005.

Zubieta et al., "Structural basis for the modulation of lignin monomer methylation by caffeic acid/5-hydroxyferulic acid 3/5-O-methyltransferase," *The Plant Cell*, 14:1265-1277, 2002.

Zubieta et al., "Structures of two natural product methyltransferases reveal the basis for substrate specificity in plant O-methyltransferases," *Nature Structural Biology*, 8:271-279, 2001.

Zubieta et al., PDB 1fp2, dated Aug. 29, 2000.

* cited by examiner

*(a)* daidzein → isoformononetin

*(b)*

2,7,4'-trihydroxyisoflavanone → 2,7-dihydroxy-4'methoxyisoflavanone → formononetin (b)

| | | | |
|---|---|---|---|
| MtIOMT1 | TYVGGDMFTSIPNADAVLLK | (588) | YILHNWTDKDCTRILKKCKE |
| MtIOMT2 | NFVGGDMFKSVPSADAVLLK | (800) | WVLHDWNDELCLKILKNCKE |
| MtIOMT3 | TYVGGDMFISVPKADAVLLK | (626) | AVLHDWTDKDCIKILKKCKE |

7,3',4'-trihydroxyisoflavone liquiritigenin naringenin 7,4'-dihydroxyflavone (g)

(h)

(i)

(j)

(k)

(l)

(m)

PLANT ISOFLAVONE AND ISOFLAVANONE O-METHYLTRANSFERASE GENES

This application claims the priority of U.S. provisional application Ser. No. 60/838,072, filed Aug. 16, 2006, the entire disclosure of which is incorporated herein by reference.

The Government may own rights in the invention pursuant to grant from the National Science Foundation Grant No. 0236027 and Grant No. DBI 010973, and a Laboratory Directed Research and Development Award (LDRD) at Brookhaven National Laboratory under contract with the U.S. Department of Energy.

BACKGROUND OF THE INVENTION

1. Field of the Invention

The present invention relates generally to the field of molecular biology. More specifically, the invention relates to methods and compositions for modifying plant flavonoid metabolism.

2. Description of the Related Art

Isoflavonoids represent a class of bioactive plant natural products with important implications for plant, animal and human health (Dixon and Steele, 1999). Over 850 isoflavonoid aglycones have been identified and much of this molecular diversity is generated through the biosynthetic modification of core isoflavonoid chemical scaffolds (Harborne, 1994). The majority of naturally occurring isoflavonoids are O-methylated at one or more positions, and over 80% of the reported isoflavonoids in the forage legume alfalfa (*Medicago sativa*) contain at least one methoxyl group (Bisby et al., 1994). Methylation alters the chemical reactivity and biosynthetic fate of hydroxyl groups, modulates solubility and intracellular localization (Ibrahim et al., 1987), and re-directs biosynthetic intermediates down specific branches of complex metabolic grids (Maxwell et al., 1993).

Enzymatic O-methylation is catalyzed by O-methyltransferases (OMTs), which catalyze transfer of a methyl group from S-adenosyl-L-methionine (SAM) to a hydroxyl moiety of an acceptor molecule. Two distinct groups of small molecule OMTs can be distinguished from plants (Joshi and Chiang, 1998). Group I OMTs are 38-43 kDa proteins which do not require a metal ion for activity, and which methylate a variety of acceptors including phenylpropanoids, flavonoids, alkaloids, and coumarins (Noel et al., 2003). Group II OMTs are of lower MW (23-27 kDa), and are $Mg^{2+}$-dependent enzymes represented by caffeoyl-CoA 3-OMT. Substrate specificities of OMTs can not be accurately predicted on the basis of sequence similarity alone (Schroder et al., 2002), and in some cases a single amino acid change can alter substrate specificity (Frick and Kutchan, 1999; Gang et al., 2002). Elucidation of the crystal structures of caffeoyl CoA 3-OMT and three different group I OMTs from alfalfa (Zubieta et al., 2001; Zubieta et al., 2002; Ferrer et al., 2005) has now made it possible to explore the structural basis of OMT substrate specificity by homology-based modeling (Hoffmann et al., 2001; Gang et al., 2002; Komblatt et al., 2004; Yang et al., 2004).

Isoflavonoid OMTs catalyze the biosynthesis of natural chemicals that are important for disease resistance in legumes. 6a-Hydroxymaackiain 3-OMT in pea (*Pisum sativum*) (PsHMM) methylates the relatively nontoxic isoflavonoid-derived compound 6a-hydroxymaackiain to produce the potent antimicrobial chemical pisatin, thereby constituting an essential step in phytoalexin biosynthesis (VanEtten et al., 1982; Preisig et al., 1989).

In addition to PsHMM, two other isoflavonoid O-methyltransferases have been characterized at the molecular level. *Medicago sativa* isoflavone 7-OMT (MsI7OMT) catalyzes A-ring 7-O-methylation of isoflavones such as daidzein in vitro (FIG. 1), and has been studied both biochemically and structurally (He and Dixon, 1996; He et al., 1998; Zubieta et al., 2001; U.S. Patent Publication 20050150010). Although 7-O-methylated isoflavones such as isoformononetin (7-O-methyl-daidzein) are uncommon in legumes, the induction of I7OMT transcripts and observable enzymatic activity after elicitation or fungal infection in alfalfa suggested a role for this enzyme in the phytoalexin response (Edwards and Dixon, 1991; Akashi et al., 2000; He and Dixon, 2000). Paradoxically, over-expression of MsI7OMT in alfalfa did not produce isoformononetin, but led to greater accumulation of the 4'-O-methylated isoflavonoids formononetin and medicarpin in elicited leaves, and enhanced resistance to the fungal leaf pathogen *Phoma medicaginis* (He and Dixon, 2000). I7OMT activity is not restricted to alfalfa, and the enzyme has been recently cloned from licorice (*Glycyrrhiza echinata*) (Akashi et al., 2003). In addition to their role in plant defense responses, isoflavones may also demonstrate medical or nutraceutical uses.

The most common site of methylation of isoflavonoids is at the 4'-position of the B-ring (isoflavone numbering), but identification of an IOMT with 4'-specificity eluded efforts until recently (Wengenmayer et al., 1974; Edwards and Dixon, 1991; He and Dixon, 1996; Akashi et al., 2003). It now appears that 4'-O-methylation in isoflavonoid biosynthesis occurs at the level of 2-hydroxyisoflavanone, the direct product of the "isoflavone synthase" (IFS) that constitutes the entry point into the isoflavonoid pathway (Akashi et al., 2000). 2,7,4'-Trihydroxyisoflavanone 4'-OMT (HI4'OMT; e.g. GenBank accession AB091686) catalyzes the methylation of the 4'-position of 2-hydroxyisoflavanone to form 2,7-dihydroxy, 4'-methoxyisoflavanone, which undergoes dehydration to yield the isoflavone formononetin (FIG. 1). Formononetin accumulates in several legumes and is also a precursor in the biosynthesis of medicarpin and related pterocarpanoid phytoalexins. HI4'OMT is closely related to PsHMM at the amino acid sequence level (Asamizu et al., 2000; Akashi et al., 2003). GenBank accession AY942158 describes a *M. truncatula* isoflavonoid methyltransferase.

Recently, a 4'-OMT from *Glycine max* (SOMT-2) was reported to methylate daidzein, genistein, and naringenin (Kim et al., 2005). SOMT-2 is 67% identical to MsI7OMT and MtIOMT1 and only 48-53% identical to OMTs within the HI4'OMT clade. However, in contrast to the IOMTs described below, SOMT-2 methylated apigenin and quercetin.

An extensive metabolite profile of *M. truncatula* roots or root exudates has not been reported. Further evidence of the role of MtIOMTs in isoflavonoid biosynthesis awaits reverse genetic approaches coupled with extensive metabolic profiling to include secreted compounds. It has also been observed that, at least in vitro, some plant small molecule OMTs may form heterodimers with altered substrate preferences and specificities (Frick et al., 2001), although it is unclear whether such a phenomenon can occur in vivo.

While the foregoing studies have provided a further understanding of the biosynthesis of plant secondary metabolites, methods for the efficient modification of most secondary metabolites have been lacking. This has been particularly true in the case of isoflavonoid biosynthesis. There therefore remains a great need in the art for the development of methods and compositions that would increase the efficiency by which isoflavonoid biosynthesis can be modified in plants.

SUMMARY OF THE INVENTION

In one aspect the invention provides an isolated nucleic acid sequence encoding a plant isoflavonoid O-methyltransferase. In certain embodiments the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d).

Another aspect of the invention provides a recombinant vector comprising an isolated nucleic acid sequence encoding a plant isoflavonoid O-methyltransferase operably linked to a heterologous promoter. The invention further provides a recombinant vector comprising the nucleic acid encoding a plant isoflavonoid O-methyltransferase operably linked to a heterologous promoter, further comprising at least one additional sequence chosen from the group consisting of: a regulatory sequence, a selectable marker, a leader sequence and a terminator. The additional sequence may be a heterologous sequence. Further, in such a recombinant vector, the promoter may be a developmentally-regulated, organelle-specific, inducible, tissue-specific, constitutive, cell-specific, seed specific, or germination-specific promoter. The recombinant vector may be further defined as an isolated expression cassette.

Another aspect of the invention comprises an isolated polypeptide selected from the group consisting of: (a) a polypeptide comprising the amino acid sequence of SEQ ID NO:9, 10, 11, 13, 14, or 15; (b) a polypeptide comprising a fragment of the amino acid sequence of SEQ ID NO:9, 10, 11, 13, 14, or 15 having isoflavonoid O-methyltransferase activity; and (c) a polypeptide having at least 85% sequence identity to SEQ ID NO:9, 10, 11, 13, 14, or 15 and having isoflavonoid O-methyltransferase activity.

Yet another aspect of the invention comprises a transgenic plant transformed with a recombinant vector comprising an isolated nucleic acid sequence encoding a plant isoflavonoid O-methyltransferase wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), and wherein the recombinant vector comprises such an isolated polynucleotide operably linked to a heterologous promoter.

The invention further provides a transgenic plant comprising a recombinant vector comprising a nucleic acid encoding a plant isoflavonoid O-methyltransferase, further comprising at least one additional sequence chosen from the group consisting of: a regulatory sequence, a selectable marker, a leader sequence and a terminator. The additional sequence may be a heterologous sequence. Further, in such a recombinant vector, the promoter may be a developmentally-regulated, organelle-specific, inducible, tissue-specific, constitutive, cell-specific, seed specific, or germination-specific promoter. The recombinant vector transformed into the plant may be further defined as an isolated expression cassette.

In certain embodiments, the transgenic plant may be further defined as a monocotyledonous plant, or as a dicotyledonous plant. In particular embodiments, the transgenic plant may be further defined as a legume. The transgenic plant may also be further defined as an $R_0$ transgenic plant, or as a progeny plant of any generation of an $R_0$ transgenic plant, wherein said transgenic plant has inherited said selected DNA from said $R_0$ transgenic plant. In yet further embodiments, the invention comprises a plant part of the transgenic plant. A seed of the transgenic plant wherein said seed comprises a recombinant vector encoding a plant isoflavonoid O-methyltransferase wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), and wherein the recombinant vector comprises such an isolated polynucleotide operably linked to a heterologous promoter is also provided by the invention.

A host cell transformed with a recombinant vector comprising an isolated nucleic acid sequence encoding a plant isoflavonoid O-methyltransferase wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), and wherein the isolated polynucleotide is operably linked to a heterologous promoter comprises another aspect of the invention. The host cell may be a plant cell.

Another aspect of the invention comprises a method of altering flavonoid synthesis in a plant comprising introducing into said plant a recombinant vector comprising an isolated nucleic acid sequence encoding a plant isoflavonoid O-methyltransferase, wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), wherein the isolated polynucleotide is operably linked to a heterologous promoter, and wherein the recombinant vector further comprises at least one additional sequence chosen from the group consisting of: a regulatory sequence, a selectable marker, a leader sequence and a terminator. The additional sequence may be a heterologous sequence. Further, in such a recombinant vector, the promoter may be a developmentally-regulated, organelle-specific, inducible, tissue-specific, constitutive, cell-specific, seed specific, or germination-specific promoter, and the nucleic acid sequence encoding isoflavonoid O-methyltransferase is expressed to alter flavonoid biosynthesis in the plant relative to a plant of the same genotype lacking the recombinant vector. In certain embodiments of the method, the recombinant vector may be inherited from a parent plant of said plant. In other embodiments the plant may be an $R_0$ plant transformed with the recombinant vector.

Yet another aspect of the invention comprises a method of increasing disease resistance in a plant, comprising introducing into said plant the recombinant vector comprising an isolated nucleic acid sequence encoding a plant isoflavonoid O-methyltransferase, wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), wherein the isolated polynucleotide is operably linked to a heterologous promoter, and wherein the nucleic acid sequence encoding isoflavonoid O-methyltransferase is expressed to increase disease resistance in the plant relative to a plant of the same genotype lacking the nucleic acid sequence. In certain embodiments, the recombinant vector is inherited from a parent plant of said plant. In other embodiments, the plant is directly transformed with the recombinant vector.

The invention further comprises a method of producing food for human or animal consumption comprising: (I) obtaining a transgenic plant which comprises a recombinant vector encoding a plant isoflavonoid O-methyltransferase wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), and wherein the recombinant vector comprises such an isolated polynucleotide operably linked to a heterologous promoter; (II) growing said plant under plant growth conditions to produce plant tissue from the plant; and (III) preparing food for human or animal consumption from said plant tissue. In certain embodiments, the method of preparing food comprises harvesting said plant tissue. The food prepared by such a method may be starch, protein, meal, flour or grain.

Yet another aspect of the invention comprises a method of producing a nutraceutical composition comprising (I) obtaining a plant comprising an isolated nucleic acid sequence encoding a plant isoflavonoid O-methyltransferase, wherein the nucleic acid sequence is selected from the group consisting of: (a) a nucleic acid sequence encoding the polypeptide of SEQ ID NO:9, 10, 11, 13, 14, or 15; (b) a nucleic acid sequence comprising the sequence of SEQ ID NO:2, 3, 4, 6, 7, or 8; (c) a nucleic acid sequence that hybridizes to SEQ ID NO: 2, 3, 4, 6, 7, or 8 under conditions of 0.15 M NaCl and 70° C.; (d) a nucleic acid sequence with at least 85% sequence identity to the nucleic acid sequence of SEQ ID NOs: 2, 3, 4, 6, 7, or 8; and (e) a nucleic acid sequence complementary to the sequence of (a), (b), (c) or (d), wherein the recombinant vector comprises the isolated polynucleotide operably linked to a heterologous promoter; (II) growing said plant under plant growth conditions to produce plant tissue from the plant; and (III) preparing a nutraceutical composition for human or animal consumption from said plant tissue. A nutraceutical composition prepared by such a method is also an aspect of the invention.

The use of the word "a" or "an" when used in conjunction with the term "comprising" in the claims and/or the specification may mean "one," but it is also consistent with the meaning of "one or more," "at least one," and "one or more than one."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

FIG. 3B is modeled after Schroder et al (2004).

DETAILED DESCRIPTION OF THE INVENTION

Figure 1:
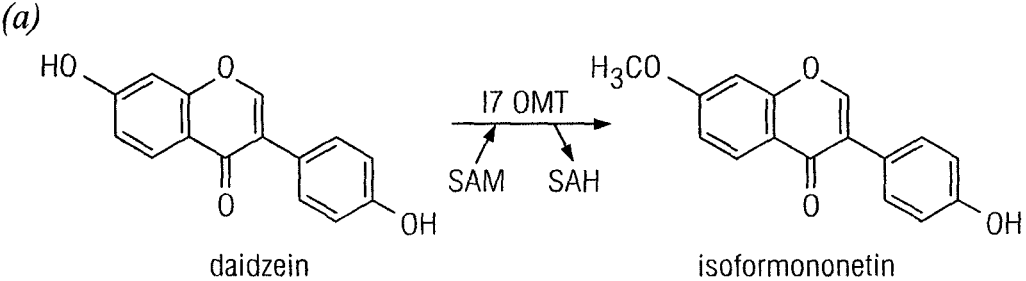
FIG. 1. Isoflavone 7-OMT (I7OMT) (a) and 2-hydroxyisoflavanone 4'-OMT (HI4'OMT) (b) activities characterized from legumes. SAM, S-adenosyl-L-methionine; SAH, S-adenosylhomocysteine.
Figure 1:
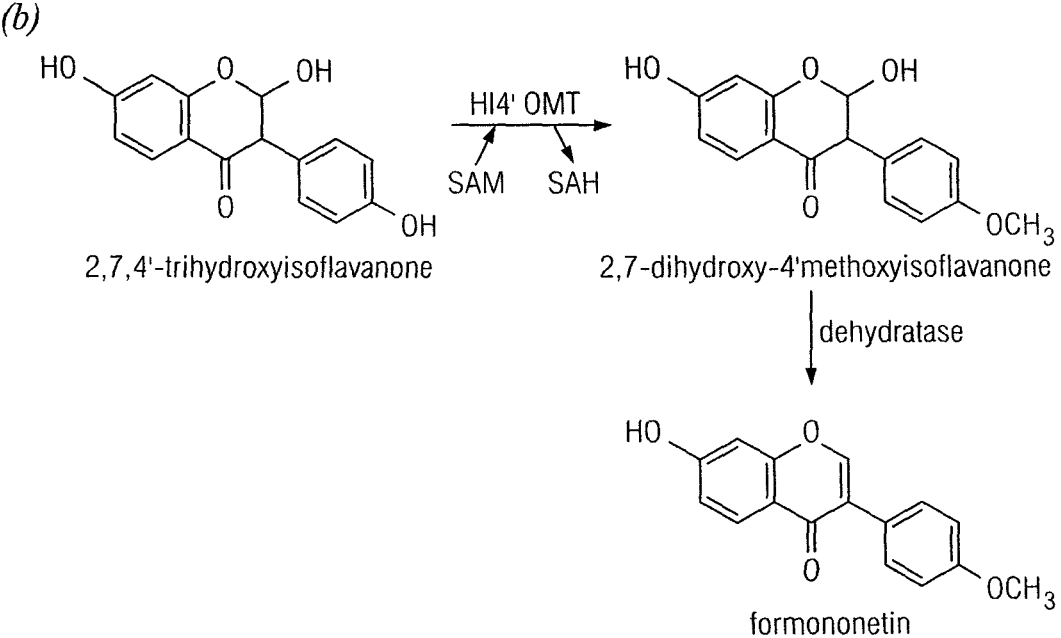

The invention provides plant O-methyltransferase coding sequences. In one aspect, these sequences encode proteins that methylate one or more flavonoids or isoflavonoids. The invention also provides *Medicago truncatula* O-methyltransferase peptides that methylate flavonoid and/or isoflavonoid compounds, and transgenic plants comprising such sequences and peptides.

In certain embodiments, the plant O-methyltransferase coding sequences may comprise SEQ ID NO:2, SEQ ID NO:3, SEQ ID NO:4, SEQ ID NO:6, SEQ ID NO:7, or SEQ ID NO:8. In other embodiments, the plant O-methyltransferase coding sequences comprise sequences that encode the polypeptides of SEQ ID NO:9, SEQ ID NO:10, SEQ ID NO:11, SEQ ID NO:13, SEQ ID NO:14, or SEQ ID NO:15. In yet other embodiments, the nucleotide sequences that encode polypeptides displaying plant O-methyltransferase activity are at least 85% similar to SEQ ID NO:2, SEQ ID NO:3, SEQ ID NO:4, SEQ ID NO:6, SEQ ID NO:7, or SEQ ID NO:8, or at least 90% or at least 95% or at least 98% similar to SEQ ID NO:2, SEQ ID NO:3, SEQ ID NO:4, SEQ ID NO:6, SEQ ID NO:7, or SEQ ID NO:8. In still further embodiments, the encoded polypeptides displaying plant O-methyltransferase activity may display at least 85%, at least 90%, at least 95%, or at least 98% sequence similarity to SEQ ID NO: SEQ ID NO:9, SEQ ID NO:10, SEQ ID NO:11, SEQ ID NO:13, SEQ ID NO:14, or SEQ ID NO:15.

Expressed sequence tag (EST) libraries obtained from the model legume *Medicago truncatula* contain several related OMT sequences with similarity to I7OMT or HI4'OMT, potentially encoding isoflavone 7-OMTs, 2-hydroxyisoflavanone 4'-OMTs, or 6a-hydroxymaackiain OMTs. To better understand the nature of the OMTs catalyzing the 4' and 7-O-methylation reactions during isoflavonoid biosynthesis in *Medicago*, and to provide experimental evidence for their activity based on sequence similarity, seven putative *M. truncatula* IOMTs (MtIOMTs) were cloned and heterologously expressed, and their relative specificities for (iso)flavonoid substrates were determined. Remarkably, several of the OMTs methylate both the 4'- and 7-positions of selected (iso)flavonoid compounds in vitro, and structure modeling was used to predict potential regio- and stereo-specificities. The expression patterns of the MtIOMTs were examined in different plant organs, in leaves in response to fungal infection, and in cell suspension cultures exposed to yeast elicitor (YE) or methyl jasmonate (MeJa). The alteration of (iso) flavonoid biosynthesis by these sequences also has plant growth, nutritional and nutraceutical significance given the importance of this class of biomolecules.

Nutritional and/or food quality benefits may be obtained by altering and/or increasing (iso)flavonoid biosynthesis. This may be carried out to achieve the many health benefits known to be associated with (iso)flavones. It may therefore be beneficial to prepare nutraceuticals from the plants provided by the invention.

In another aspect, the invention overcomes the limitations of the prior art by providing improved methods for the modification of plant biosynthetic pathways as well as for enabling the production of (iso)flavonoids in plants that do not normally produce (iso)flavonoids, or normally produce different (iso)flavonoids. The engineering of (iso)flavonoid biosynthesis in plants is of particular importance due to the numerous health and other benefits that have been associated with plant isoflavonoid secondary metabolites. Irrespective of their in vivo function in the plant, the genes and polypeptides described here have potential value as reagents for metabolic engineering, providing a means for regiospecific introduction of methyl groups to (iso)flavonoid skeletons to generate novel bioactive compounds.

In yet another aspect, the invention provides a method of increasing insect and/or pest resistance in a plant comprising introducing into said plant a recombinant vector comprising a nucleic acid sequence encoding isoflavonoid O— methyltransferase, wherein the sequence is expressed to increase insect and/or pest resistance in the plant relative to a plant of the same genotype lacking the nucleic acid sequence.

I. IN VIVO PHYSIOLOGICAL ROLES OF MEDICAGO IOMTS IN RELATION TO METABOLITE COMPOSITION

Figure 9:
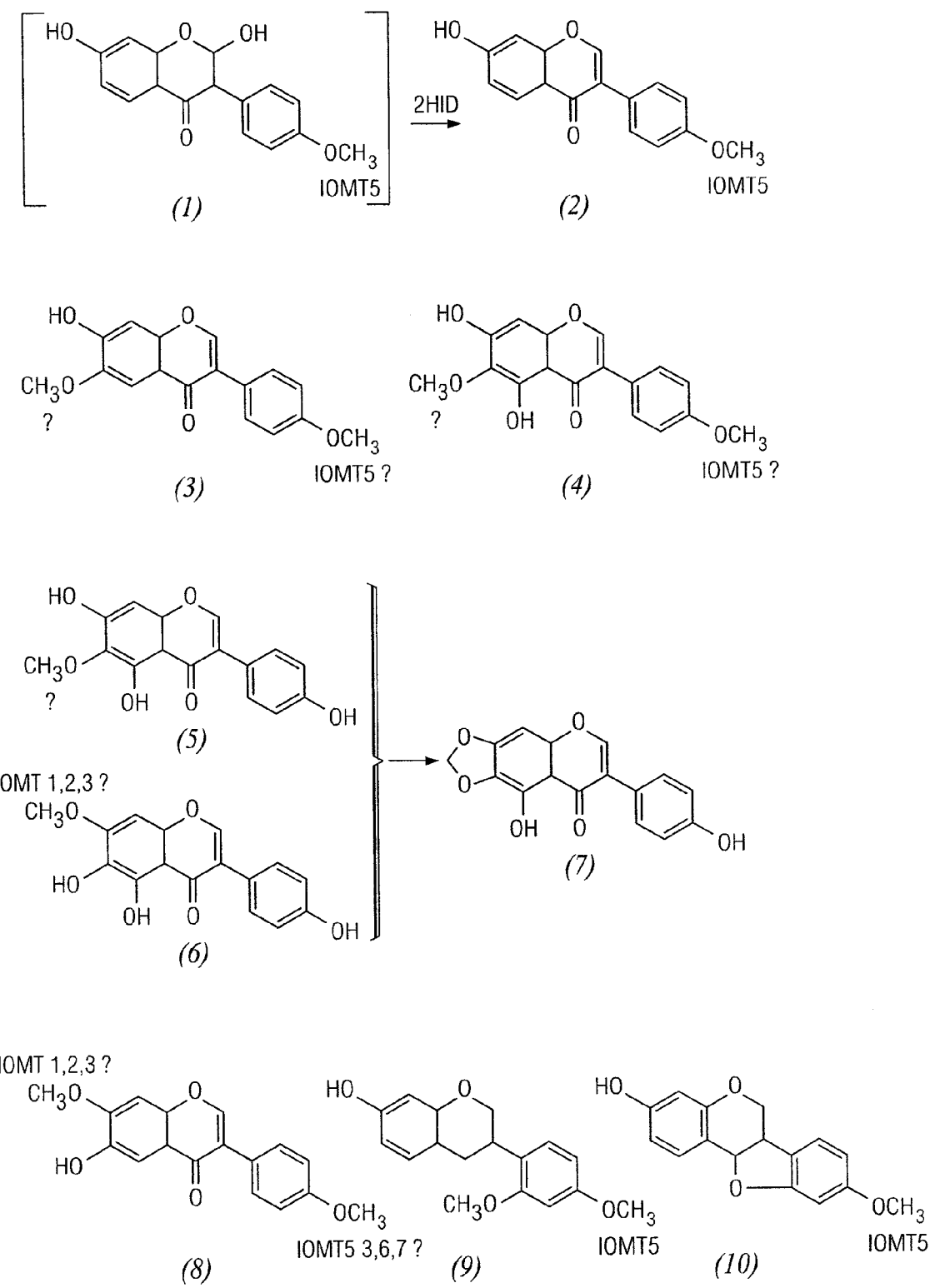
FIG. 9. Methylated isoflavonoids identified in *Medicago truncatula* cell suspension cultures (Suzuki et al., 2005). Methyl groups on different positions are shown, along with OMTs potentially involved in their formation. Individual compounds are numbered (1), etc., and cross-referenced in the text. Reaction schemes are shown for conversion of 2,7,4'-trihydroxyisoflavanone (1) to formononetin (2) by 2-hydroxyisoflavanone dehydratase (2HID) and for methylenedioxy ring closure to form irilone (7) from putative 6- or 7-O-methylated precursors (5, 6).

Several studies have documented the (iso)flavonoid constituents of *Medicago truncatula* and related species. These include early studies of intact plant tissues (Bisby et al., 1994), and more recent in-depth metabolomic studies of yeast- and MeJA-elicited cell suspension cultures (e.g. Suzuki et al., 2005) or *Phoma*-infected leaves (Deavours and Dixon, 2005) (FIG. 9). Based on such phytochemical analysis, and the present data on in vitro substrate specificities and expression patterns of putative IOMTs, several conclusions can be made. The numbering of compounds below reflects the numbering of FIG. 9.

First, the 4'-O-methyl group of formononetin (2) and compounds derived therefrom (such as medicarpin), originates via IOMT5 (a true 2,7,4'-trihydroxyisoflavanone OMT) in *Medicago*. 7-Methoxy, 4',5,6-trihydroxyisoflavone (6), although yet detected in *Medicago*, is a potential precursor of irilone (7) and the corresponding tetrahydroxyisoflavone is therefore a candidate substrate for I7OMTs, although the A-ring methylenedioxy group on irilone could also arise via a 6-O-methylated intermediate (5). Assuming that the first methylation reaction of the isoflavone nucleus occurs immediately after aryl ring migration, catalyzed by MtIOMT5, formation of alfalone (8) and afromosin (3) would likely require subsequent OMTs active with 6,7-dihydroxy, 4'-methoxyisoflavone. Interestingly, none of the enzymes described below possessed such specificity (Table 3), the presence of the 4'-methoxyl group blocking activity.

Formononetin (2) and medicarpin (10) conjugates occur in *M. truncatula* roots (Harrison and Dixon, 1993). Infection of *M. truncatula* leaves with *P. medicaginis* results in accumulation of the isoflavonoids coumestrol (non-methylated), afrormosin (3) and medicarpin (10) in addition to several unidentified compounds. Like MsI7OMT (He and Dixon, 2000), MtIOMT1 is induced in response to fungal infection and its expression pattern is nearly identical to that of MtIOMT5. However, the in vitro activity of MtIOMT1 is inconsistent with a role in the biosynthesis of formononetin (also known as 4'-O-methyldaidzein) and/or medicarpin. Microarray data also showed that transcription patterns of MtIOMT1 and MtIOMT5 are different in response to YE and MeJA treatment. MtIOMT1 may be involved in the biosynthesis of other, unidentified compounds that were observed to accumulate in *P. medicaginis* infected leaves. It is also possible that the product of MtIOMT1 activity does not accumulate to significant levels or that MtIOMT1 may have a signaling, rather than a biosynthetic role.

The phytoalexin sativan (7-hydroxy, 2',4'-dimethoxyisoflavan, (9) has been reported in *M. truncatula* (Bisby et al., 1994) and is likely formed by 2'-O-methylation of vestitol. MtIOMT2, MtIOMT4, MtIOMT5, MtIOMT6, and MtIOMT7 all methylated vestitol in vitro, although the position of methylation cold not be confirmed.

Based on their reported occurrence in *M. sativa* and/or *M. truncatula*, other potential products of MtIOMT activity include the coumestans sativol (7-methoxy, all numbering is relative to isoflavone), wairol (6'-methoxy), 7,12-dihydroxy-11-methoxycoumestan (5'-methoxy), the isoflavans 7-hydroxy-2',3',4'-trimethoxyisoflavan (2',3',4'-trimethoxy) and 5'-methoxysativan (5'-methoxy), and the pterocarpans 4-methoxymedicarpin (6-methoxy) and methylnissolin (3-methoxy) (Bisby et al., 1994). Due to the unavailability of appropriate substrates, it was not feasible to determine whether any of the characterized MtIOMTs are potentially involved in the synthesis of these compounds.

All MtIOMTs were expressed in the roots of *M. truncatula*. Root secreted isoflavonoids are known signaling molecules in the interaction of legumes with the rhizosphere, mediating both positive and negative interactions with symbiotic and pathogenic microorganisms (Phillips and Kapulnik, 1995).

Genistein is well-known for its phytoestrogenic activities (Barnes, 2004; Dixon and Ferreira, 2002), but is also a building block for many structurally more complicated isoflavonoid compounds. Most plant species accumulate flavonoids and anthocyanins, hence their biosynthetic precursor, chalcone, is available as a substrate for introducing the isoflavonoid pathway into non-legume plants.

II. PLANT EXPRESSION CONSTRUCTS AND NUCLEIC ACIDS

In one aspect of the invention, plant transformation vectors comprising a nucleic acid encoding polypeptide are provided. An exemplary construct according to the invention comprises a promoter functional in a plant operably linked to a nucleic acid sequence encoding polypeptide.

In one embodiment of the invention, a polypeptide is therefore provided that comprises an enzyme coding sequence or the polypeptide encoded thereby set forth in the Sequence Listing, as well as polypeptides and fragments thereof, particularly those polypeptides which exhibit enzyme activity have at least 85%, more preferably at least 90% identity, and most preferably at least 95% identity to a polypeptide sequence selected from the group of sequences set forth in the Sequence Listing. "Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Lesk (1988); Smith (1993); Griffin, and Griffin (1994); von Heinje (1987); Gribskov, and Devereux (1991); and Carillo and Lipman, (1988). Computer programs can be used to determine "identity" between two sequences these programs include but are not limited to, GCG (Devereux et al., 1984); suite of five BLAST programs, three designed for nucleotide sequences queries (BLASTN, BLASTX, and TBLASTX) and two designed for protein sequence queries (BLASTP and TBLASTN) (Coulson, 1994; Birren et al., 1997). The BLAST X program is publicly available from NCBI and other sources (BLAST Manual, Altschul et al., NCBI NLM NIH, Bethesda, Md. 20894; Altschul et al., 1990). The well known Smith Waterman algorithm can also be used to determine identity.

Parameters for polypeptide sequence comparison include the following: Algorithm: Needleman and Wunsch, (1970); Comparison matrix: BLOSSUM62 from Hentikoff and Hentikoff (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

The invention therefore provides nucleic acids encoding polypeptide described herein. The nucleic acid may be defined as comprising nucleic acids encoding, in frame, the polypeptide. Those of skill in the art will understand in view of the disclosure that such nucleic acids may be provided as an expression construct by linking appropriate regulatory elements to the nucleic acid corresponding to a host cell in which heterologous expression is desired. For plant expression, a plant promoter may be operably linked to the nucleic acid. In addition, other elements such as enhancers, terminators and transit peptides may be used. Endogenous or heterologous elements may be used. For example, MtIOMT could be placed at the N-terminus of the encoded polypeptide in order to utilize a native endoplasmic reticulum localization peptide.

The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

One important use of the sequences provided by the invention will be in the alteration of plant phenotypes by genetic transformation with coding sequences that alter plant secondary metabolite biosynthesis as described herein. The coding sequences may be provided with other sequences such as regulatory elements or other coding sequences. Where a selectable or screenable marker is used, one may employ the separate coding regions on either the same or different DNA segments for transformation. In the latter case, the different vectors are delivered concurrently to recipient cells to maximize co-transformation.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant. Introduction of such sequences may be facilitated by use of bacterial or yeast artificial chromosomes (BACs or YACs, respectively), or even plant artificial chromosomes. For example, the use of BACs for Agrobacterium-mediated transformation was disclosed by Hamilton et al. (1996).

Particularly useful for transformation are expression cassettes which have been isolated from such vectors. DNA segments used for transforming plant cells will, of course, generally comprise coding sequence which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components that may be included with plant transformation vectors are as follows.

A. Regulatory Elements

Exemplary promoters for expression of a nucleic acid sequence in plants include the CaMV 35S promoter (Odell et al., 1985), CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or R gene complex associated promoters (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of a isoflavone biosynthesis sequence is used. In another embodiment, a heterologous sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that nucleic acids encoding a polypeptide as provided herein may be introduced under the control of novel promoters or enhancers, etc., or homologous or tissue specific promoters or control elements. Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots or wounded leaf tissue.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. Alternatively, a heterologous 3' end may enhance the expression of coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, Golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity.

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154,204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; or a gene encoding for green fluorescent protein (Sheen et al., 1995; Haseloff et al., 1997; Reichel et al., 1996; Tian et al., 1997; WO 97/41228).

III. METHODS FOR GENETIC TRANSFORMATION

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384, 253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464, 765, specifically incorporated herein by reference in its entirety), by *Agrobacterium*-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

A. *Agrobacterium*-Mediated Transformation

*Agrobacterium*-mediated transfer is a widely applicable system for introducing genes into plant cells because the DNA can be introduced into whole plant tissues, thereby bypassing the need for regeneration of an intact plant from a protoplast. The use of *Agrobacterium*-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

*Agrobacterium*-mediated transformation is most efficient in dicotyledonous plants and is the preferable method for transformation of dicots, including *Arabidopsis*, tobacco, tomato, alfalfa and potato. Indeed, while *Agrobacterium*-mediated transformation has been routinely used with dicotyledonous plants for a number of years, it has only recently become applicable to monocotyledonous plants. Advances in *Agrobacterium*-mediated transformation techniques have now made the technique applicable to nearly all monocotyledonous plants. For example, *Agrobacterium*-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998) and maize (Ishidia et al., 1996).

Modern *Agrobacterium* transformation vectors are capable of replication in *E. coli* as well as *Agrobacterium*, allowing for convenient manipulations as described (Klee et al., 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, *Agrobacterium* containing both armed and disarmed Ti genes can be used for the transformations. In those plant strains where *Agrobacterium*-mediated transformation is efficient, it is the method of choice because of the facile and defined nature of the gene transfer.

B. Electroporation

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner. Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

C. Microprojectile Bombardment

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

D. Other Transformation Methods

Transformation of protoplasts can be achieved using methods based on calcium phosphate precipitation, polyethylene glycol treatment, electroporation, and combinations of these treatments (see, e.g., Potrykus et al., 1985; Lorz et al., 1985; Omirulleh et al., 1993; Fromm et al., 1986; Uchimiya et al., 1986; Callis et al., 1987; Marcotte et al., 1988).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant lines that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety (Thompson, 1995), and rice (Nagatani, 1997).

E. Tissue Cultures

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Nutrient media is prepared as a liquid, but this may be solidified by adding the liquid to materials capable of providing a solid support. Agar is most commonly used for this purpose. Bactoagar (e.g. Difco Laboratories, Detroit, Mich.), Hazelton agar, Gelrite, and Gelgro are specific types of solid support that are suitable for growth of plant cells in tissue culture.

Some cell types will grow and divide either in liquid suspension or on solid media. As disclosed herein, plant cells will grow in suspension or on solid medium, but regeneration of plants from suspension cultures typically requires transfer from liquid to solid media at some point in development. The type and extent of differentiation of cells in culture will be affected not only by the type of media used and by the environment, for example, pH, but also by whether media is solid or liquid.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Manual selection of recipient cells, e.g., by selecting embryogenic cells from the surface of a Type II callus, is one means that may be used in an attempt to enrich for particular cells prior to culturing (whether cultured on solid media or in suspension).

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

IV. PRODUCTION AND CHARACTERIZATION OF STABLY TRANSFORMED PLANTS

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphotransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces viridochromogenes*. The use of the herbicide resistance gene encoding phosphinothricin acetyl transferase (PAT) is referred to in DE 3642 829 A, wherein the gene is isolated from *Streptomyces viridochromogenes*.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on polypeptides encoded by the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use a bar-bialaphos or the EPSPS-glyphosate selective system, for example, transformed tissue can be cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate may be preferred, it is proposed that ranges of 0.1-50 mg/l bialaphos or 0.1-50 mM glyphosate will find utility.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discrete fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

V. BREEDING PLANTS OF THE INVENTION

In addition to direct transformation of a particular plant genotype with a construct prepared according to the current invention, transgenic plants may be made by crossing a plant having a selected DNA of the invention to a second plant lacking the construct. For example, a selected polypeptide coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

VI. DEFINITIONS

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VII. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

Example 1

Cloning, Expression, and Purification of M. truncatula IOMTs

Candidate M. truncatula IOMTs were identified by searching MtGI Release 7.0 (May 1, 2003) (www.tigr.org/tigr-scripts/tgi/T_index.cgi?species=medicago) for ESTs with similarity to M. sativa I7OMT (GB accession number U97125) using BLAST searches. Full-length ESTs for MtIOMT1 (NF070A11EC1F1082) were obtained from an elicited M. truncatula cell culture library; full length MtIOMT3 ESTs (NF027F03PL1F1029) were obtained from a phosphate-starved leaf library; full length MtIOMT4 ESTs (N201058e) were obtained from a phosphate-starved root library; full length MtIOMT6 (NF031D06RT1F1046), MtIOMT7 (NF005H09RT1F1079), and MtIOMT8 ESTs (NF031H02RT1F1016) were obtained from a M. truncatula developing root library.

Cloning of MtIOMT5 (corresponding to TC100926, TIGR MtGI v.8) was as described previously (Liu et al., 2005). To obtain a full-length cDNA for MtIOMT2, specific primers designed based upon the M. truncatula genomic sequence were used to amplify the MtIOMT2 coding sequence from M. truncatula root cDNA. The amplified product was cloned into the pGEM®-T easy vector (Promega, Madison Wis.) and sequenced to confirm its identity. MtIOMTs were cloned into the pET28a vector (EMD Biosciences, Inc., San Diego, Calif.) using PCR-based amplification with primers designed to introduce EcoRI and XhoI restriction sites; BamHI and XhoI sites were used for cloning MtIOMT6 due to the presence of an internal EcoRI site in this particular cDNA. Because the EST for MtIOMT8 was missing a start codon, the primer designed to clone MtIOMT8 into pET28a contained an additional 2-nucleotide insertion to generate an ATG start site. All MtIOMTs were expressed as translational fusions to an N-terminal His-tag. Expression of MtIOMTs in E. coli BL21(DE3) and purification by $Ni^{2+}$-NTA chromatography were as described (Zubieta et al., 2001). Proteins were dialyzed against 20 mM Tris pH 8.0, 100 mM NaCl, 10% (v/v) glycerol, and 14 mM β-mercaptoethanol. Protein concentration was determined by Bradford assay using BSA as a standard (Bradford, 1976).

Example 2

OMT Assays

Reactions (200 µl) were performed in 0.1 M potassium phosphate, pH 7.4, 10% (w/v) sucrose, 14 mM β-mercaptoethanol with 10 µM protein, 0.5 mM S-adenosyl-L-methionine, and 80 µM phenolic substrates. All substrates were purchased from Indofine (Hillsborough, N.J.) except 6,7-dihydroxy-4'-methoxyisoflavone, dihydrodaidzein, and vestitol, which were purchased from Apin (Oxfordshire, UK). 2,7,4'-Trihydroxyisoflavanone was purified from IFS reactions carried out with liquiritigenin as described (Liu et al., 2005). OMT assays were incubated at 30° C. for 2 h and extracted with ethyl acetate. Ethyl acetate extracts were dried under $N_2$ and the resultant material was resuspended in 50-100 µl of methanol. Samples were analyzed on an Agilent 1100 HPLC, equipped with a quaternary pump (model #G1311A), a degasser (model #G1322A), an autosampler (model #G1313A), and a diode array detector (model #G1315A). Samples of 20 µl were applied to an ODS2 reverse-phase column (5 µm particle size, 4.6×250 mm) and eluted in 1% (v/v) phosphoric acid with an increasing gradient of acetonitrile (0-5 min, 25%; 5-35 min, 25-50%; 35-39 min, 50-100%) at a flow rate of 1 ml/min. To resolve the 4'-O-methylated and 7-O-methylated products of genistein, samples were applied to a Phenomenex SYNERGI Polar-RP 80 Å column (4 µm particle size, 4.6×250 mm) and eluted in water with an increasing gradient of acetonitrile (0-5 min, 20%; 5-17 min, 20-38%; 17-33 min, 38%; 33-45 min, 38-56%; 45-46 min, 56-100%) at a flow rate of 1 ml/min. Chiral chromatography was performed as described (Liu et al., 2005).

For determination of specific activities, reactions (100 µl) were performed in 0.1 M potassium phosphate, pH 7.4, 10% (w/v) sucrose, 14 mM β-mercaptoethanol with 0.2-µg protein, 50 µM S-adenosyl-L-methionine (0.025 µCi $^{14}$C-SAM per reaction), and 100 µM substrate. Reactions were incubated at 30° C. for 15-25 min and stopped by addition of 4 µl of 1N HCl. Products were extracted into 500 µl of ethyl acetate and 400 µl was used for liquid scintillation counting.

Example 3

Tandem MS Analysis

An HP 1100 series II LC system (Hewlett-Packard, Palo Alto, Calif.) with a photodiode array detector was coupled to a Bruker Esquire ion-trap mass spectrometer (ITMS) equipped with an electrospray ionization source. A reverse phase, C18, 5 µm, 4.6×250 mm column (J. T. Baker, Phillipsburg, N.J.) was used for separations. The mobile phase consisted of 0.1% (v/v) acetic acid using linear gradients of 5-90% acetonitrile (v/v) in 70 min. The flow rate was 0.8 ml/min, and the temperature of the column was kept at 28° C. Both positive- and negative-ion mass spectra were acquired. Positive-ion ESI was performed using an ion source voltage of 4.0 KV and a capillary offset voltage of 86.0 V. Nebulization was aided with a coaxial nitrogen sheath gas provided at a pressure of 60 psi. Desolvation was aided using a counter current nitrogen flow set at a pressure of 12 psi and a capillary temperature of 300° C. Mass spectra were recorded over the range 50-2200 m/z. The ITMS was operated under an ion current control of approximately 10,000 with a maximum acquire time of 100 ms. Tandem mass spectra were obtained in manual mode for targeted masses using an isolation width of 2.0, fragmentation amplitude of 2.2 and threshold set at 6,000.

Example 4

Measurement of IOMT Transcript Levels

Infection of M. truncatula with Phoma medicaginis was performed as described (Deavours and Dixon, 2005). RNA was extracted from plant tissues using TRI Reagent (Molecular Research Center, Inc., Cincinnati, Ohio) according to the manufacturer's instructions. For RT-PCR, 2 µg of total RNA was transcribed into cDNA using Ready-To-Go RT-PCR beads (Amersham, Piscataway, N.J.) and oligo-dT primer. Two µl of cDNA was used in each PCR reaction (50 µl total) with Ex-Taq PCR reagents (Takara Bio Inc., Shiga, Japan) and the primers used are listed in Table 1 (SEQ ID NOs:16-29). PCR conditions were 94° C., 5 min; 25-32 cycles of 94° C. for 1 min, 55° C. for 1 min, 72° C. for 1 min; followed by 72° C. for 10 min. PCR products were resolved on a 1% (w/v) TAE-agarose gel and visualized with ethidium bromide.

TABLE 1

Primers used for RT-PCR (listed 5' to 3'; SEQ ID NOs:16-29)

| Reverse Primer | Forward Primer | Corresponding MtIOMT |
|---|---|---|
| cttcttctccttctttgccat (seq id no:16) | agaaacacaagacatcacccaag (seq id no:17) | MTIOMT7 |
| acacaactccagtcccacctg (seq id no:18) | acatggaaagcctatgactgttc (seq id no:19) | MTIOMT6 |
| aactttgcagcaacttcagg (seq id no:20) | acaatagtgaaaggcaaagaaggagat (seq id no:21) | MTIOMT5 |
| atacgaccgtatcaatatgcct (seq id no:22) | ttaacaccaatggttcttatgtctac (seq id no:23) | MTIOMT4 |
| tccaatcatgcaaaaccgc (seq id no:24) | gttcttgatccaacactttcaac (seq id no:25) | MTIOMT3 |
| ggatcaaacagaaccaaacattac (seq id no:26) | ggatcaaacagaaccaaacattac (seq id no:27) | MTIOMT2 |
| gaatgcatgatggatcaatacaaa (seq id no:28) | cgggttcgtatcatgagctg (seq id no:29) | MTIOMT1 |

Example 5

DNA Microarray Analysis

The Affymetrix DNA chip contained 61,200 probe sets: 32,167 *M. truncatula* EST/mRNA-based and chloroplast gene-based probe sets (TIGR Gene Index version 8, January, 2005, 36,878 unique sequences); 18,733 *M. truncatula* IMGAG (International *Medicago* Genome Annotation Group) and phase 2/3 BAC prediction-based probe sets; 1,896 *M. sativa* EST/mRNA based probe sets; 8,305 *Sinorhizobium meliloti* gene prediction-based probe sets. For microarray experiments, total RNA was extracted from cell suspension cultures (Suzuki et al., 2005) using TRI Reagent (Molecular Research Center, Inc., Cincinnati, Ohio) and purified using the RNeasy® MinElute Cleanup Kit (Qiagen, Valencia, Calif.), according to the manufacturer's instructions. For all samples, 10 µg of total RNA was used for labeling reactions. Labeling, hybridization and data processing were performed according to the manufacturer's instruction (Affymetrix, Santa Clara, Calif.). For both YE and MeJA treatments, transcript profiles were examined at early (2 h) and late (24 h) time post-elicitation. For each sample point, two biological replicates were included, and the average signal intensities were used to calculate ratio of treatment to its corresponding control.

Example 6

Homology Remodeling and Automated Substrate Docking

The MtIOMT amino acid sequences were aligned to MsI7OMT using CLUSTAL W version 1.82 (Thompson et al., 1994) and homology models were built using the program MODELLER (Marti-Renom et al., 2000) based upon the crystal structure of the MsI7OMT-isoformononetin complex (PDB:1FP2) (Zubieta et al., 2001). For each MtIOMT, five models were generated and ranked by Model Rank in the MODELLER package. The top ranked models were chosen and visualized using O (Jones et al., 1991), and quantitatively evaluated using the program Procheck (Laskowski et al., 1993). For substrate docking analyses, Genetic Optimization for Ligand Docking (GOLD) (Otwinowski and Minor, 1997) and DOCK (e.g. Ewing et al., 2001) were used. When GOLD was used for docking runs, the parameters controlling the precise operation of the genetic algorithm were as follows: population size=100, selection pressure=1.100000, number of operations=100,000, number of islands=5, niche size=2, crossover weight=95, mutate weight=95, and migrate weight=10. Default parameter values for van der Waals interactions and hydrogen bonding were used throughout the docking process. The volume of the active site was defined using a 15 Å radius centered around the NE2 atom of the catalytic His residue. Ten docking calculations were run for each ligand and the GOLD score was used to identify the lowest energy docking results.

Example 7

MtIOMT Sequences and Activities

A. Isolation and Sequence Analysis of MtIOMTs

Sequences were aligned using CLUSTAL W (Thompson et al., 1994) and analyzed cladistically using PAUP version 4.0b10 using parsimony optimality criterion and a 1000-replicate bootstrap search using the heuristic search algorithm. All branches with <70% bootstrap support were judged inconclusive and were collapsed.

Figure 2:
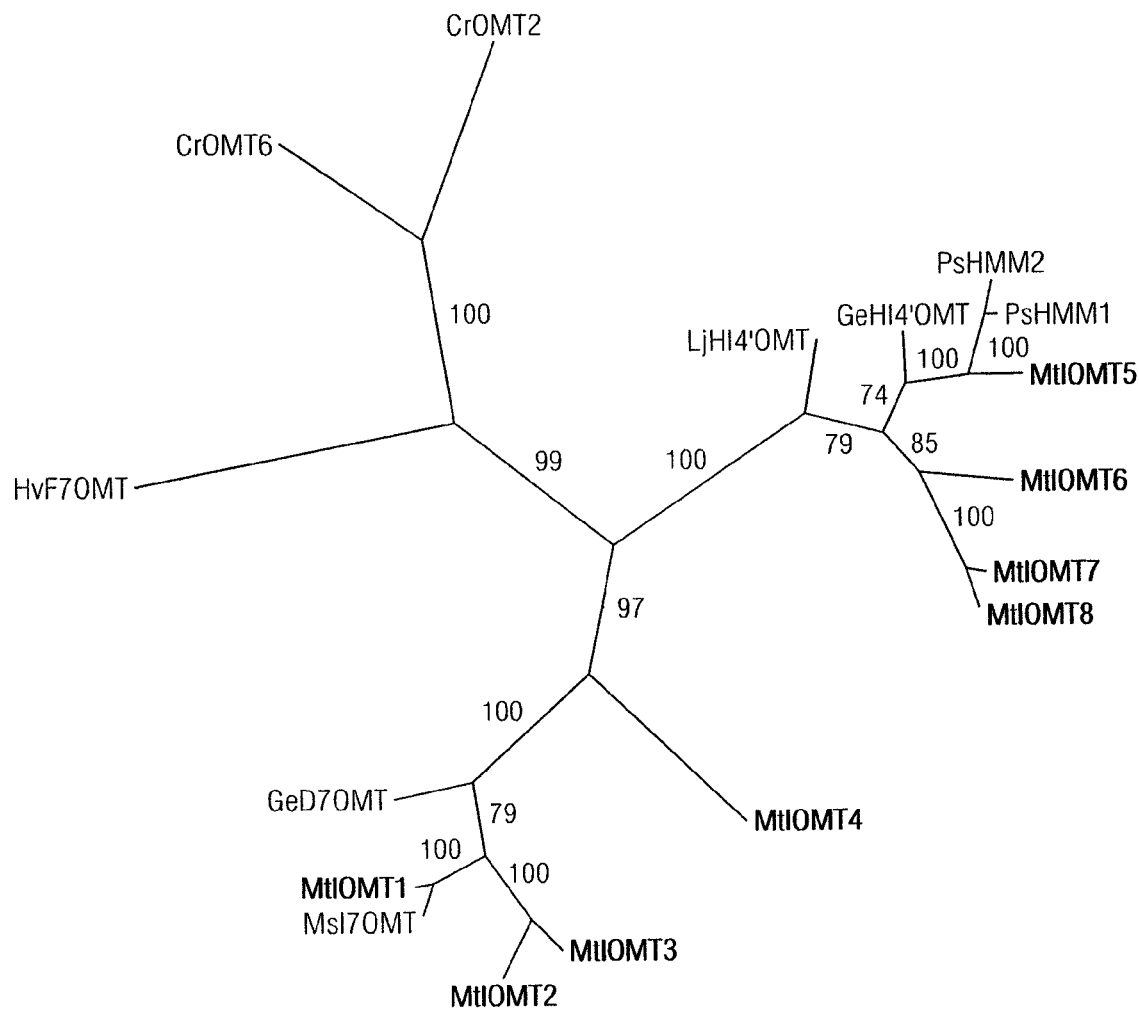
FIG. 2. Relationship tree of (iso)flavonoid OMTs. CrOMT6, *Catharanthus roseus* flavonoid 4'-OMT (GenBank AY343490); CrOMT2, *C. roseus* 3'/5'-flavonol OMT (AY127569); HvF7OMT, *Hordeum vulgare* flavonoid 7-OMT (X77467); GeD7OMT, *G. echinata* daidzein 7-OMT (AB091685); MsI7OMT, *M. sativa* isoflavone 7-OMT (U97125); LjHI4'OMT, *Lotus japonicus* 2-hydroxyisoflavanone 4'-OMT (AB091686); GeHI4'OMT, *G. echinata* 2-hydroxyisoflavanone 4'-OMT (AB091684); PsHMM1, *P. sativum* 6α-hydroxymaackiain 3-OMT (U69554).

Sequence analysis of *M. truncatula* EST libraries using *M. sativa* MsI7OMT (the IOMT8 of He et al., 1998) identified eight putative MtIOMT homologs (here designated as MtIOMT 1-8) with amino acid sequence identities ranging from 51-97% relative to MsI7OMT. Phylogenetic analysis indicated that these putative MtIOMTs cluster into two distinct clades separate from known flavonoid OMTs of the type I plant small molecule OMT family tree (FIG. 2). Protein sequence identity between OMTs from different clades is less than 50%. One clade, designated as the I7OMT clade, includes I7OMT homologs from alfalfa and *Glycyrrhiza echinata* and MtIOMTs 1-4. MtIOMTs 1-3 are 79-89% identical to one another, while MtIOMT4 is 58-59% identical to OMTs within this clade. The second clade includes PsHMM1 and 2, HI4'OMT homologs from *G. echinata* and *Lotus japonicus*, and MtIOMTs 5-8. OMTs within this second clade are 73-76% identical to one another at the amino acid level.

Figure 3:
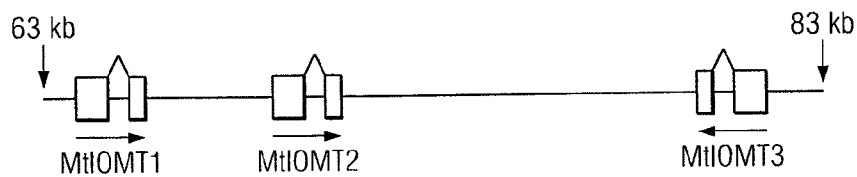
FIG. 3. (a) Genomic organization of MtIOMTs 1-3. Black boxes represent exons and arrows indicate relative orientation. Numbering is in reference to BAC clone AC146549. (b) Location of the single intron in the protein sequence of MtIOMT1 (SEQ ID NO:30), MtIOMT2 (SEQ ID NO:31), and MtIOMT3 (SEQ ID NO:32). Numbers in parentheses represents length of intron in bps. Residues involved in SAM-binding (underlined) and catalysis (bold) are indicated (Zubieta et al., 2001).

Genomic sequences for MtIOMTs 1-3 were obtained by searching the *M. truncatula* ongoing genome sequence web site (www.genome.ou.edu/medicago.html). Genes encoding these three MtIOMTs are located within a 20 kB region on a single BAC clone (AC146549, FIG. 3A). MtIOMT3 is located in the opposite orientation relative to MtIOMT1 and MtIOMT2. All three MtIOMTs have a single intron at the same position in the gene sequence (FIG. 3B), the location of which appears to be highly conserved among plant OMTs (Schroder et al., 2004), while neither intron length nor sequence is conserved. Interestingly, the intron junction neighbors the catalytic His and two residues (Lys and Trp) shown to be important for SAM-binding (Zubieta et al., 2001). These observations suggest that the OMT genes may have arisen from ancient gene duplication events followed by evolution/adaptation.

The *Medicago* IOMT sequences are available in the GenBank database under the accession numbers: AY942159, MtIOMT1; DQ419910, MtIOMT2; DQ419911, MtIOMT3; DQ419912, MtIOMT4; AY942158, MtIOMT5; DQ419913, MtIOMT6; DQ419914, MtIOMT7; DQ419915, MtIOMT8.

B. Substrate Specificities of *Medicago* IOMTs

Figure 14:
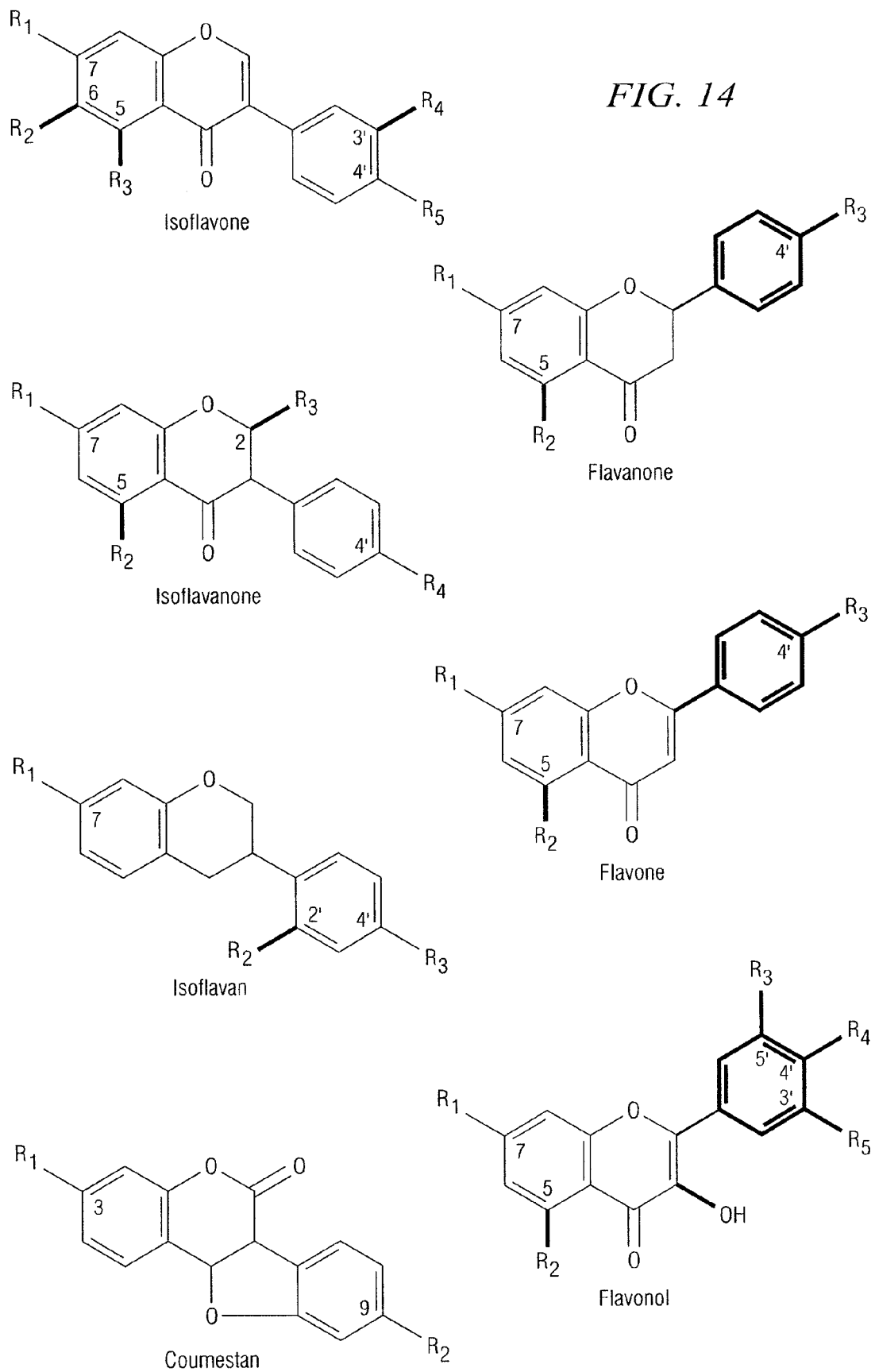
FIG. 14. Chemical structures of selected flavonoid and isoflavonoid compounds.

Sequence analysis of the MtIOMT EST clones revealed that most were full-length. In the case of MtIOMT2, the full length open reading frame was obtained by PCR from root cDNA using primers based on the previously determined genomic sequence. Hexa-histidine-tagged MtIOMTs were expressed in *E. coli*, purified by Ni-affinity chromatography, and tested for enzymatic activity using a range of flavonoid and isoflavonoid compounds as potential substrates (e.g. Table 2; FIG. 14 shows the basic ring structures and numberings of the different compound classes). MtIOMT8 was insoluble upon expression in *E. coli* and therefore not pursued further. For comparison, previously characterized alfalfa MsI7OMT (alfalfa IOMT8, He and Dixon, 1996; He et al., 1998) is included. This enzyme was reported to have highest activity with 6,7,4'-trihydroxyisoflavone (136% of the activity with daidzein) and little activity with the 4'-methoxyisoflavones formononetin and biochanin A (He et al., 1998).

TABLE 2

Substrates analyzed with recombinant IOMTs in the present work

| Substrate | $R_1$ | $R_2$ | $R_3$ | $R_4$ | $R_5$ |
|---|---|---|---|---|---|
| Isoflavone | | | | | |
| 6,7,4'-trihydroxyisoflavone | OH | OH | H | H | OH |
| 6,7-dihydroxy,4'-methoxyisoflavone | OH | OH | H | H | $OCH_3$ |
| 7,3',4'-trihydroxyisoflavone | OH | H | H | OH | OH |
| Daidzein | OH | H | H | H | OH |
| Genistein | OH | H | OH | H | OH |
| Glycitein | OH | $OCH_3$ | H | H | OH |

TABLE 2-continued

Substrates analyzed with recombinant IOMTs in the present work

| Substrate | R₁ | R₂ | R₃ | R₄ | R₅ |
|---|---|---|---|---|---|
| Isoflavanone | | | | | |
| 2,7,4'-trihydroxyisoflavanone | OH | H | OH | OH | |
| Dihydrodaidzein | OH | H | H | OH | |
| Isoflavan | | | | | |
| Vestitol | OH | OH | OCH₃ | | |
| Coumestan | | | | | |
| Coumestrol | OH | OH | | | |
| Flavanone | | | | | |
| Liquiritigenin | OH | H | OH | | |
| Naringenin | OH | OH | OH | | |
| Flavone | | | | | |
| Apigenin | OH | H | OH | | |
| 5,7,4'-trihydroxyflavone | OH | OH | OH | | |
| Flavonol | | | | | |
| Myricetin | OH | OH | OH | OH | OH |

MtIOMTs in the MsI7OMT clade prefer isoflavone substrates, which adopt a relatively flat conformation, while those in the HI4'OMT clade prefer substrates with chiral centers (isoflavanones or isoflavans) with a bent molecular conformation (Table 3). The ability of the isoflavanone dihydrodaidzein to adopt a relatively flat conformation as modeled in the structure of MtIOMT2 or a sharply bent conformation similar to that observed for 2,7,4'-trihydroxyisoflavanone in the structure of MtIOMT5 (Liu et al., 2005) may explain why this compound could be methylated by both groups of MtIOMTs. The similar conformations of flavanones and isoflavanones, both with chiral centers at C2 and/or C3, may explain why MtIOMT5 and MtIOMT7 catalyzed methylation of liquiritigenin and naringenin, in addition to isoflavanone.

MtIOMT1 and MtIOMT2 both display strict 7-position specificity for isoflavones and in this regard are more similar to each other than to MtIOMT3, although MtIOMT1 and MtIOMT2 (79% identical) share a higher level of identity with MtIOMT3 (82 and 89%, respectively). The presence of an intron at a conserved location within the C-terminal regions of OMTs (Schroder et al., 2004), close to residues involved in SAM binding and catalysis, suggests that variable splicing at intron-exon junctions may contribute to the diversification of OMT substrate-binding and catalysis during the evolution and selection of related plant OMTs.

C. Structural Basis for IOMT Substrate Specificity

The most frequent substitutions of active site residues in the MtI7OMT clade of plant OMTs were at those amino acid positions forming the bottom and back wall of the substrate binding pocket. These include Tyr 25, Asn 310, Met 311, and Tyr 127 (numbered as in MsI7OMT), which were shown previously to be critical residues for either hydrogen bond formation or van der Waal's interactions with phenolic substrates in the structure of MsI7OMT complexed with isoformononetin. Substitutions of these residues in MtIOMT2 resulted in a change in the shape of the MtIOMT2 binding pocket leading to fewer spatial restraints on substrate recognition and binding, thus explaining the broader substrate- and regio-specificities of MtIOMT2 relative to MsI7OMT and MtIOMT1.

In the homology model of MtIOMT3, hypotheses regarding regio-specificity were governed by structural restraints imposed by the bottom half of the catalytic cavity that served to orient substrates with ortho-substituted groups for SAM-mediated methylation. Thus, when daidzein, which lacks ortho-substituted groups proximal to either the 7- or 4'-hydroxyl groups, was used as an in vitro substrate, both 7- and 4'-O-methylated products were observed.

The gross alteration in the shape of the substrate binding pocket of MtIOMT4 anticipated based upon the computed homology model suggests why this IOMT has only minimal activity with the substrates currently tested in vitro. Nevertheless, while these homology models provide explanations for why certain substrates may not be efficiently methylated by MtIOMT4, this "low resolution" information can not anticipate subtle changes in the shape and chemical properties of the catalytic surface and thus is not sufficient to reliably predict the identity of the true substrates for this divergent OMT.

MtIOMTs within the HI4'OMT clade also displayed a number of amino acid changes in their phenolic substrate binding site compared to MsIOMT7. The structure of MtIOMT5 in an "open" conformation has been solved (Liu et al., 2005) but, due to the large distance between the phenolic substrate binding pocket, the SAM binding cleft, and the catalytic His in the solved structure, it was not possible to reliably auto-dock the phenolic substrates to the structural model of other MtIOMTs within this clade. Additional structural data for the other HI4'OMT clade members is necessary for a more concrete understanding of their respective substrate specificities.

In the experimentally determined crystal structure of MtIOMT5 with 2,7,4'-trihydroxyisoflavanone, the 2-hydroxyl group forms hydrogen bonds with the side chain of Tyr 25 and a neighboring water molecule that serves to anchor the substrate in the binding cavity (Liu et al., 2005). The importance of this 2-hydroxyl moiety in limiting methylation to the 4'-position was confirmed by the presence of 4'-O-methyl, 7-O-methyl, and 7,4'-di-O-methylated products in reactions with dihydrodaidzein (7,4'-dihydroxyisoflavanone), which lacks a 2-hydroxyl group, while only 4'-O-methylated product is observed in reactions with 2,7,4'-trihydroxyisoflavanone (FIGS. 10I, 10J).

The discovery of the 2,7,4'-trihydroxyisoflavanone OMT led to a new hypothesis for the biosynthesis of 4'-O-methylated isoflavonoids (Akashi et al., 2003), and strongly questioned the earlier hypothesis for 4'-O-methylation of 2,7,4'-trihydroxyisoflavanone by an enzyme that also exhibited 7-OMT activity in vitro (Liu and Dixon, 2001). Several of the enzymes currently studied exhibited both 7- and 4'-OMT activities, depending on the substrate; however, only MtIOMT1 (7-position specific for isoflavones) and MtIOMT5 (4'-specific for 2-hydroxyisoflavanone) were strongly co-induced with IFS based on RT-PCR results. Microarray data also confirmed the co-expression pattern of MtIOMT5 with IFS genes. The potential physiological function of the dual regiospecificity of MtIOMTs 2-6 with alternative substrates (e.g. dihydrodaidzein) remains unclear.

D. Annotation of MtIOMTs Based on Transcript Expression Profiling

The expression patterns of MtIOMT gene family members, either in healthy or infected plant tissues, or in cell cultures responding to yeast elicitor or methyl jasmonate, provided strong indirect evidence for or against specific gene annotations. For example, MtIOMT5 was co-expressed with IFS in all tissues/treatments studied, consistent with its functioning as a true 2,7,4'-trihydroxyisoflavanone OMT, a conclusion corroborated by its substrate preference in vitro. However, the closely related MtIOMT6 gene, although expressed in healthy roots, was not co-expressed with IFS; indeed, MeJA massively induced MtIOMT6 and MtIOMT7 but down-regulated IFS genes. Even though MtIOMT6 is 97% identical to true 2,7,4'-trihydroxyisoflavanone OMT, this annotation would appear to be incorrect, as further indicated by in vitro analysis. MtIOMT1 and MtIOMT3 are induced in Phoma-infected leaves. MtIOMT1 is also induced by yeast elicitor and MeJA in cell cultures. In contrast, MtIOMT4 is massively induced by YE (nearly 250-fold) but down-regulated by MeJA. Clearly, these four genes annotated as isoflavone 7-OMTs most likely encode enzymes with different biochemical functions. Unfortunately, analysis of substrate specificities in vitro fails to clarify these functions in relation to the known natural products of M. truncatula (see below).

E. MtIOMT1

MtIOMT1 is 97% identical to MsI7OMT and has nearly identical substrate specificity (Table 3). Activity is primarily limited to planar isoflavones, although surprisingly the non-planar isoflavanone dihydrodaidzein also undergoes methylation. MtIOMT1 (and MsI7OMT) have highest activity with the partially methylated 6-methoxyisoflavone glycitein (a natural product of soybean) among the various substrates tested. Relative initial activity at a saturating concentration of glycitein is more than 2-fold higher than with 6,7,4'-trihydroxyisoflavone or 7,3',4'-trihydroxyisoflavone, and 5-fold higher than with daidzein. Methylation of the 4'-hydroxyl group of 6,7,4'-trihydroxyisoflavone drastically reduces activity by more than 80-fold (compare activity with 6,7-dihydroxy-4'-methoxyisoflavone to that with 6,7,4'-trihydroxyisoflavone). The only significant difference in substrate specificity between MtIOMT1 and MsI7OMT is for genistein. MsI7OMT has lower activity with genistein than with daidzein, whereas the activity of MtIOMT1 with genistein is more than 2-fold higher than with daidzein (and comparable to the activity with 6,7,4'-trihydroxyisoflavone and 7,3',4'-trihydroxyisoflavone).

TABLE 3

Activities of purified MtIOMTs against a range of phenolic substrates[a]

| Substrate | MtIOMT1 | MtIOMT2 | MtIOMT3 | MtIOMT4 | MtIOMT5 | MtIOMT6 | MtIOMT7 | MsI7OMT |
|---|---|---|---|---|---|---|---|---|
| Isoflavone | | | | | | | | |
| 6,7,4'-trihydroxyisoflavone | 43.9 | 35.3 | 100 | 0 | 0 | 0 | 0 | 51.8 |
| 6,7-dihydroxy,4'-methoxyisoflavone | ≤1 | 0 | 0 | 0 | 0 | 0 | 0 | ≤1 |
| 7,3',4'-trihydroxyisoflavone | 40.8 | 43.1 | 52.9 | 0 | 0 | 0 | ≤1 | 47.1 |
| Daidzein | 20.6 | 100 | ≤1 | 0 | 0 | 0 | 0 | 21.6 |
| Genistein | 49.2 | 61 | 73.7 | 0 | 0 | 0 | 0 | 15 |
| Glycitein | 100 | 38.9 | 51.6 | 0 | 0 | 0 | ≤1 | 100 |
| Isoflavanone | | | | | | | | |
| 2,7,4'-trihydroxyisoflavanone | ND[c] | ND[c] | ND[c] | ND[c] | 100 | ND[c] | 24.8 | ND[c] |
| Dihydrodaidzein | 15.6 | 70.1 | 49.4 | 0 | 7.9 | 100 | 84.1 | 12.8 |
| Isoflavan | | | | | | | | |
| Vestitol | 0 | ≤1 | 0 | 43.8 | ≤1 | 66.2 | 3.4 | 0 |
| Coumestan | | | | | | | | |
| Coumestrol | 0 | ≤1 | 0 | 100 | 0 | 0 | 1.5 | 0 |
| Flavanone | | | | | | | | |
| Liquiritigenin | 0 | ≤1 | 0 | 0 | ≤1 | 0 | 42.2 | 0 |
| Naringenin | 0 | ≤1 | 0 | 0 | ≤1 | 0 | 100 | 0 |
| Flavone | | | | | | | | |
| Apigenin | 0 | 0 | 0 | 0 | 0 | 0 | 0 | 0 |
| 7,4'-dihydroxyflavone | 0 | ≤1 | 0 | 0 | 0 | 0 | 0 | 0 |
| Flavonol | | | | | | | | |
| Myricetin | 0 | 0 | 0 | 0 | 0 | 0 | 0 | 0 |
| pkat/mg[b] | 3646.7 | 930.2 | 7.4 | 2.6 | 4189.6 | 6.9 | 198.8 | 2742.0 |

[a]Relative activity at 50 μM S-adenosyl methionine and 100 μM acceptor substrate. Reactions were run for several different time periods to ensure reaction rates were in the linear portion with respect to time, and values are normalized with the conversion rate for the most converted substrate as 100%.
[b]Specific activity at 100%
[c]Not determined-initial activity screens revealed very low or no activity.

To determine the regio-specificity of methylation, reaction products were subjected to HPLC separation and identified by comparison to available standards, or subjected to tandem MS analysis (FIGS. 10-13; Table 4)

TABLE 4

Quantification of methylated products in reactions with dihydrodaidzein

| | % 4'-Methylated | % 7-Methylated | % Dimethylated | Ratio 4'/7-methylated |
|---|---|---|---|---|
| MtIOMT1 | 0 | >99 | <1 | 0 |
| MtIOMT2 | 33 | 66 | <1 | 0.5 |
| MtIOMT3 | 92 | 8 | 0 | 11.4 |
| MtIOMT4 | 0 | 0 | 0 | 0 |
| MtIOMT5 | 44 | 25 | 31 | 1.7 |
| MtIOMT6 | 14 | 38 | 48 | 0.4 |
| MtIOMT7 | 35 | 3 | 62 | 10.5 |

Only 7-O-methylated products were observed for MtIOMT1 and MsI7OMT. In reactions with 2,7,4'-trihydroxyisoflavanone, a minor peak was observed eluting slightly before the peak corresponding to 2,7-dihydroxy, 4'-methoxyisoflavanone (FIG. 10J). It is possible that this compound is the 7-O-methylated isoflavanone, since isoformononetin (7-O-methyl daidzein) is also detected in reactions with 2,7,4'- trihydroxyisoflavanone. Isoformononetin may arise either by methylation of daidzein formed from the spontaneous dehydration of the unstable 2,7,4'-trihydroxyisoflavanone, or via spontaneous dehydration of 2,4'-dihydroxy-7-methoxyisoflavanone.

F. MtIOMT2

Figure 13:
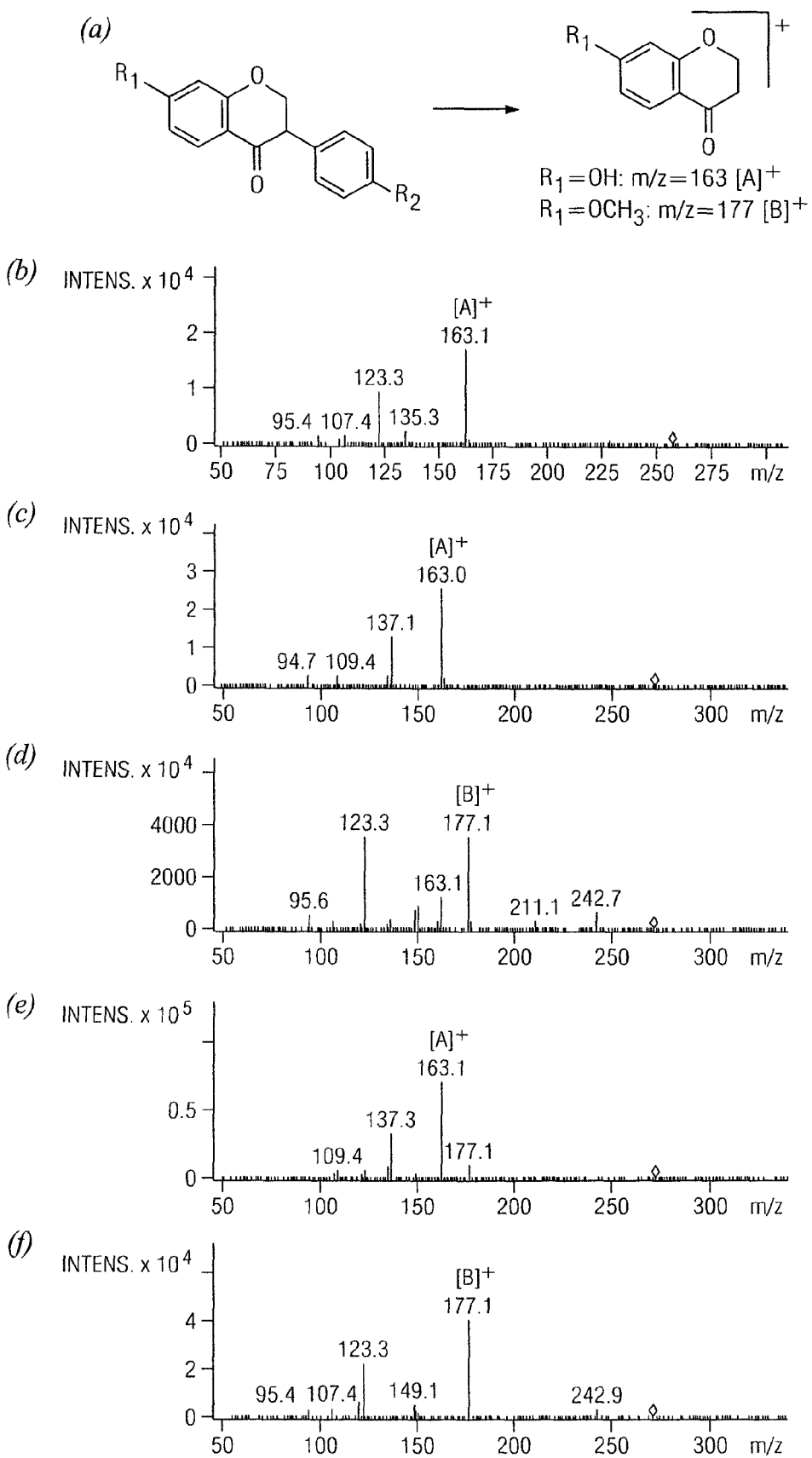
FIG. 13. Positive ion LC/ESI/MSMS spectra of dihydrodaidzein reaction products. (a) Proposed fragmentation scheme. (b) Dihydrodaidzein precursor ion is m/z 257. (c-d) MtIOMT5 methylated products, precursor ion is m/z 271. (e-f) MtIOMT7 methylated products, precursor ion is m/z 271. (g-h) MtIOMT6 methylated products, precursor ion is m/z 271. (i) MtIOMT1 methylated product, precursor ion is m/z 271. (j-k) MtIOMT2 methylated products, precursor ion is m/z 271. (l-m) MtIOMT3 methylated products, precursor ion is m/z 271.
Figure 13:
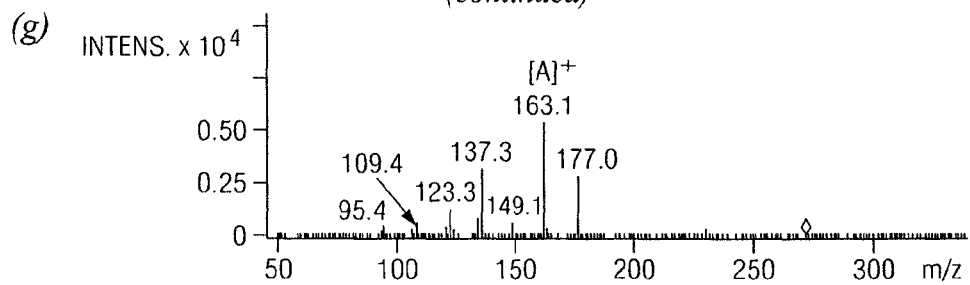
Figure 13:
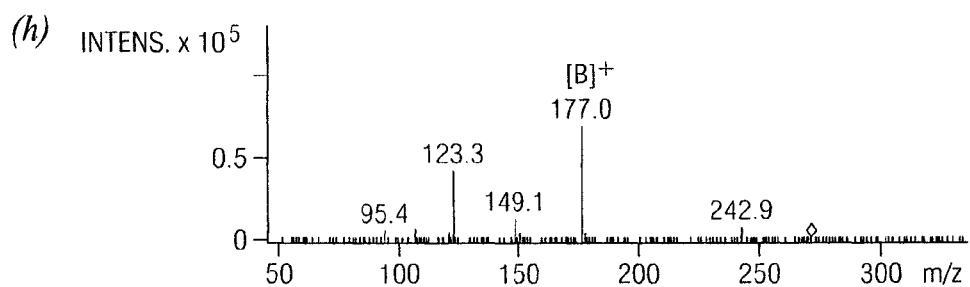
Figure 13:
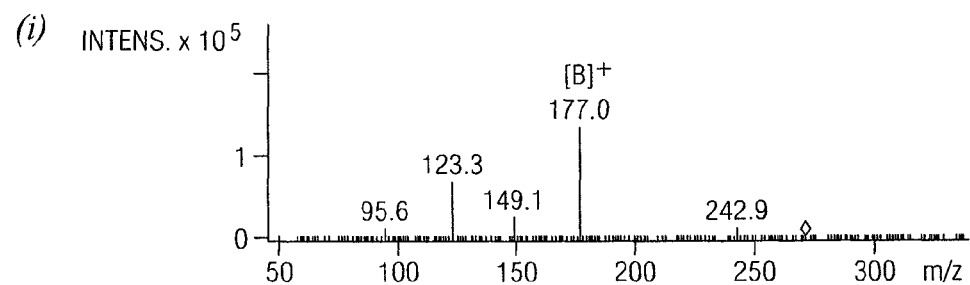
Figure 13:
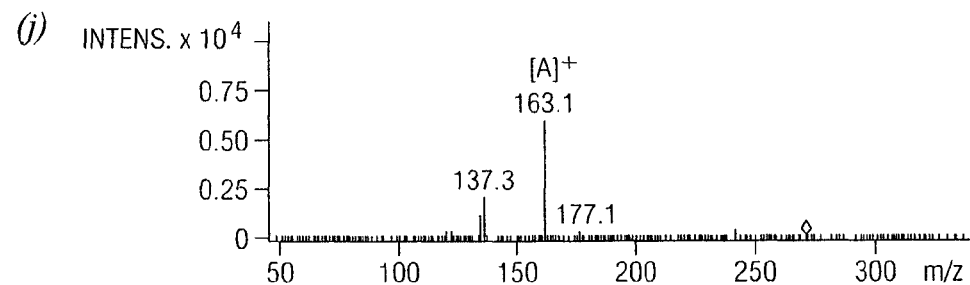
Figure 13:
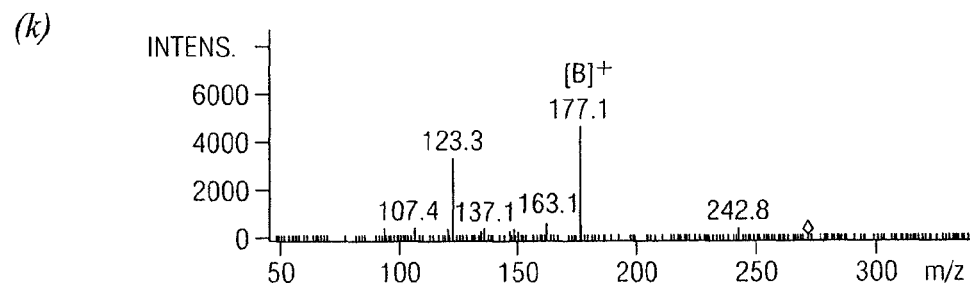
Figure 13:
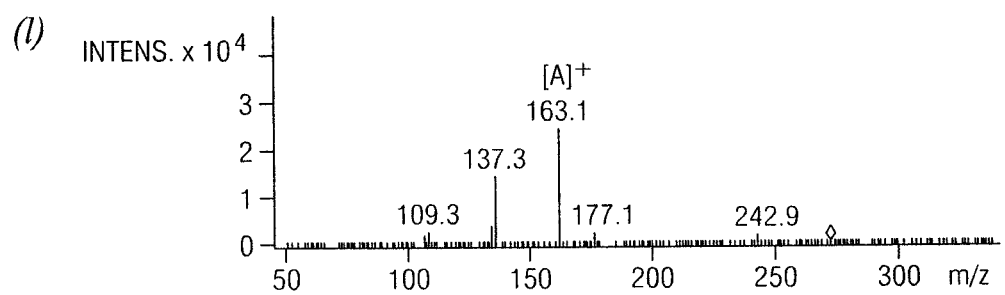
Figure 13:
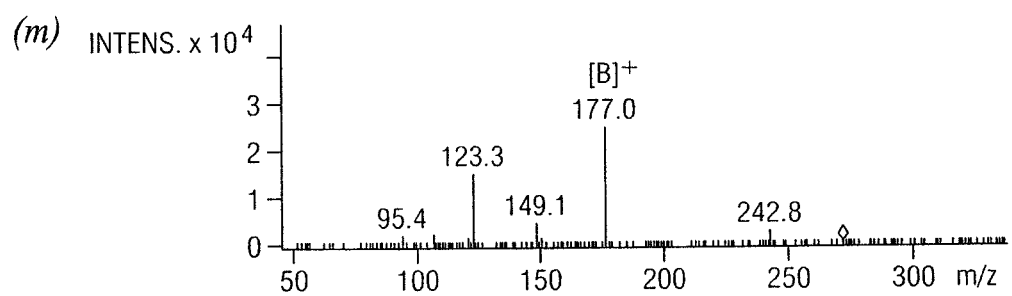

MtIOMT2 methylates the same isoflavones as MtIOMT1 and MsI7OMT, but exhibits a different overall pattern of substrate specificity (Table 3). The best substrate for MtIOMT2 is daidzein, followed by dihydrodaidzein and genistein (70.1 and 61% of daidzein activity, respectively). Comparable activity is observed for 6,7,4'-trihydroxyisoflavone, 7,3',4'-trihydroxyisoflavone, and glycitein (35-43.1% of daidzein activity). MtIOMT2 additionally methylates vestitol, coumestrol, liquiritigenin, and naringenin, although with low efficiency. As with MsI7OMT and MtIOMT1, methylation occurs on the 7-position of isoflavones, although coumestrol is methylated on the 9-position (equivalent to the 4'-position of isoflavone) (FIG. 10). Two peaks were observed in reactions with liquiritigenin and naringenin; reaction products with liquiritigenin were identified as the 7-O-methylated and 7,4'-di-O-methylated products. Similarly, both 7 and 4'-O-methylated products are observed in reactions with dihydrodaidzein (FIG. 13, Table 4). The methylation position on vestitol could not be determined. Minor unidentified peaks were observed in reactions with 2,7,4'-trihydroxyisoflavanone (FIG. 10J).

G. MtIOMT3

Figure 4:
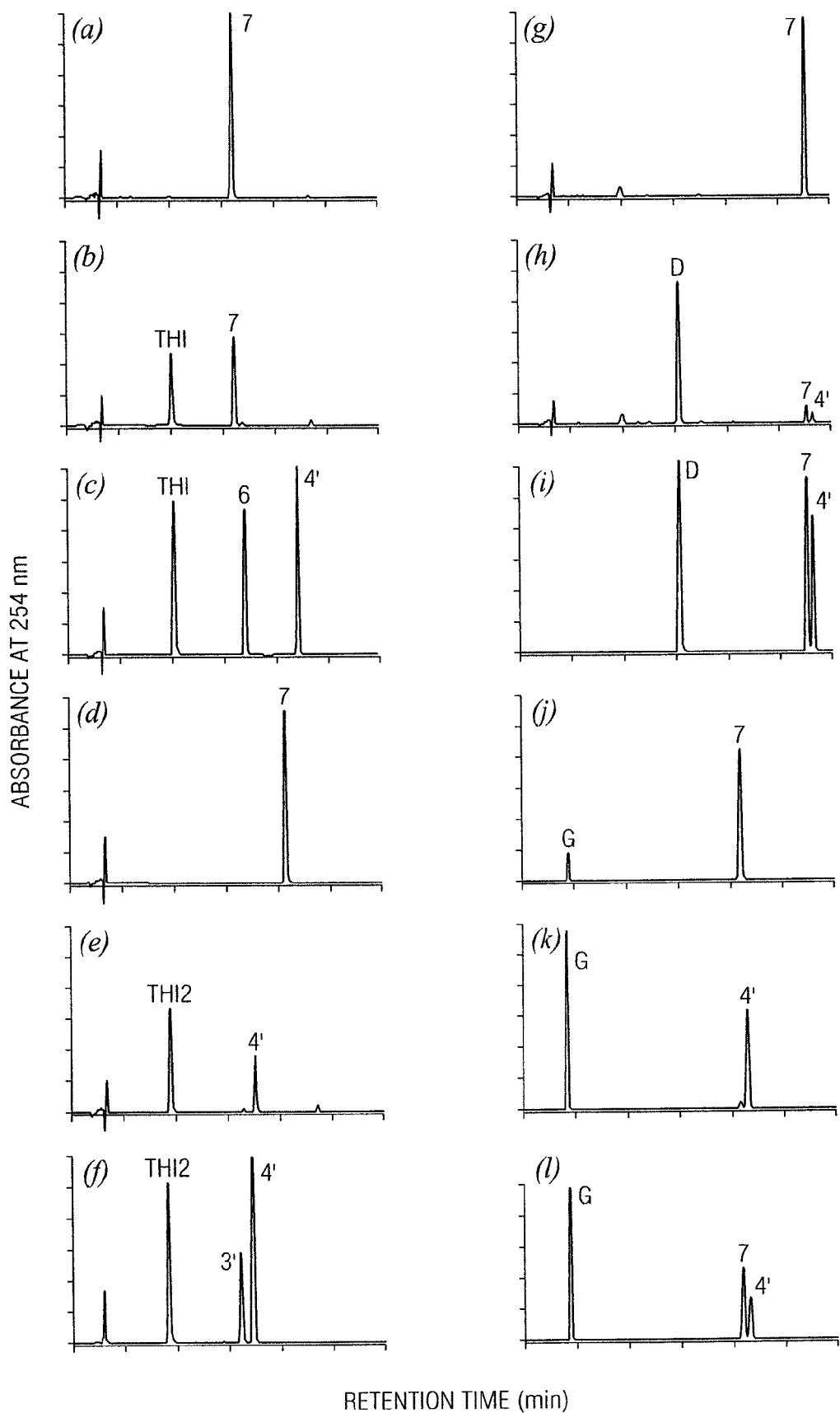
FIG. 4. HPLC chromatograms of reaction products of MtIOMT1 (a, d, g, j) and MtIOMT3 (b, e, h, k) with 6,7,4'-trihydroxyisoflavone (a, b), 7,3',4'-trihydroxyisoflavone (d,e), daidzein (g,h), and genistein (j,k) as substrates. Standards are shown in panels c, f, i, l and methylated standards are labeled according to the position of the methyl group. (c) THI, 6,7,4'-trihydroxyisoflavone; 6, glycitein; 4',6,7-dihydroxy, 4'-methoxyisoflavone. (f) THI2, 7,3',4'-trihydroxyisoflavone; 3',3'-methoxydaidzein; 4', calycosin. (i) D, daidzein; 7, isoformononetin; 4', formononetin. (1) G, genistein; 7, prunetin; 4', biochanin A.

MtIOMT3 methylates the same isoflavone substrates as MsI7OMT, MtIOMT1, and MtIOMT2, and both 7- and 4'-O-methylated products are observed, depending on the substrate used (FIG. 4). For comparison, FIG. 4 also includes HPLC traces for reactions with MtIOMT1. MtIOMT3 has highest activity with 6,7,4'-trihydroxyisoflavone, followed by genistein, 7,3',4'-trihydroxyisoflavone, glycitein, and dihydrodaidzein (Table 3). Both 6,7,4'-trihydroxyisoflavone and glycitein undergo methylation on the 7-position (FIG. 4b, FIGS. 10A, 10E), whereas the major reaction products for 7,3',4'-trihydroxyisoflavone and genistein are the corresponding 4'-methoxy isoflavones, calycosin and biochanin A (FIGS. 4e, 4k). Minor 7-O-methyl (isoformononetin) and 4'-O-methyl (formononetin) products are observed with daidzein (FIG. 4h). Primarily 4'-O-methylated product is observed in reactions with dihydrodaidzein (FIG. 13, Table 4), whereas no products are detected in reactions with 2,7,4'-trihydroxyisoflavanone (FIG. 10J).

H. MtIOMT4

Figure 10A:
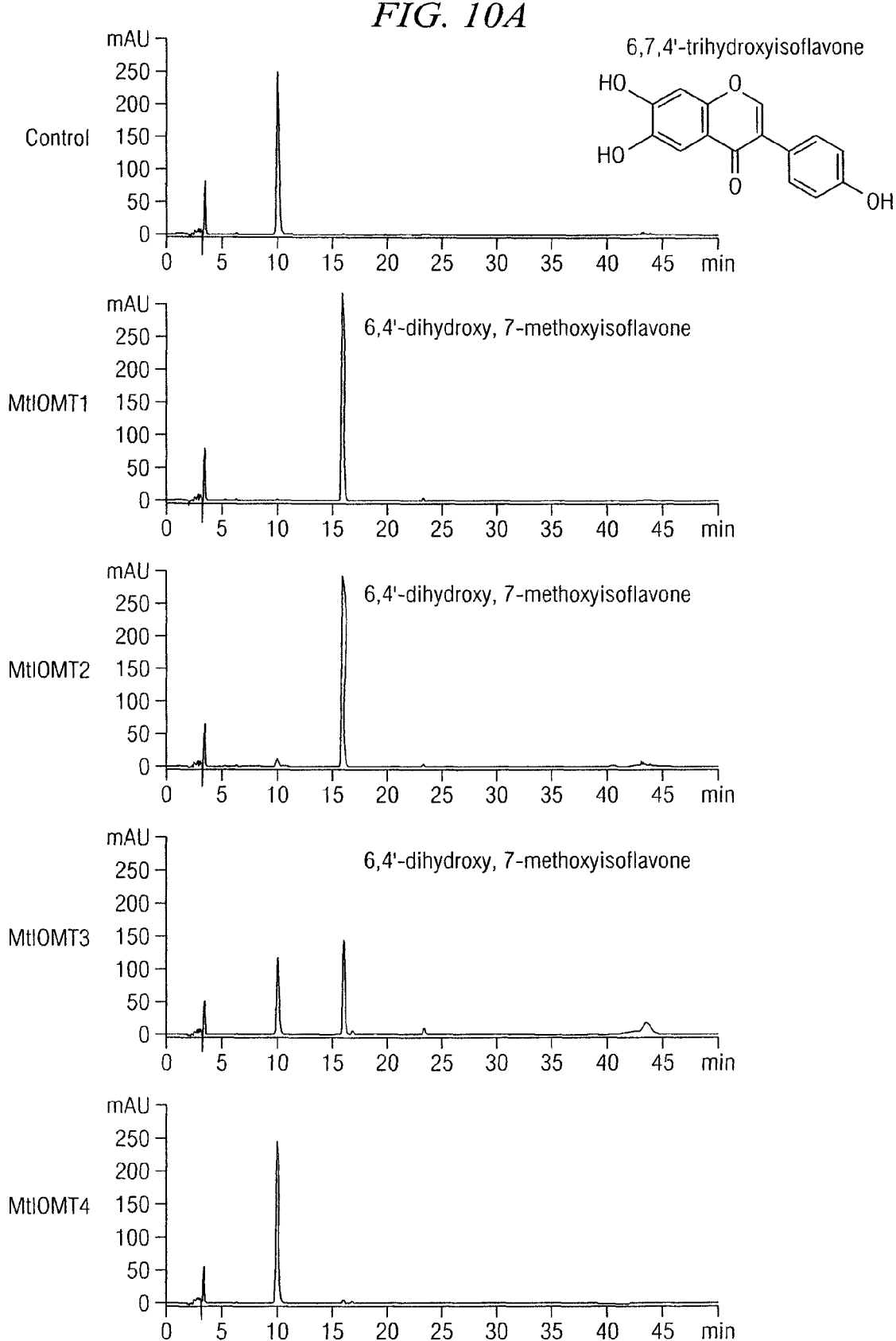
FIG. 10. HPLC chromatograms of MtIOMT reaction products; (a) reaction products with 6,7,4'-trihydroxyisoflavone; (b) reaction products with 6,7-dihydroxy, 4'-methoxyisoflavone; (c) reaction products with 7,3'4'-trihydroxyisoflavone; (d) reaction products with daidzein; (e) reaction products with genistein; (f) reaction products with glycitein; (g) reaction products with coumestrol; (h) reaction products with vestitol; (i) reaction products with dihydrodaidzein; (j) reaction products with 2,7,4'-trihydroxyisoflavanone; (k) reaction products with liquiritigenin; (l) reaction products with naringenin; (m) reaction products with apigenin; (n) reaction products with 7,4'-dihydroxyflavone.
Figure 10A:
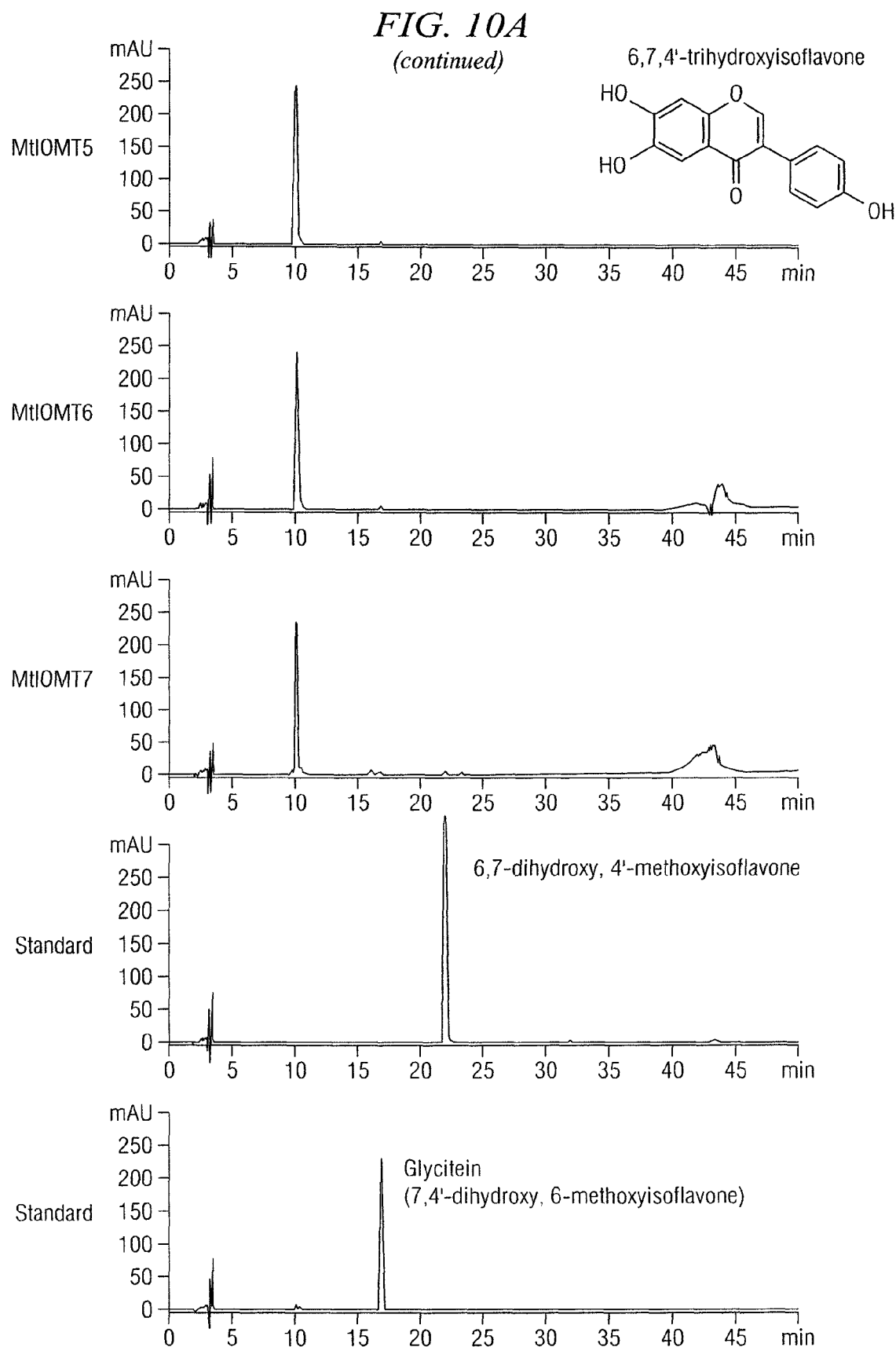
Figure 10B:
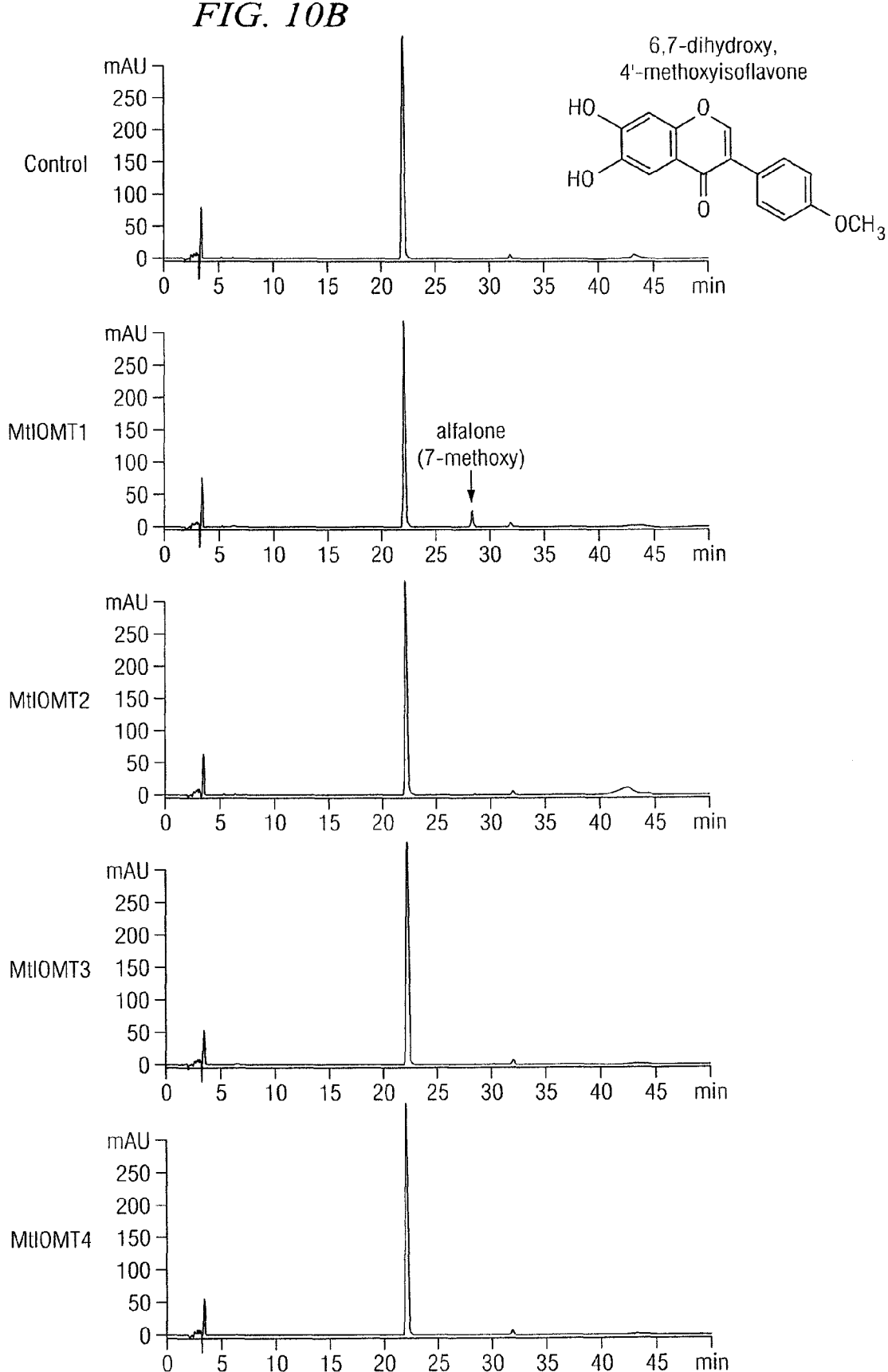
Figure 10B:
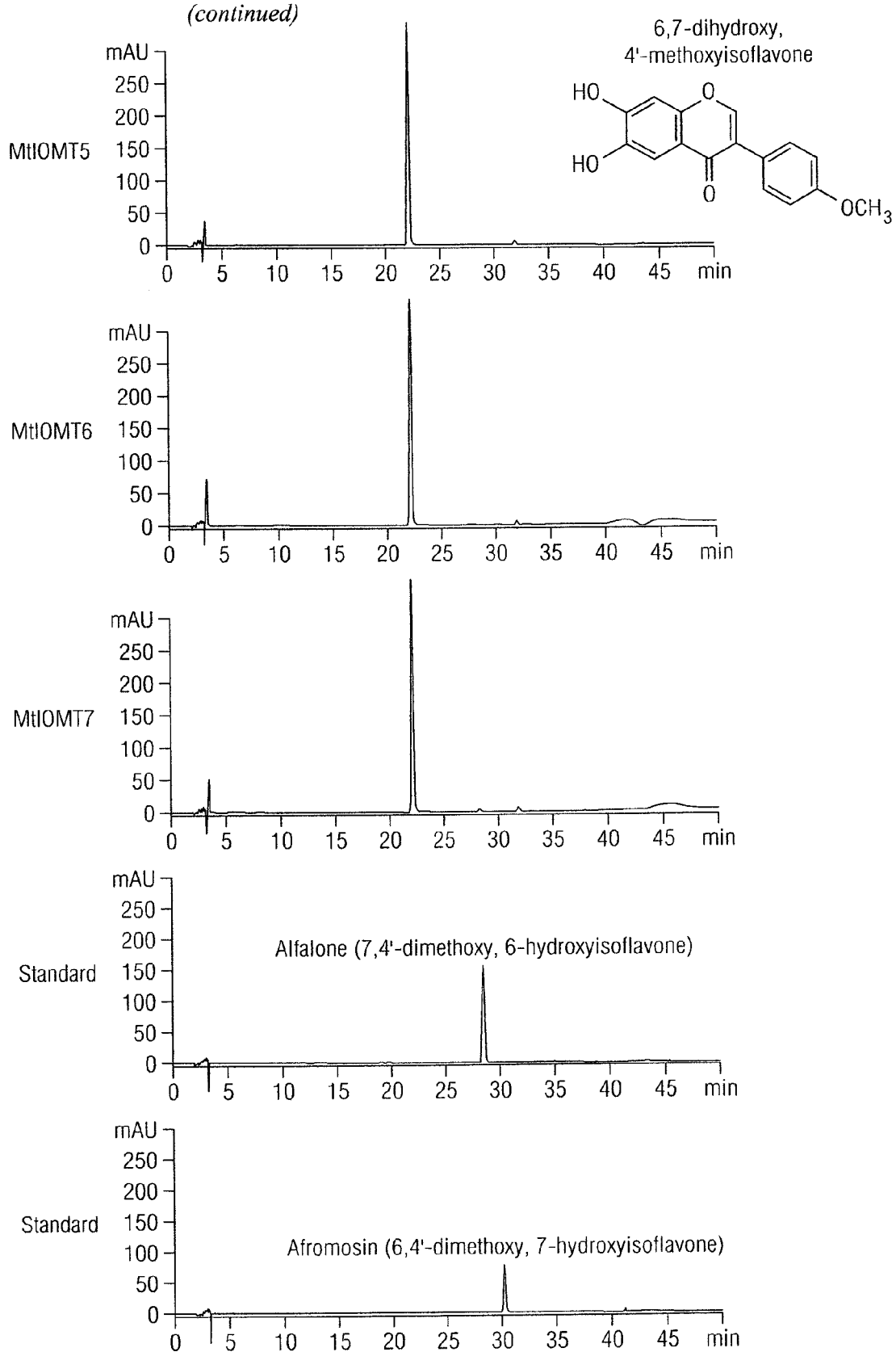
Figure 10C:
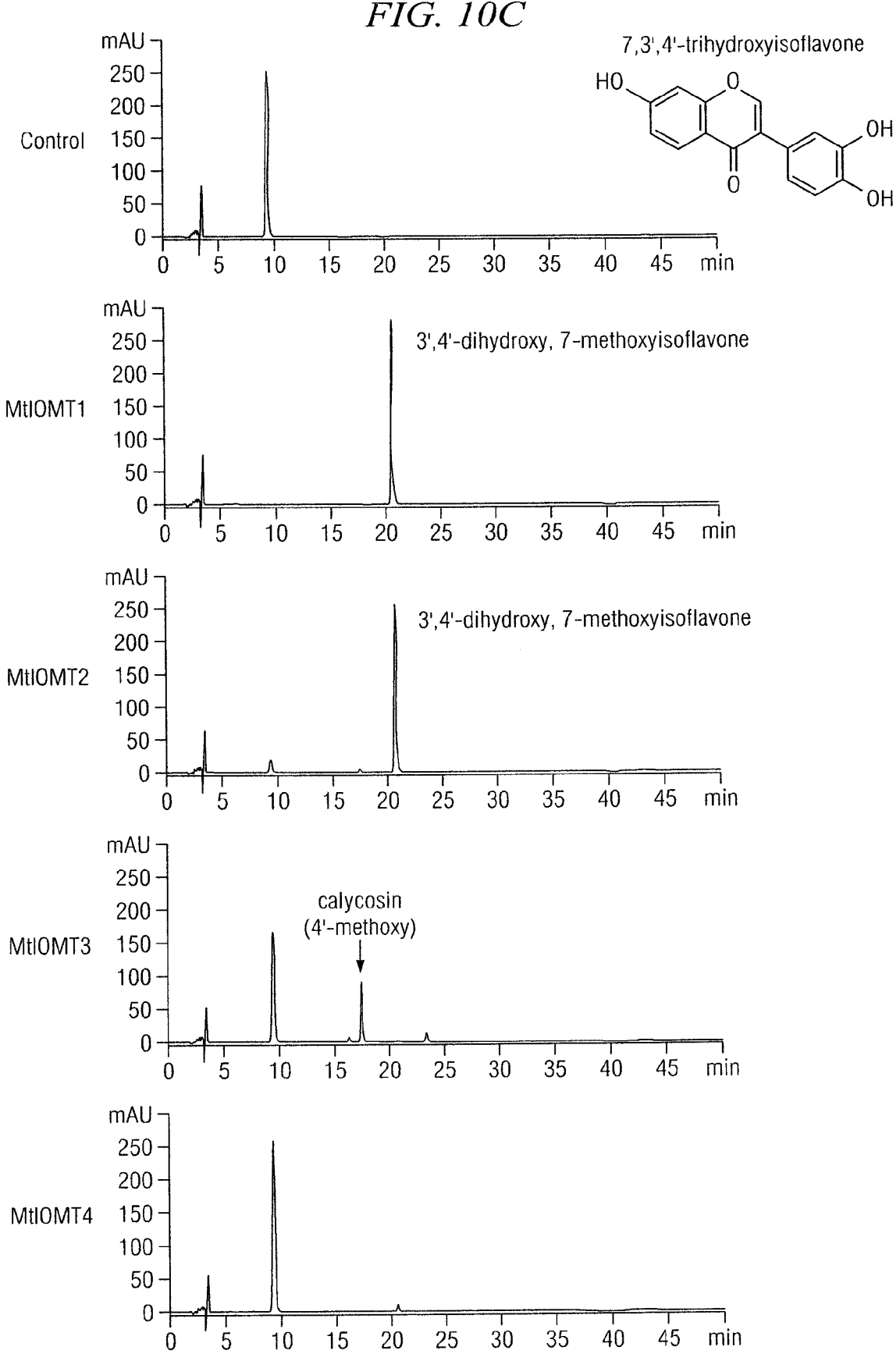
Figure 10C:
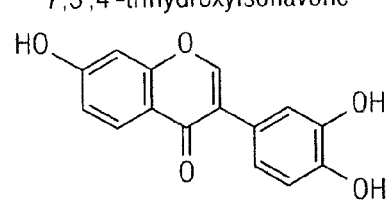
Figure 10C:
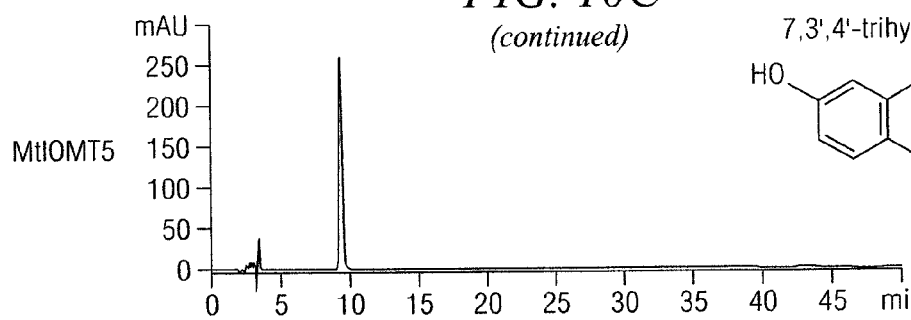
Figure 10C:
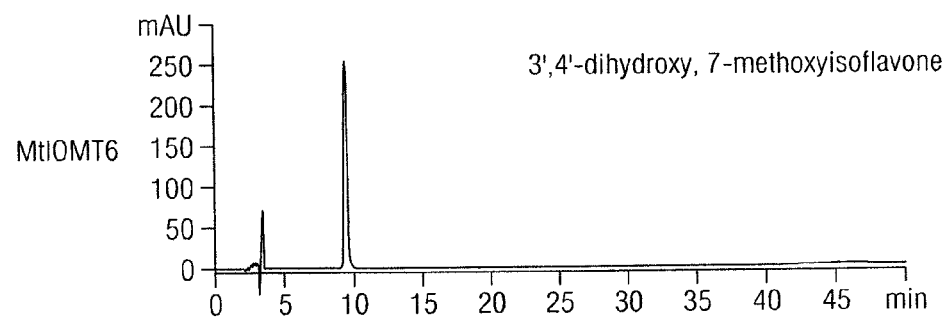
Figure 10C:
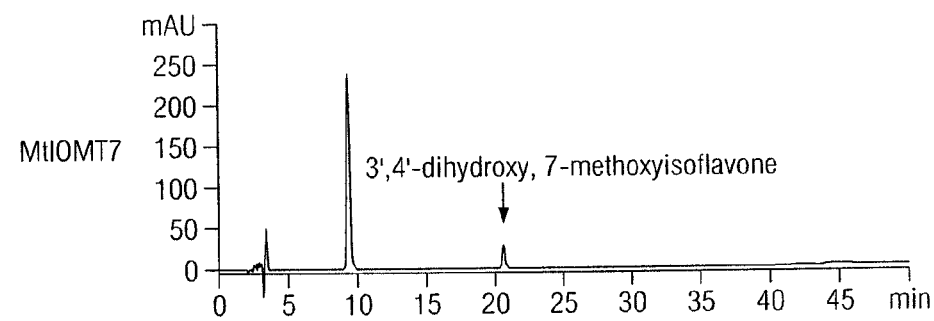
Figure 10C:
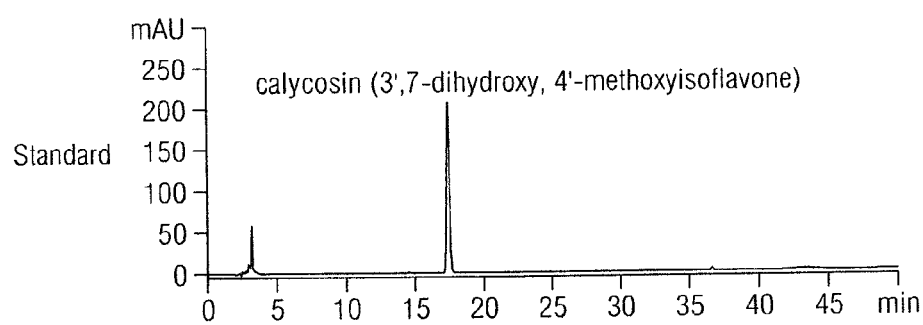
Figure 10C:
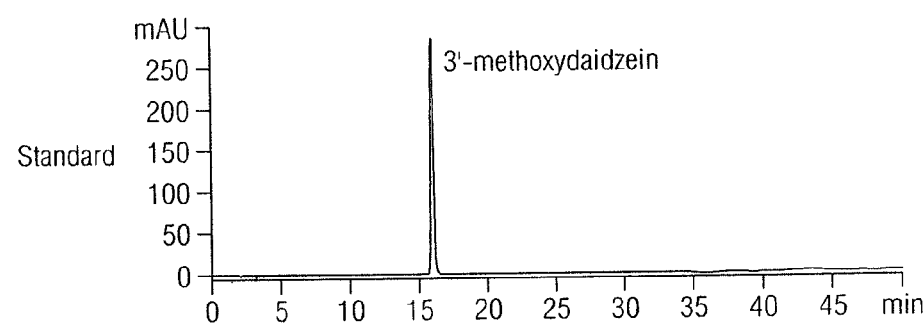
Figure 10D:
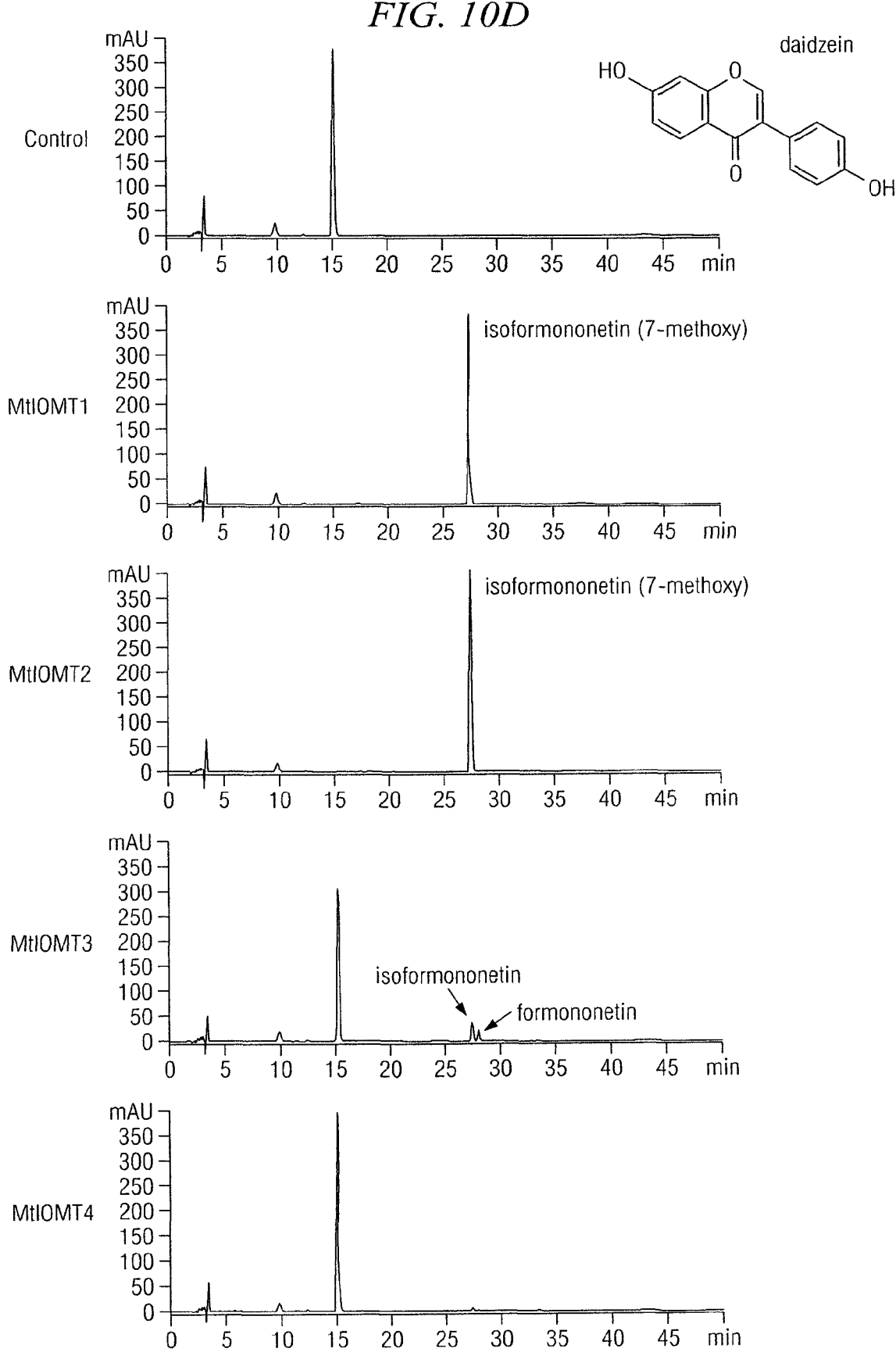
Figure 10D:
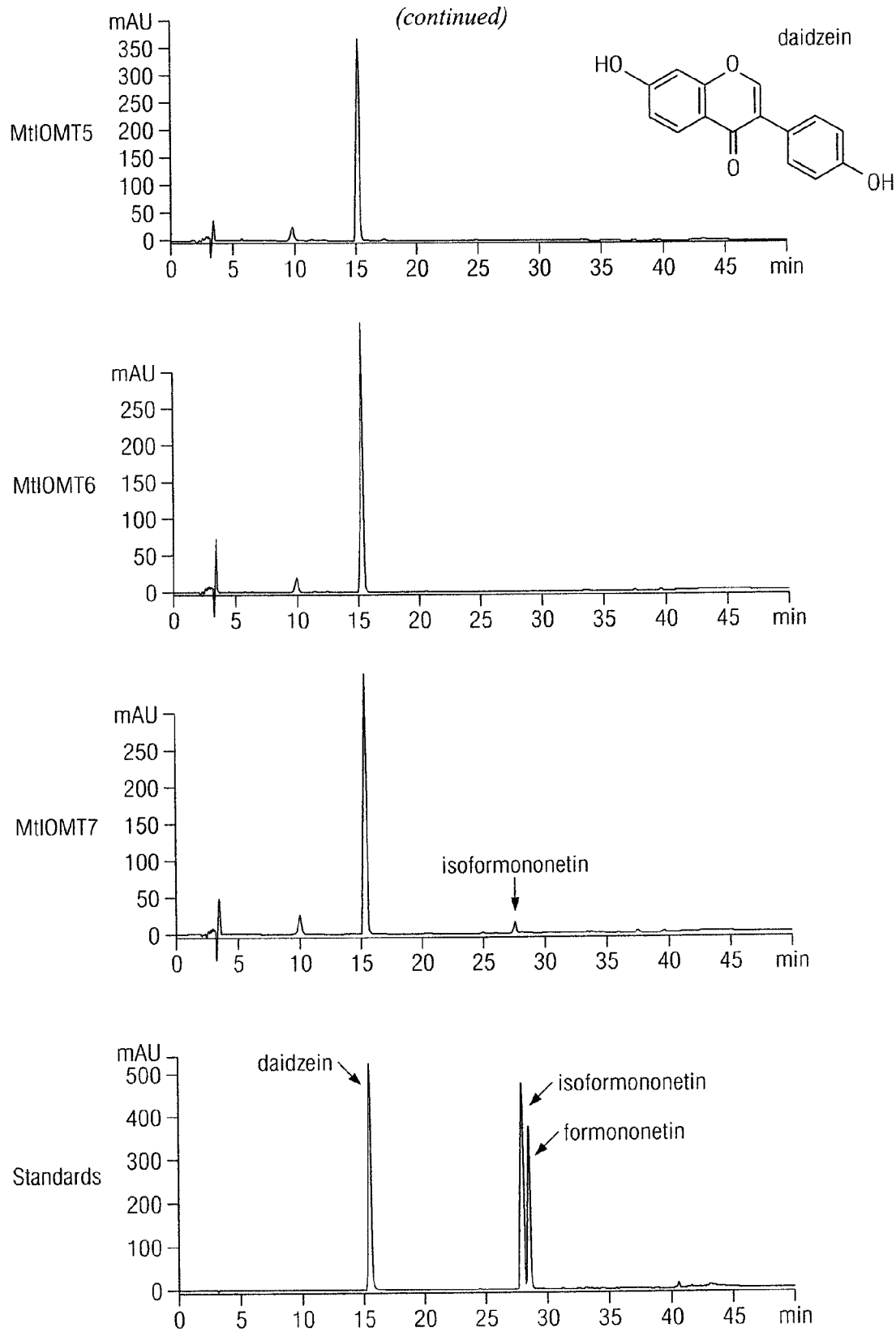
Figure 10E:
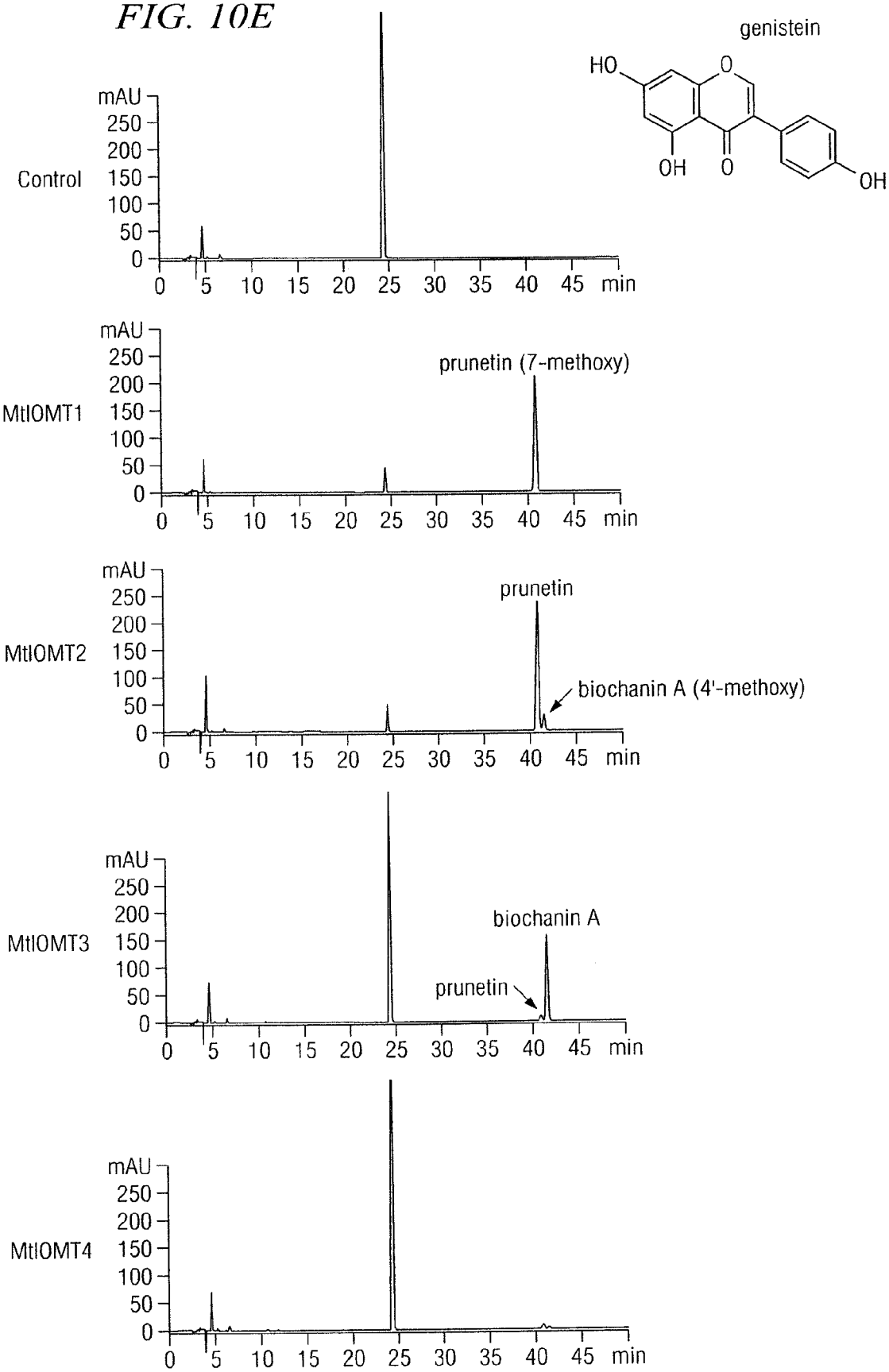
Figure 10E:
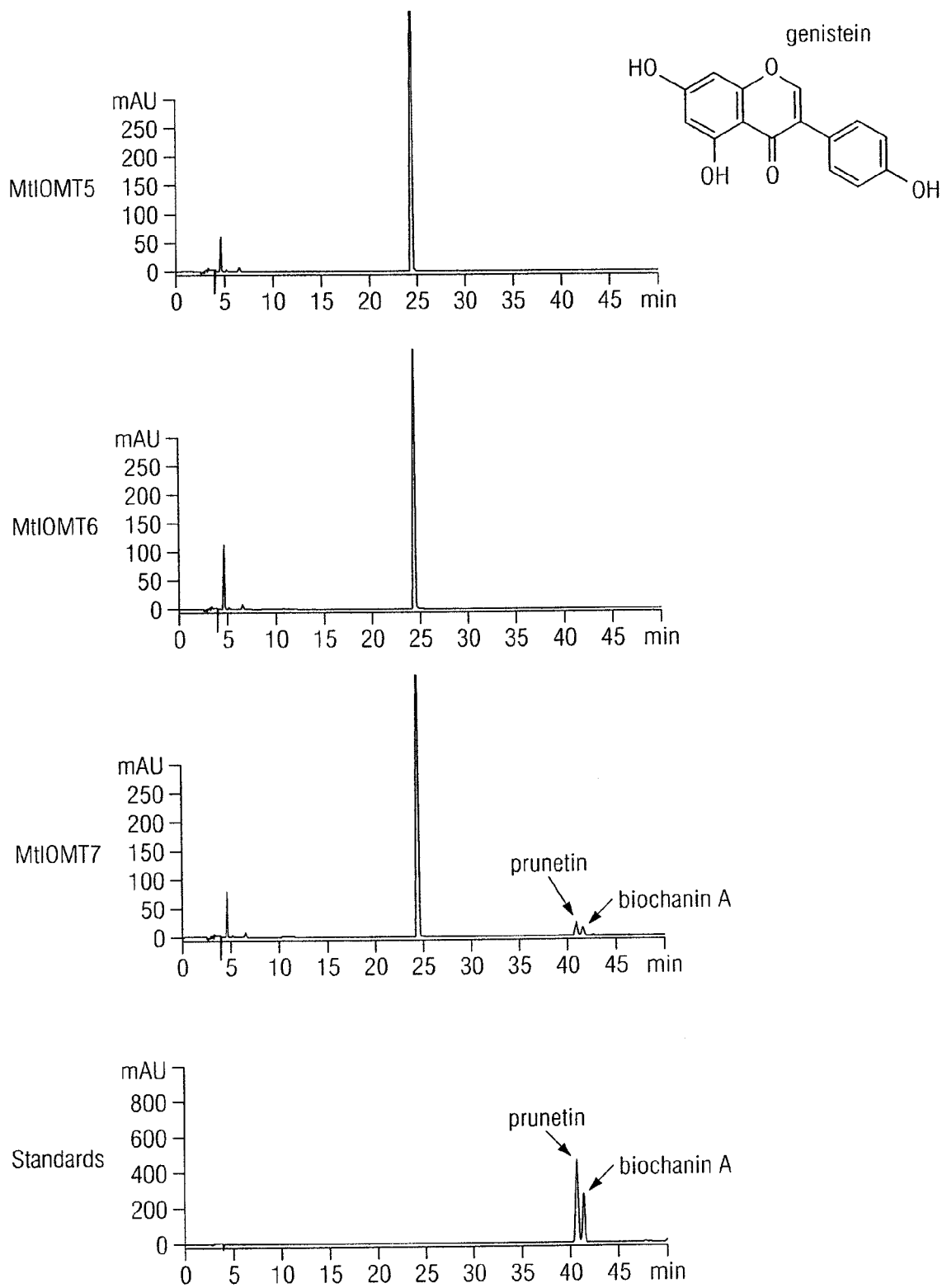
Figure 10F:
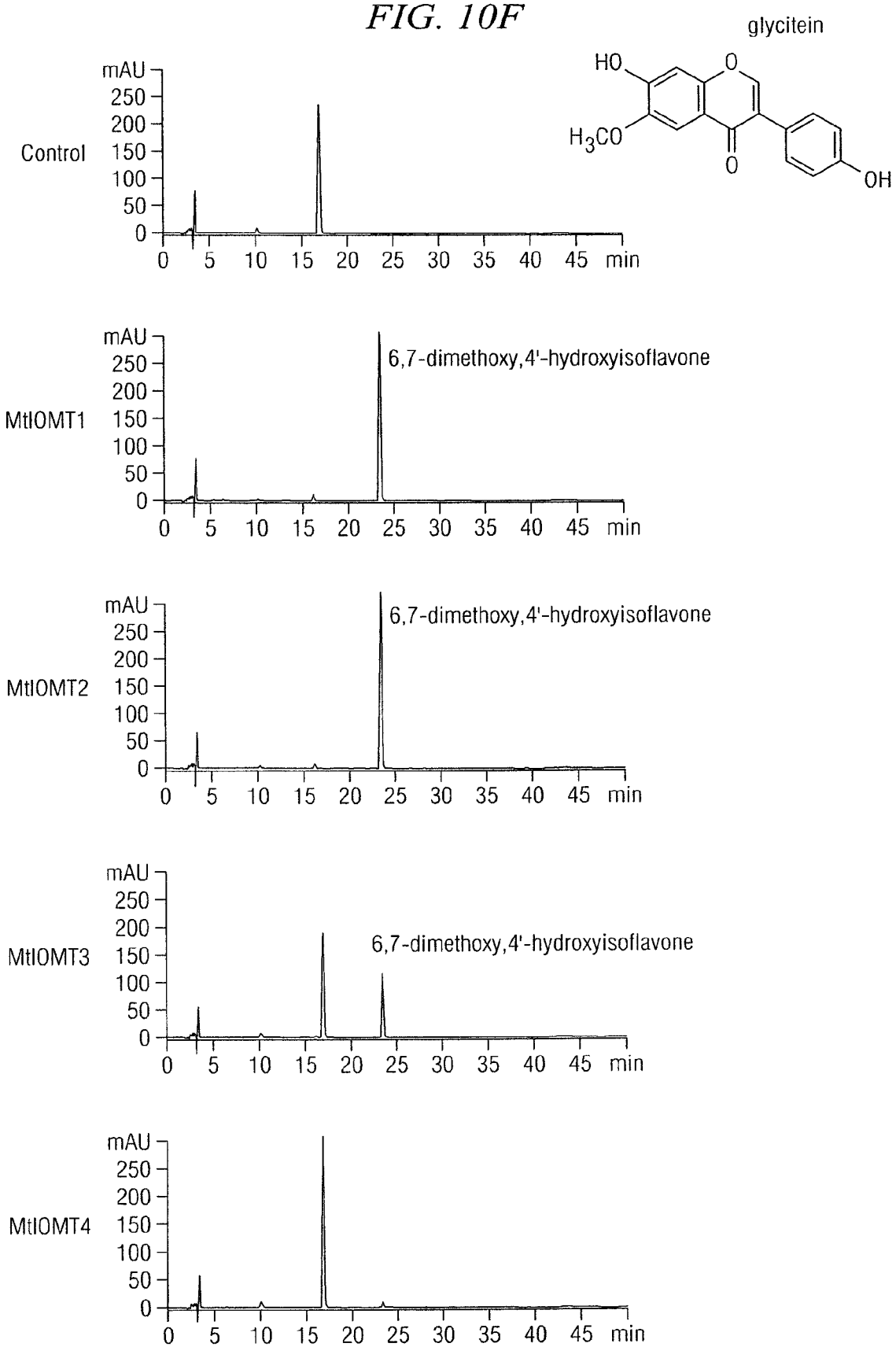
Figure 10F:
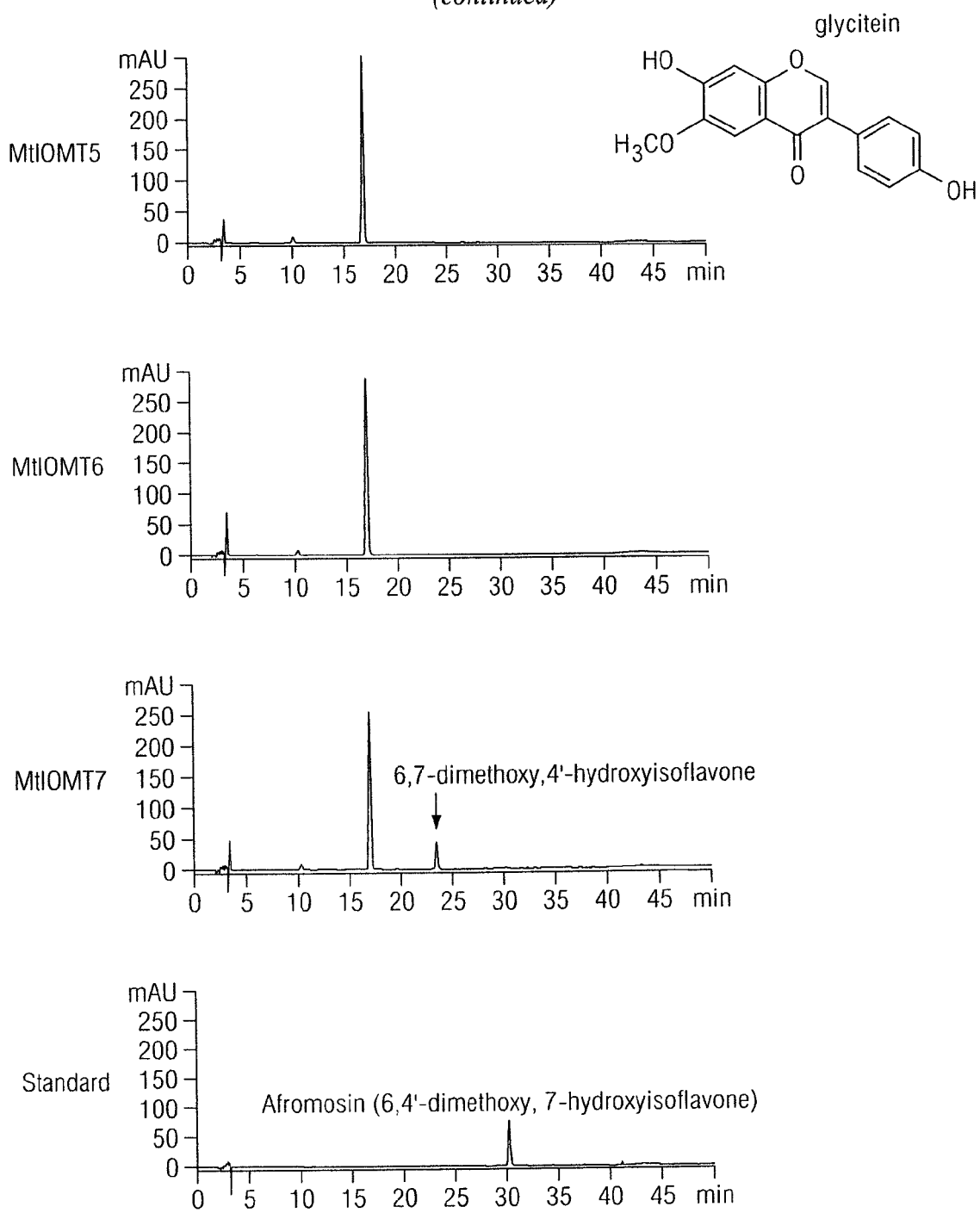
Figure 10G:
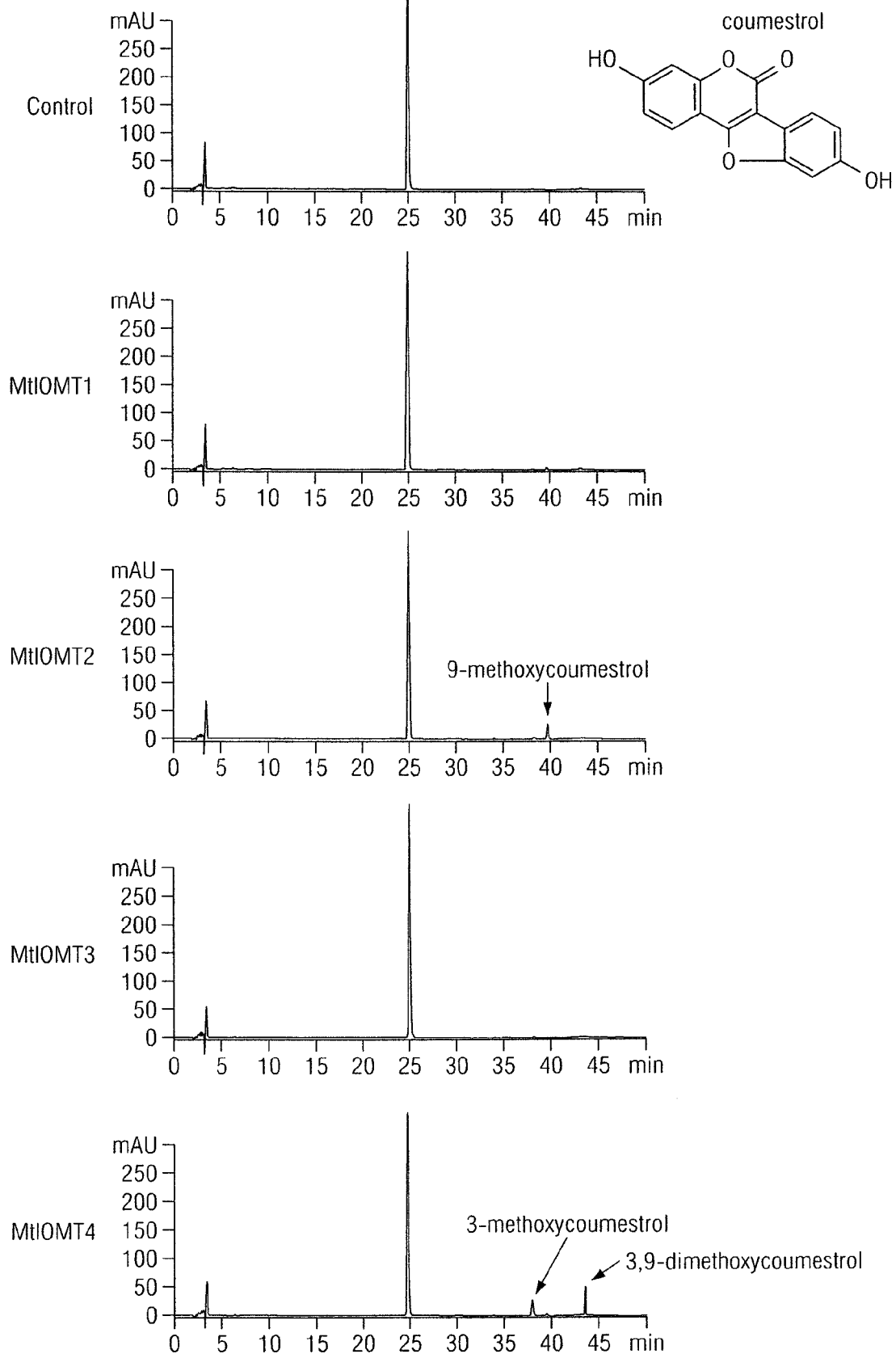
Figure 10G:
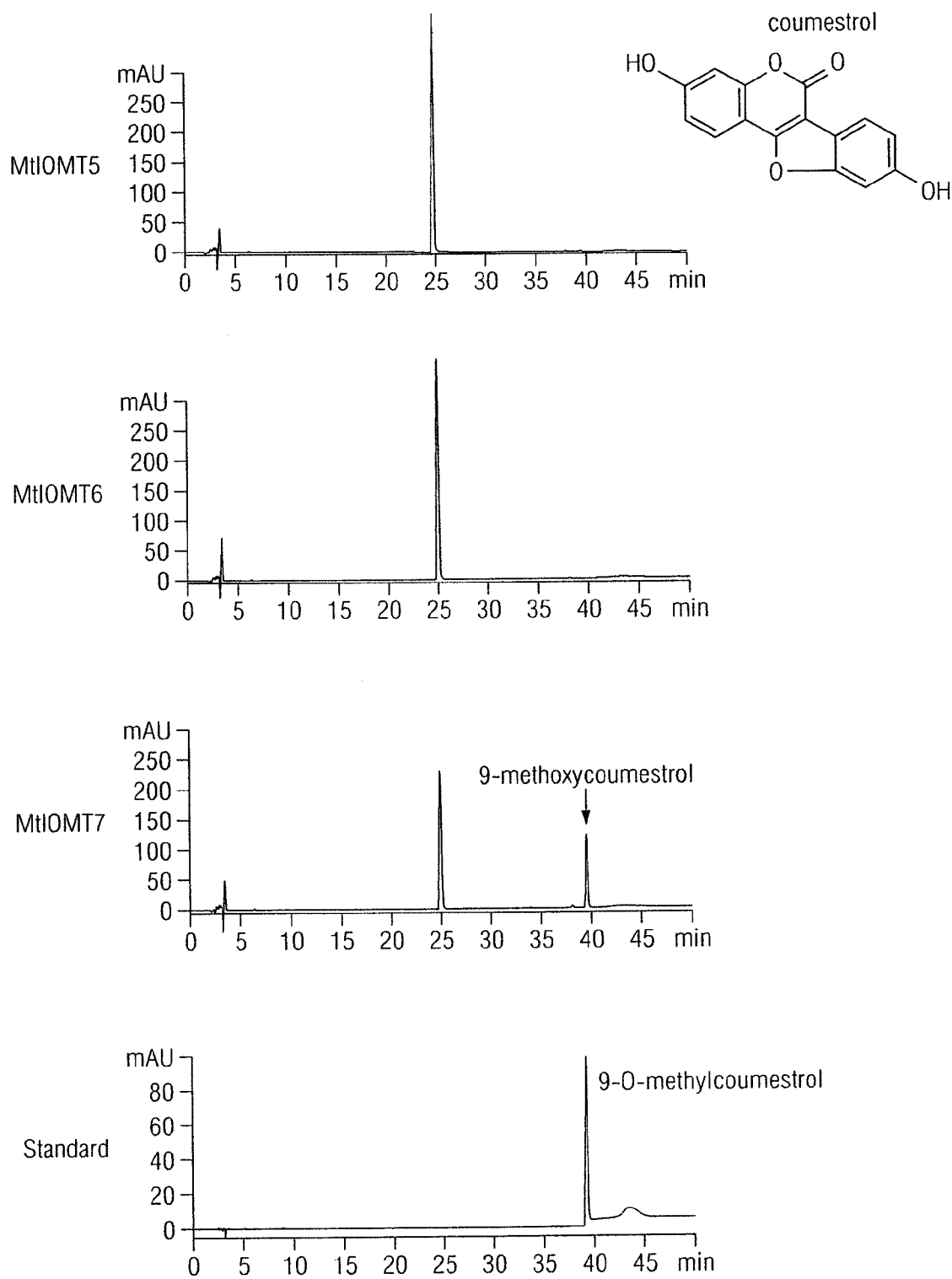
Figure 10H:
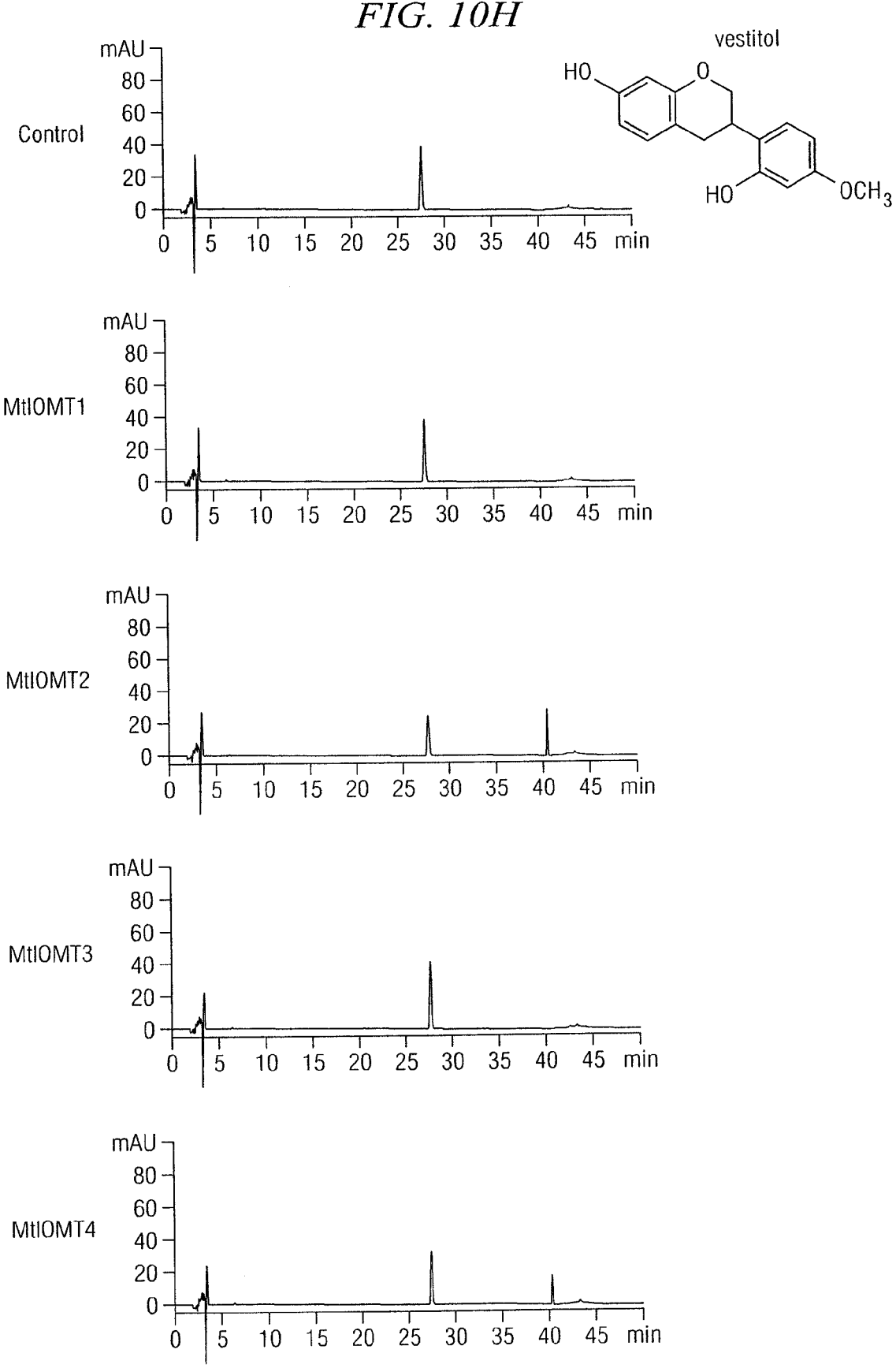
Figure 10H:
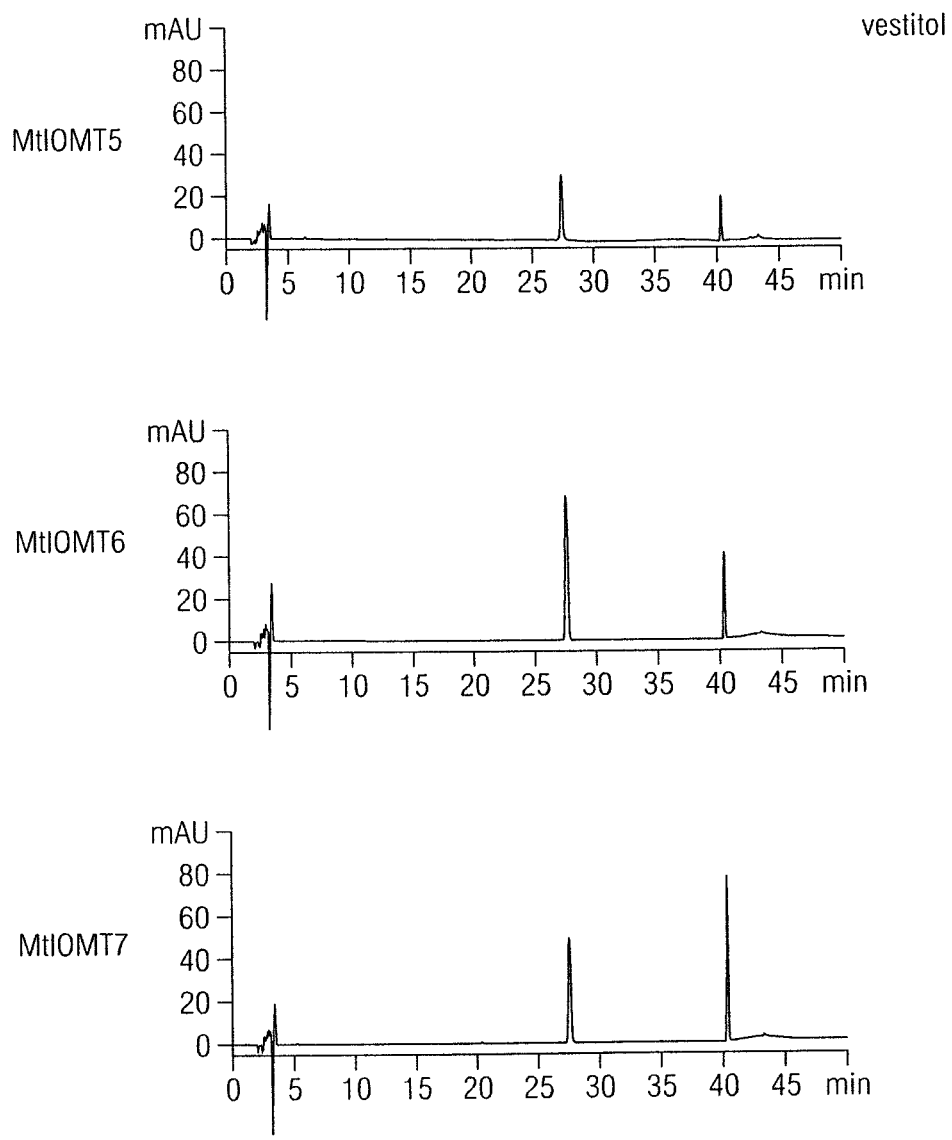
Figure 10I:
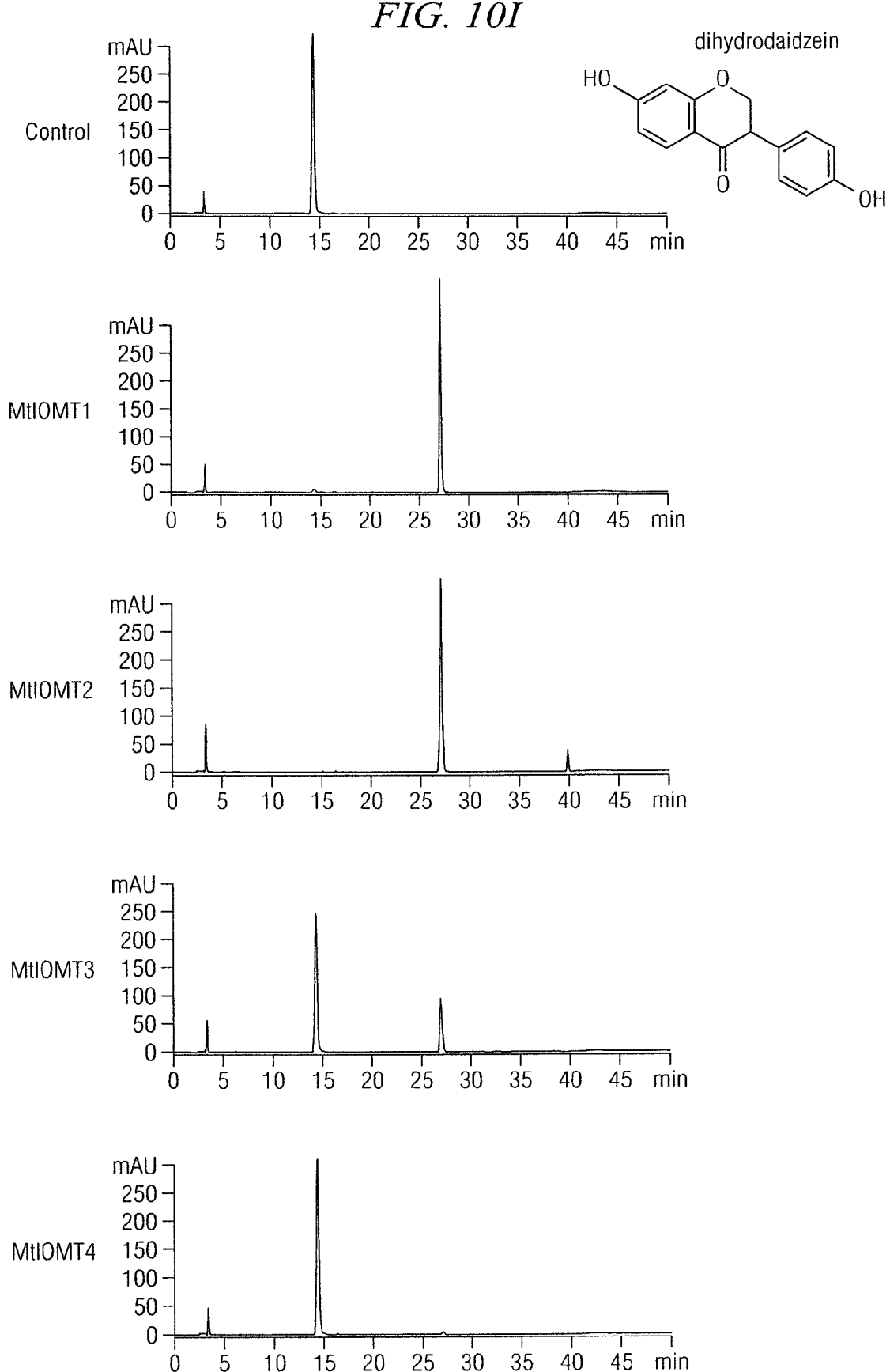
Figure 10I:
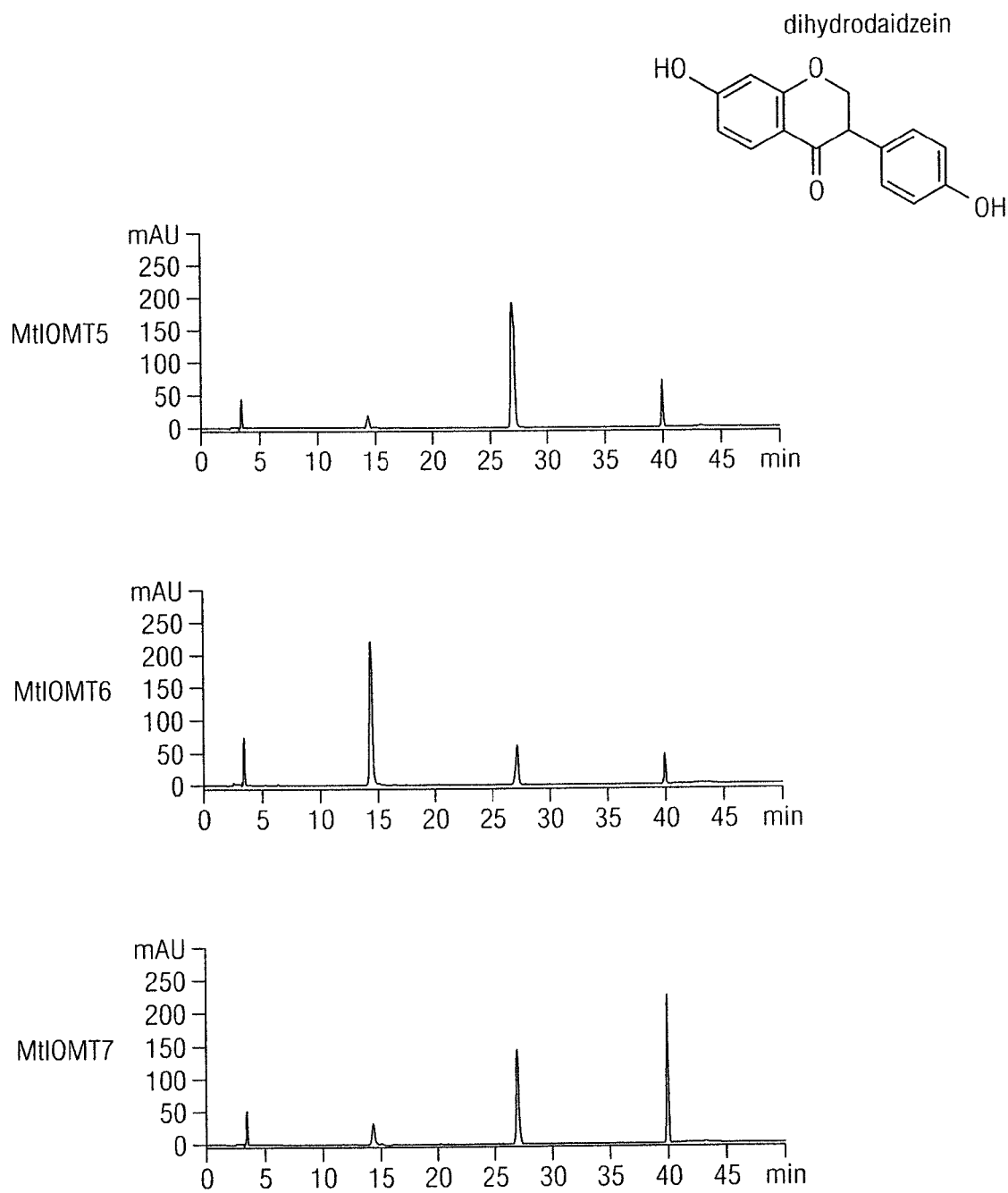
Figure 10J:
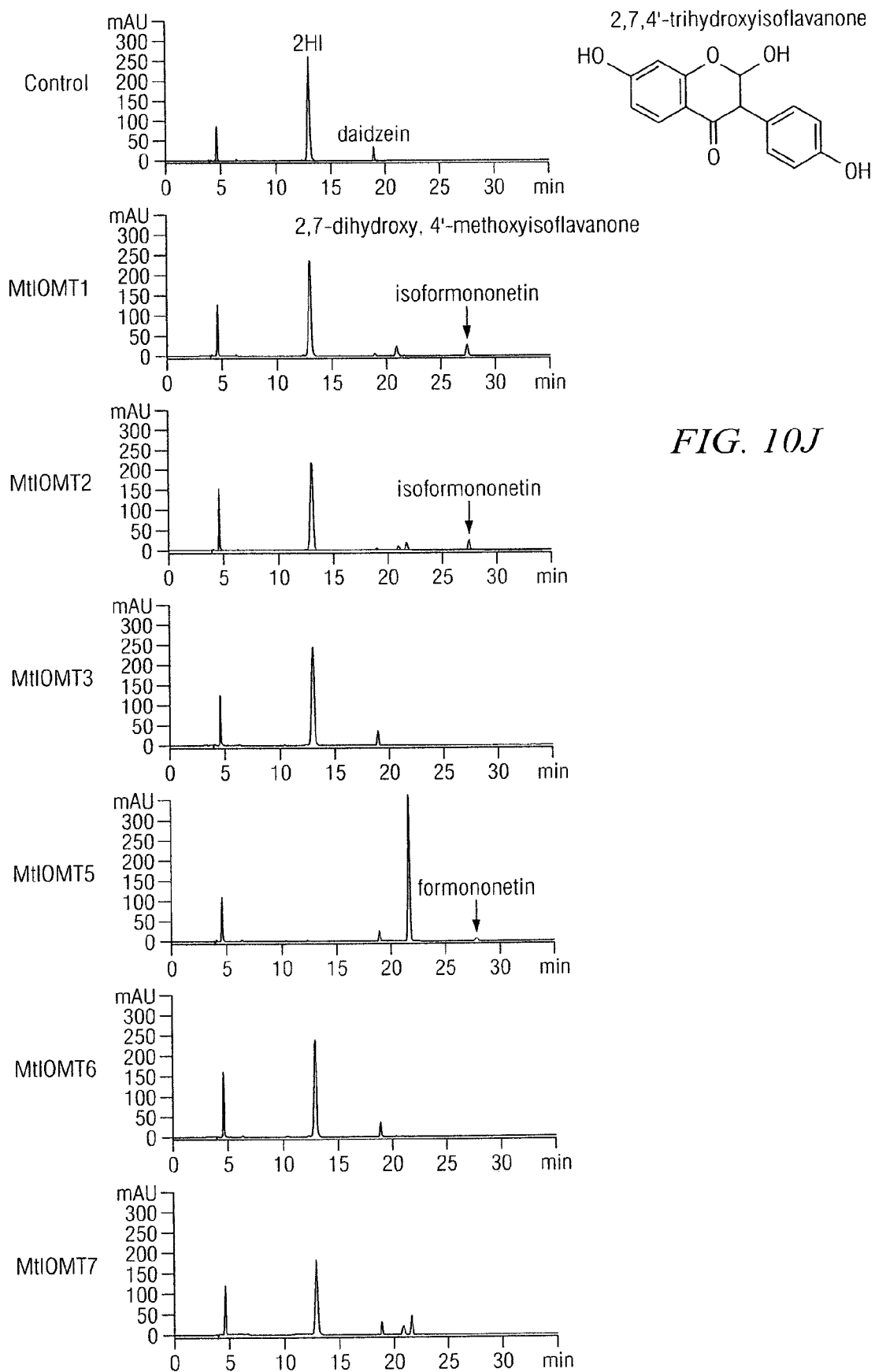

MtIOMT4 possesses low level, trace activity against vestitol and coumestrol (Table 3, FIG. 10), the latter being converted to both 3-O-methylcoumestrol and 3,9-O-dimethylcoumestrol, with a trace of 9-O-methylcoumestrol (FIG. 10G).

I. MtIOMT5

Figure 11:
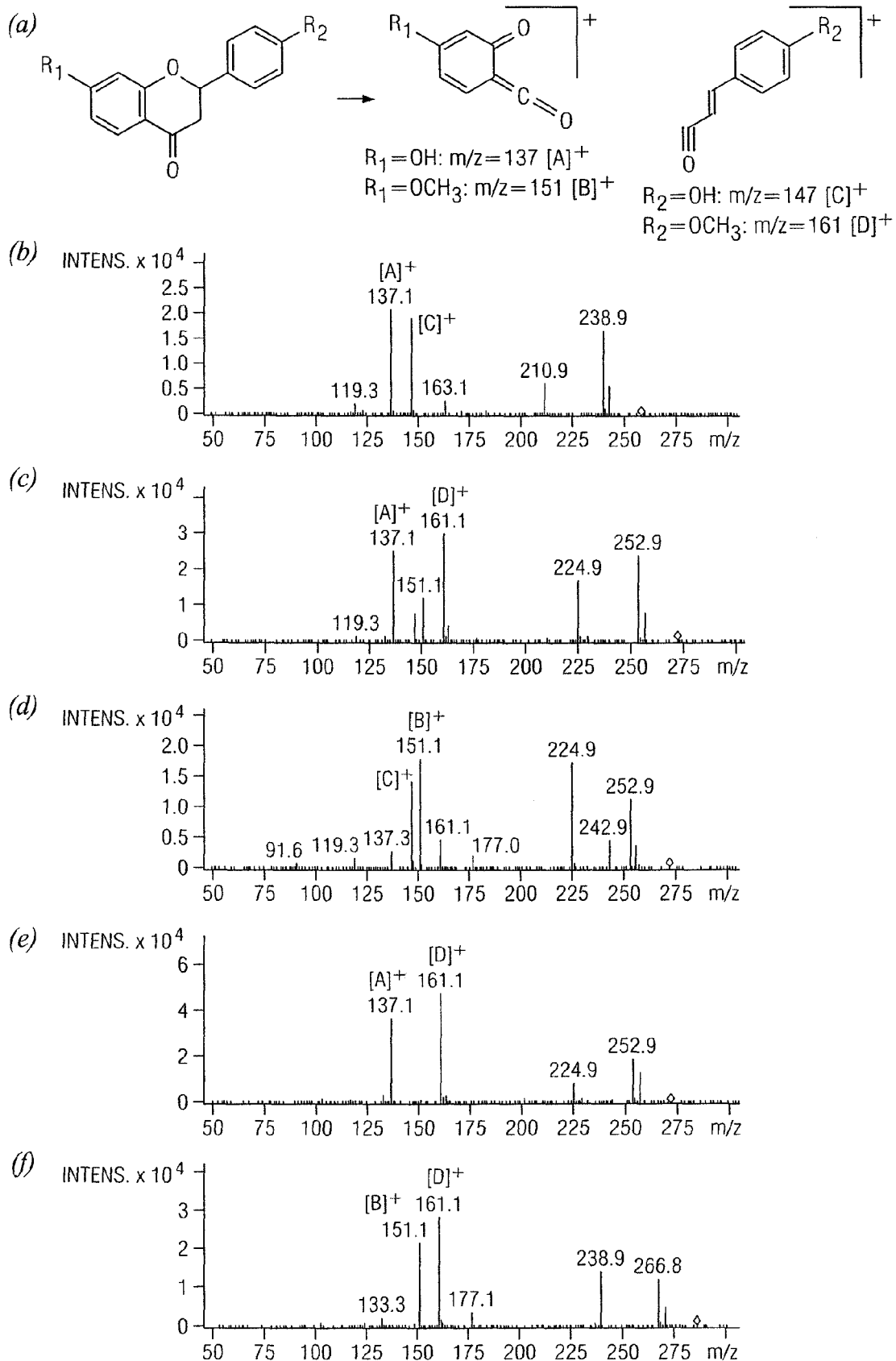
FIG. 11. Positive ion LC/ESI/MSMS spectra of reaction products from liquiritigenin: (a) Proposed fragmentation scheme. (b) Liquiritigenin precursor ion is m/z 257. (c) MtIOMT5 methylated product, precursor ion is m/z 271. (d-f) MtIOMT7 methylated products, precursor ion is m/z 271 (d,e) or m/z 285 (f).
Figure 12:
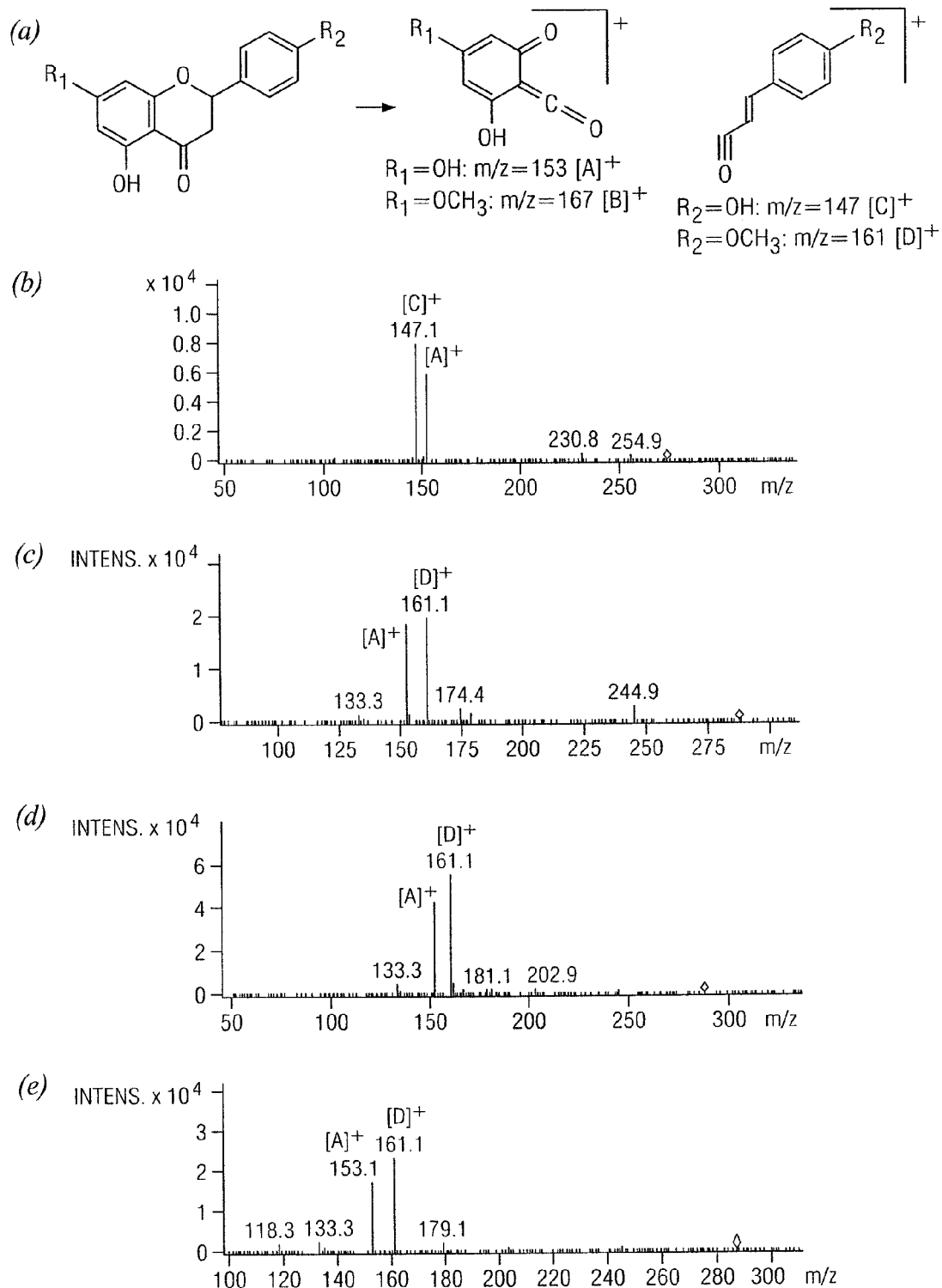
FIG. 12. Positive ion LC/ESI/MSMS spectra of naringenin reaction products. (a) Proposed fragmentation scheme. (b) Liquiritigenin precursor ion is m/z 273. (c) MtIOMT5 methylated product, precursor ion is m/z 287. (d) MtIOMT7 methylated products, precursor ion is m/z 287. (e) 5,7-Dihydroxy, 4'-methoxyflavanone standard, precursor ion is m/z 287.

MtIOMTs in the clade containing genes annotated as encoding 2,7,4'-trihydroxyisoflavanone or 6a-hydroxymaackiaian OMTs prefer non-planar substrates with one or more chiral centers. It has been recently shown that MtIOMT5 encodes the *M. truncatula* ortholog of the *G. echinata* HI4'OMT and methylates 2,7,4'-trihydroxyisoflavanone (the product of IFS) as well as (+)-6a-hydroxymaackiain (Liu et al., 2005). MtIOMT5 also methylates dihydrodaidzein, and to a lesser extent naringenin, liquiritigenin, and vestitol (Table 3). 2,7,4'-Trihydroxyisoflavanone is exclusively methylated on the 4'-position (FIG. 10J) whereas 4'-methoxy, 7-methoxy, and 4',7-dimethoxy products are observed in reactions with dihydrodaidzein (FIG. 13i, Table 1). Tandem MS indicated that the flavanones liquiritigenin and naringenin are methylated on the 4'-positions (FIGS. 11 and 12). Based upon HPLC analysis and quantification of reactions run to completion, the methylated flavanone products never account for more than 50% of the total amount of compound in the reaction mixtures, suggesting that only one stereoisomer of these enantiomeric compounds serves as substrate. Unreacted liquiritigenin remaining in reaction mixtures was primarily (2S)-liquiritigenin, as shown by chiral HPLC chromatography (FIG. 5b), indicating that MtIOMT5 preferentially methylates the (2R)-enantiomer (note that the (2S)-enantiomer of liquiritigenin is the naturally occurring form). The stereoisomers of vestitol could not be separated.

J. MtIOMT6

MtIOMT6 and MtIOMT4 possess the most narrow substrate specificity for (iso)flavonoids of the enzymes analyzed in the present work. Among the compounds tested, dihydrodaidzein and vestitol are the only ones methylated by MtIOMT6, and the specific activity with these compounds is very low. 4'-O-Methylated, 7-O-methylated, and 4',7-di-O-methylated products are observed in reactions with dihydrodaidzein (FIG. 13, Table 4).

K. MtIOMT7

Figure 5:
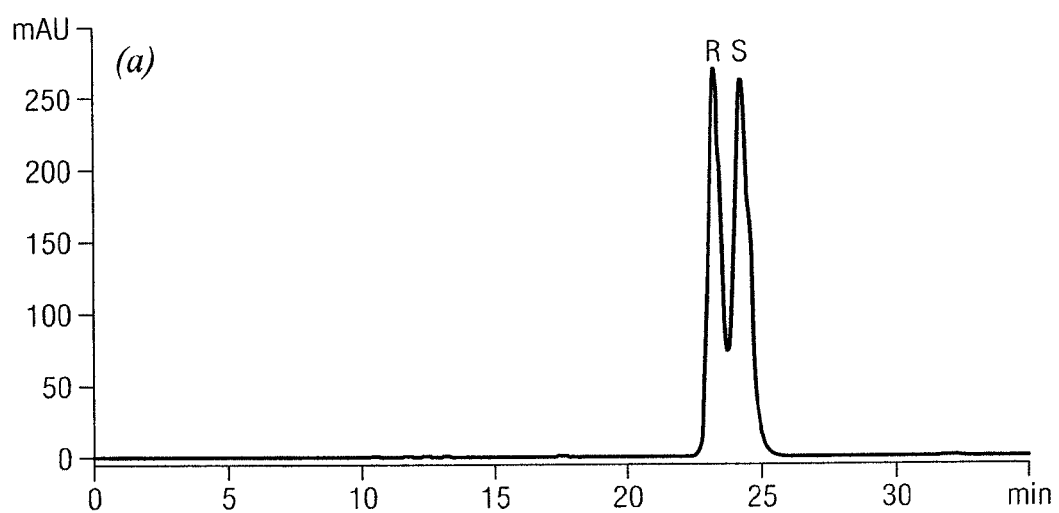
FIG. 5. Chiral HPLC chromatography of unreacted liquiritigenin present in reactions with MtIOMT5 (b) and MtIOMT7 (c). Racemic liquiritigenin standard is shown in (a).
Figure 5:
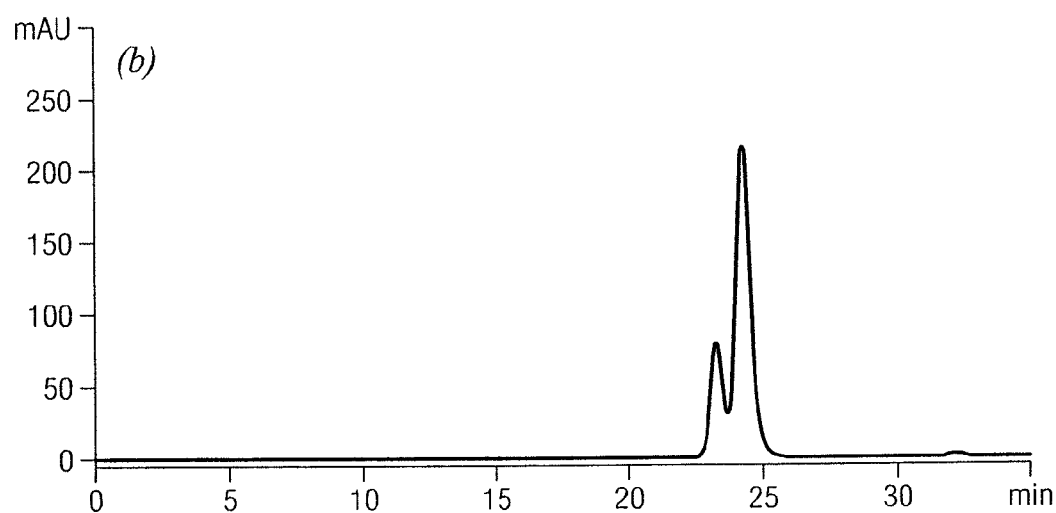
Figure 5:
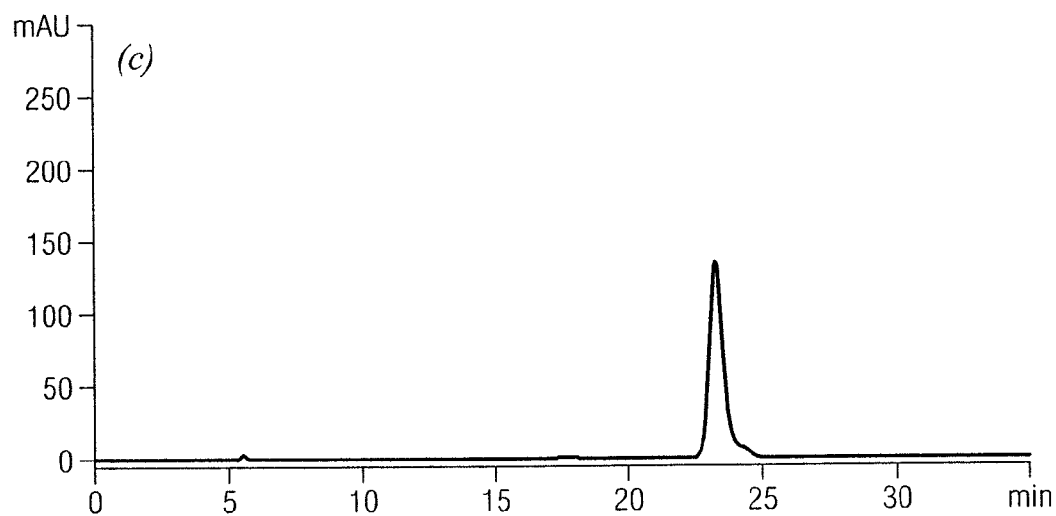
Figure 10K:
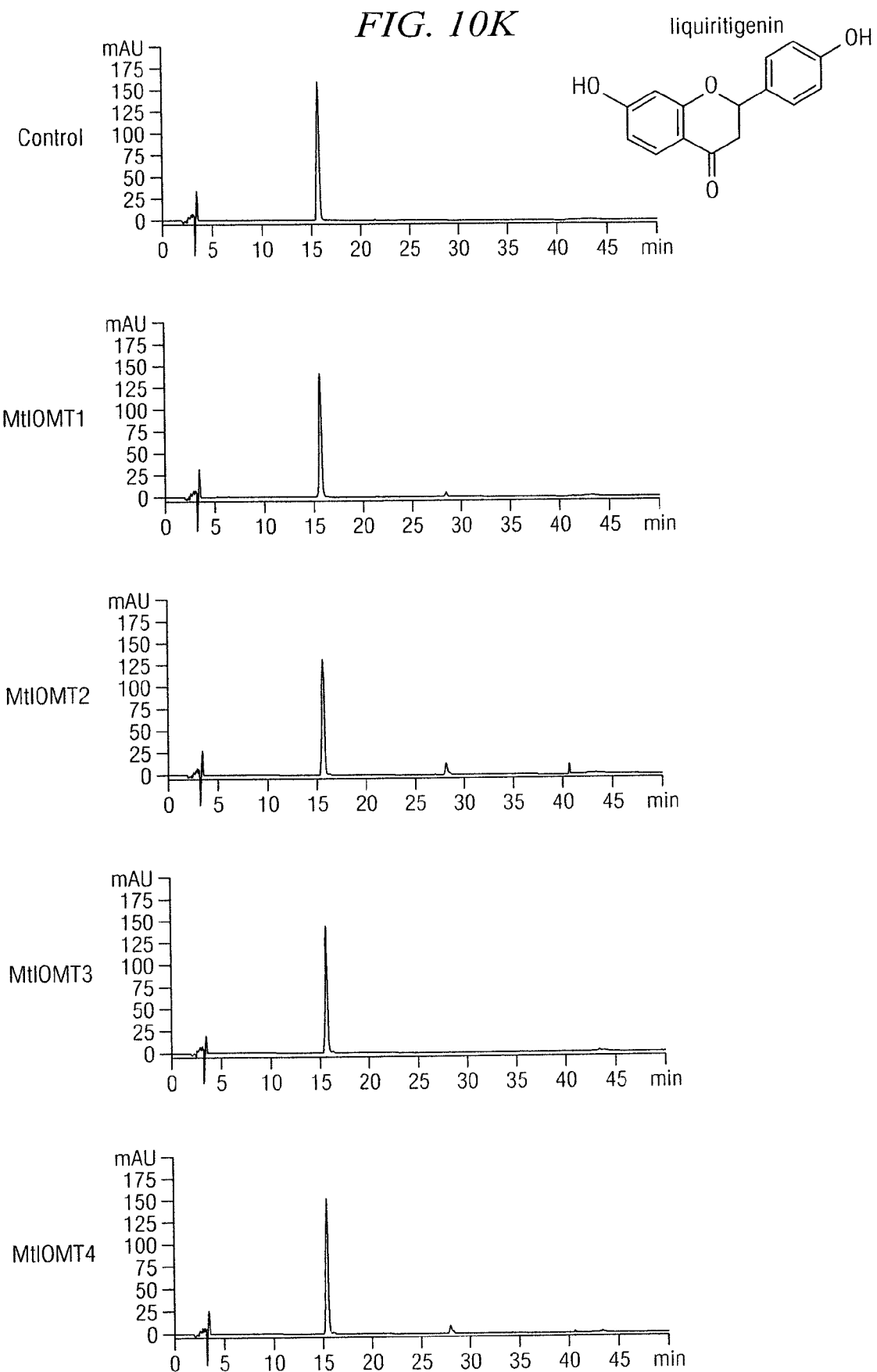
Figure 10K:
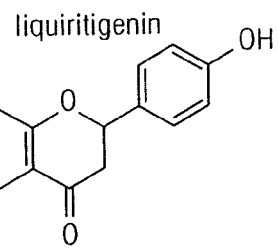
Figure 10K:
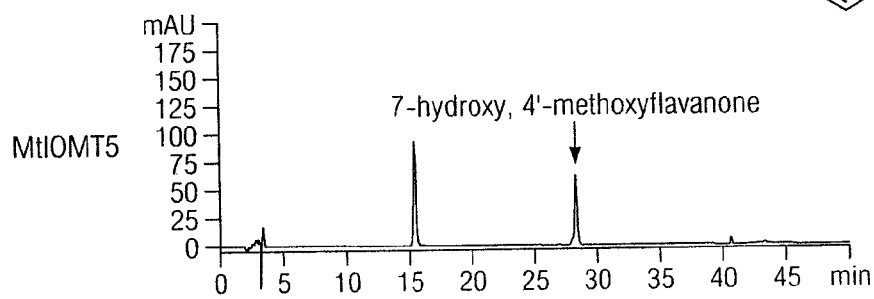
Figure 10K:
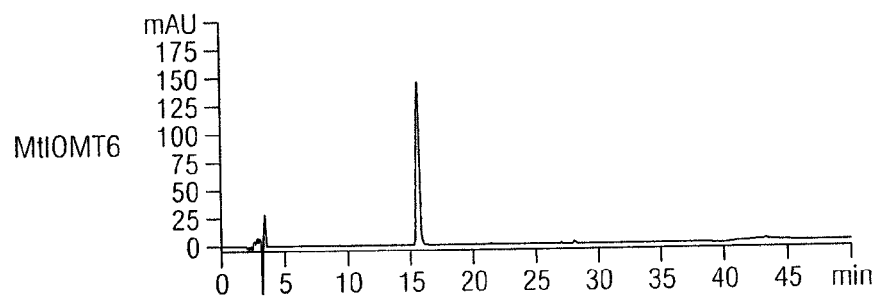
Figure 10K:
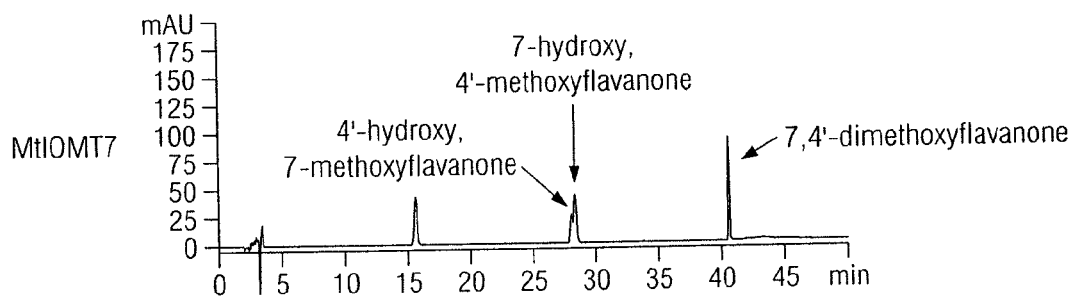
Figure 10L:
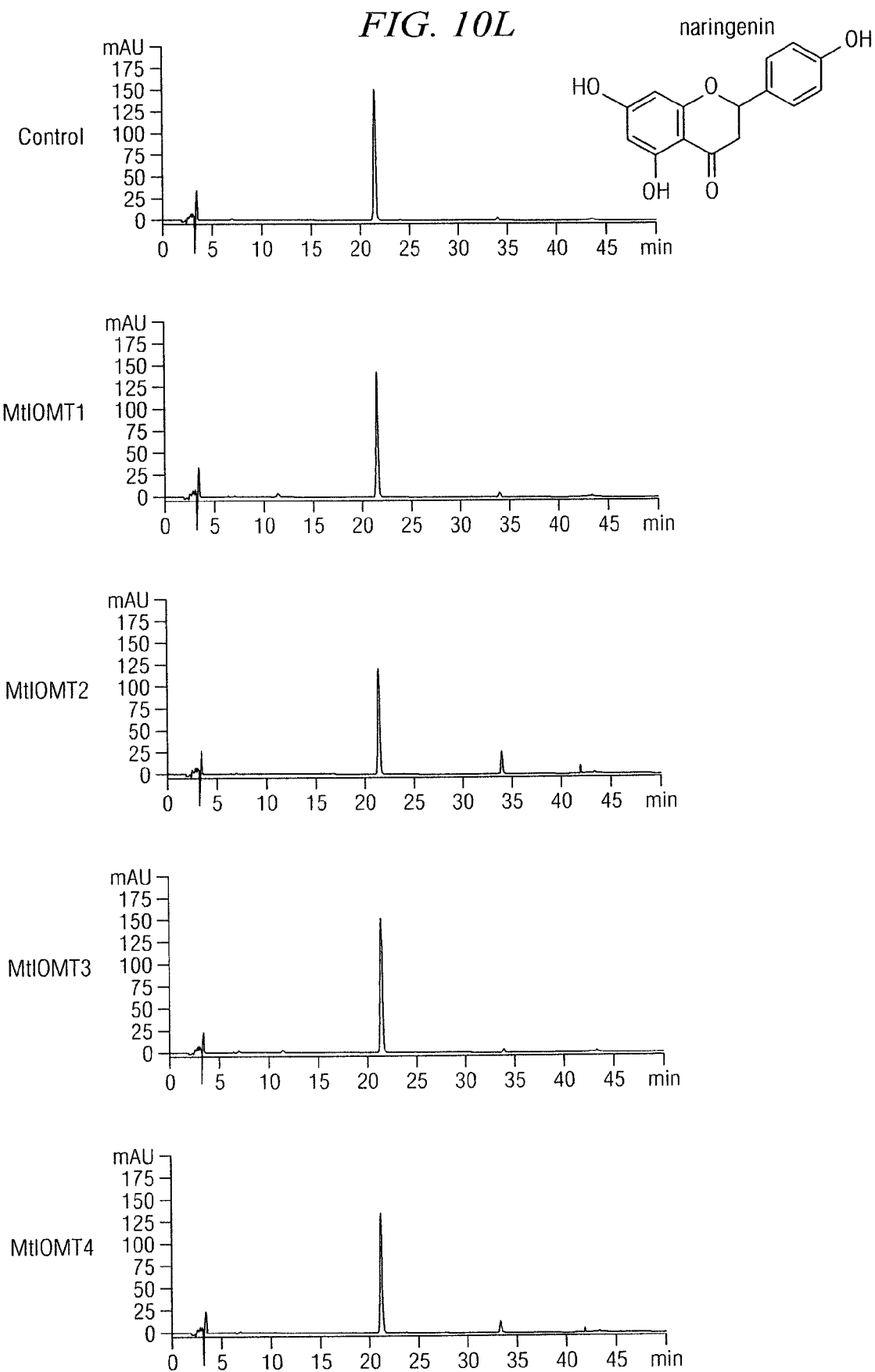
Figure 10L:
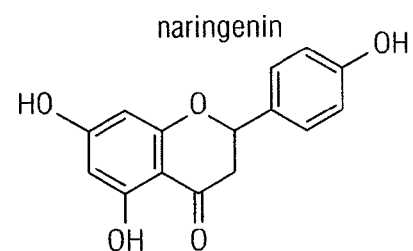
Figure 10L:
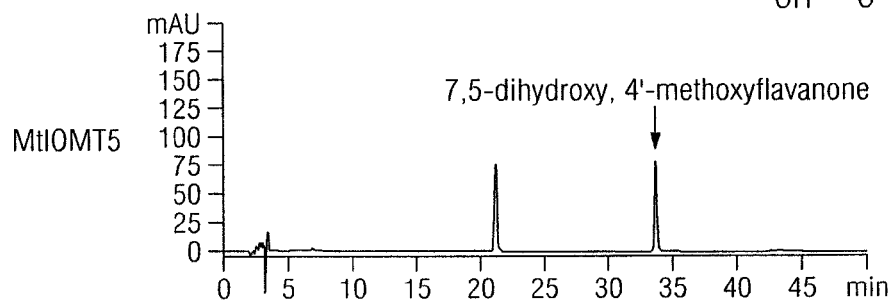
Figure 10L:
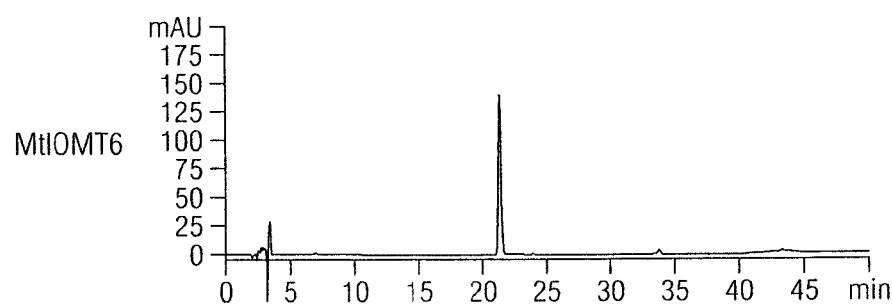
Figure 10L:
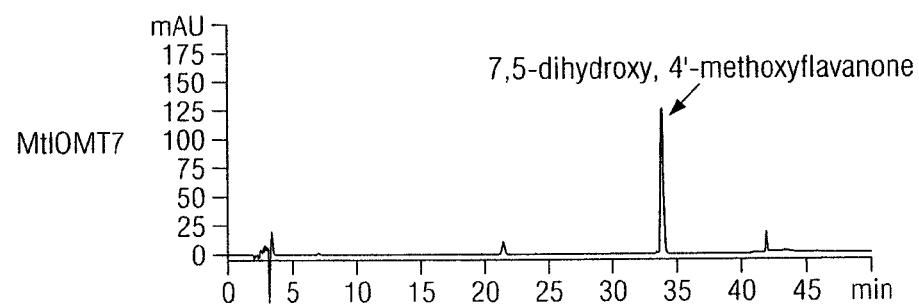
Figure 10L:
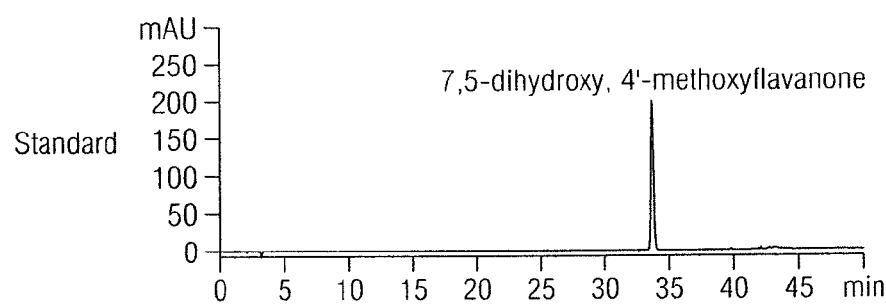
Figure 10M:
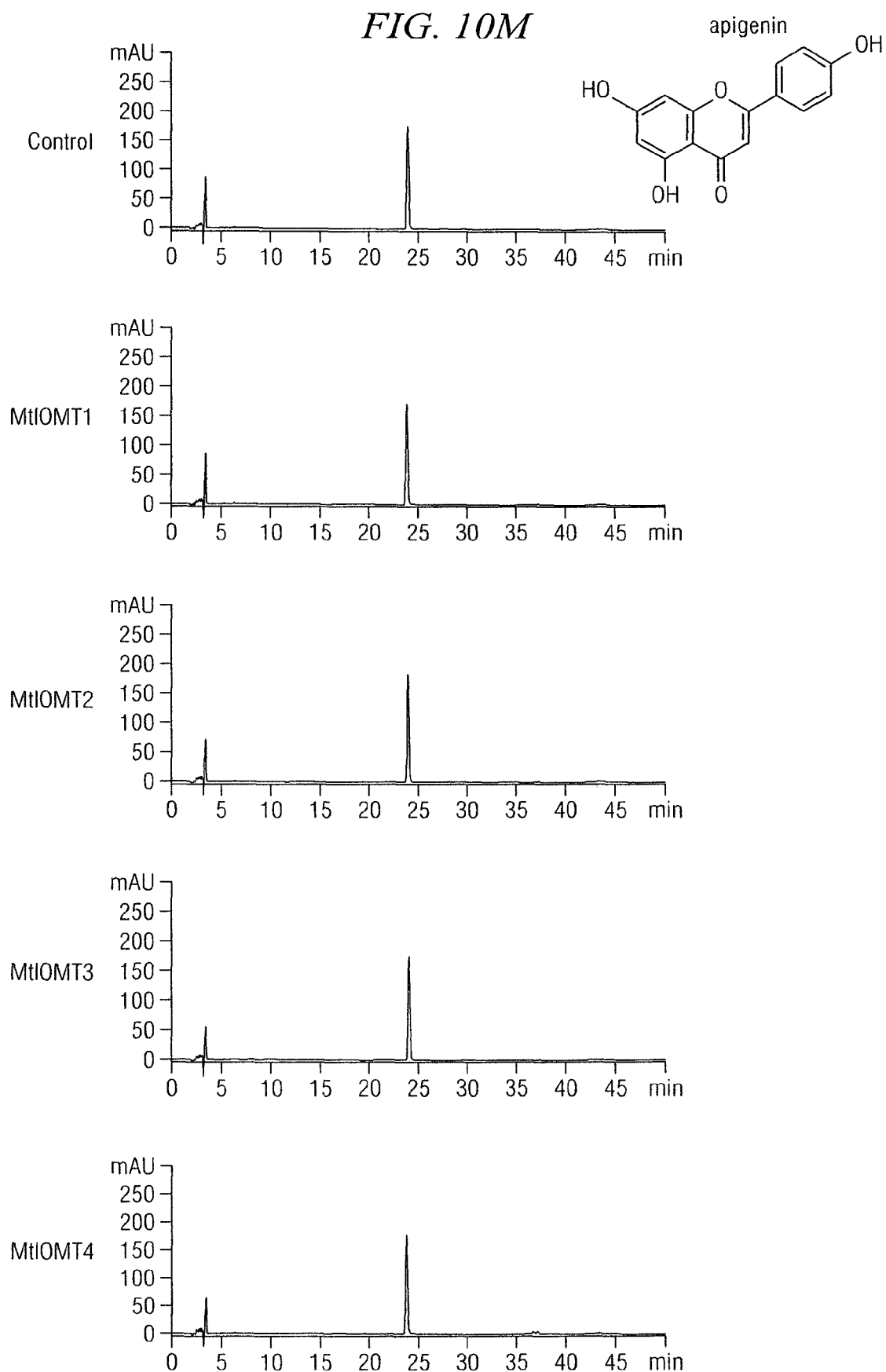
Figure 10M:
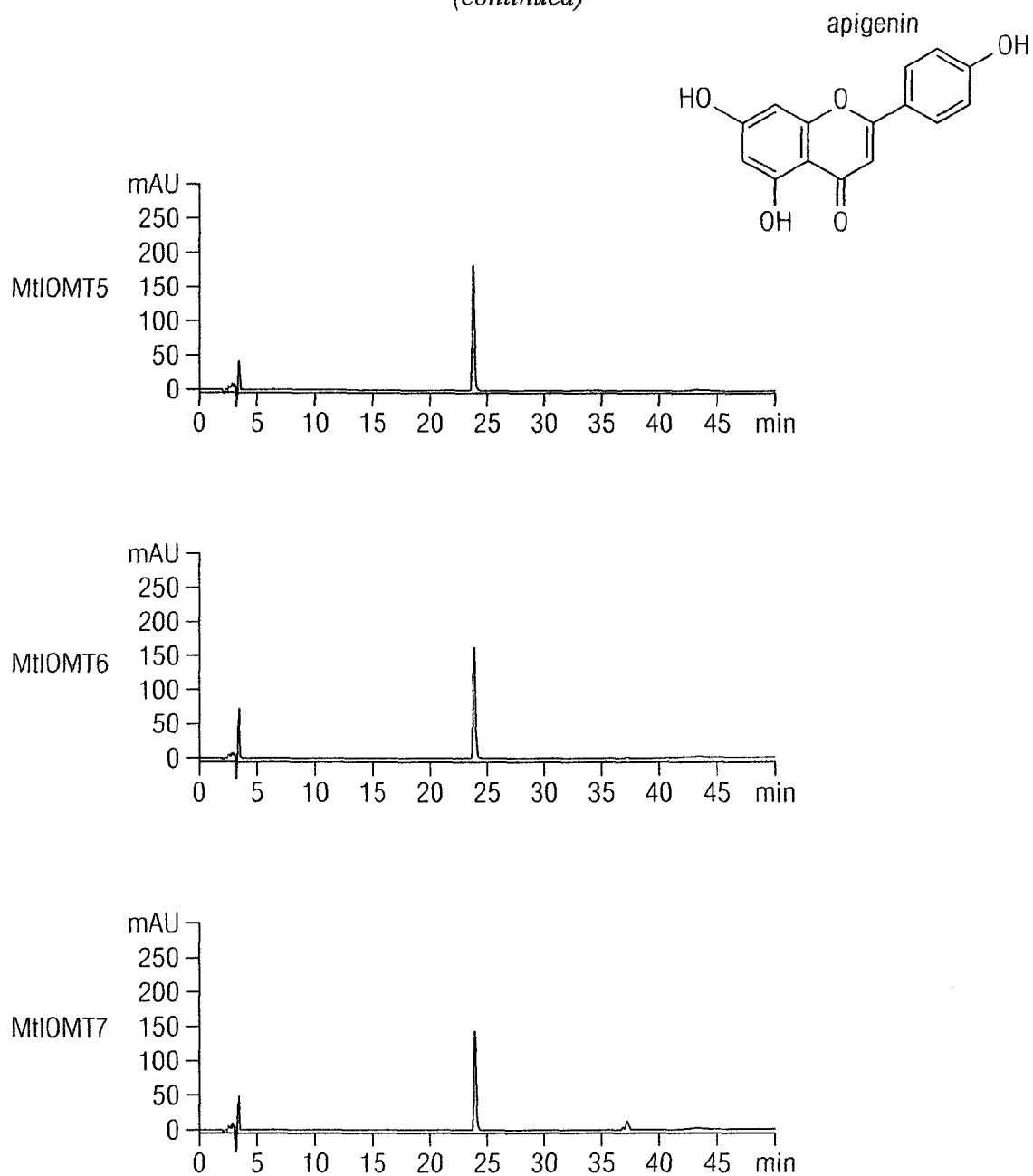
Figure 10N:
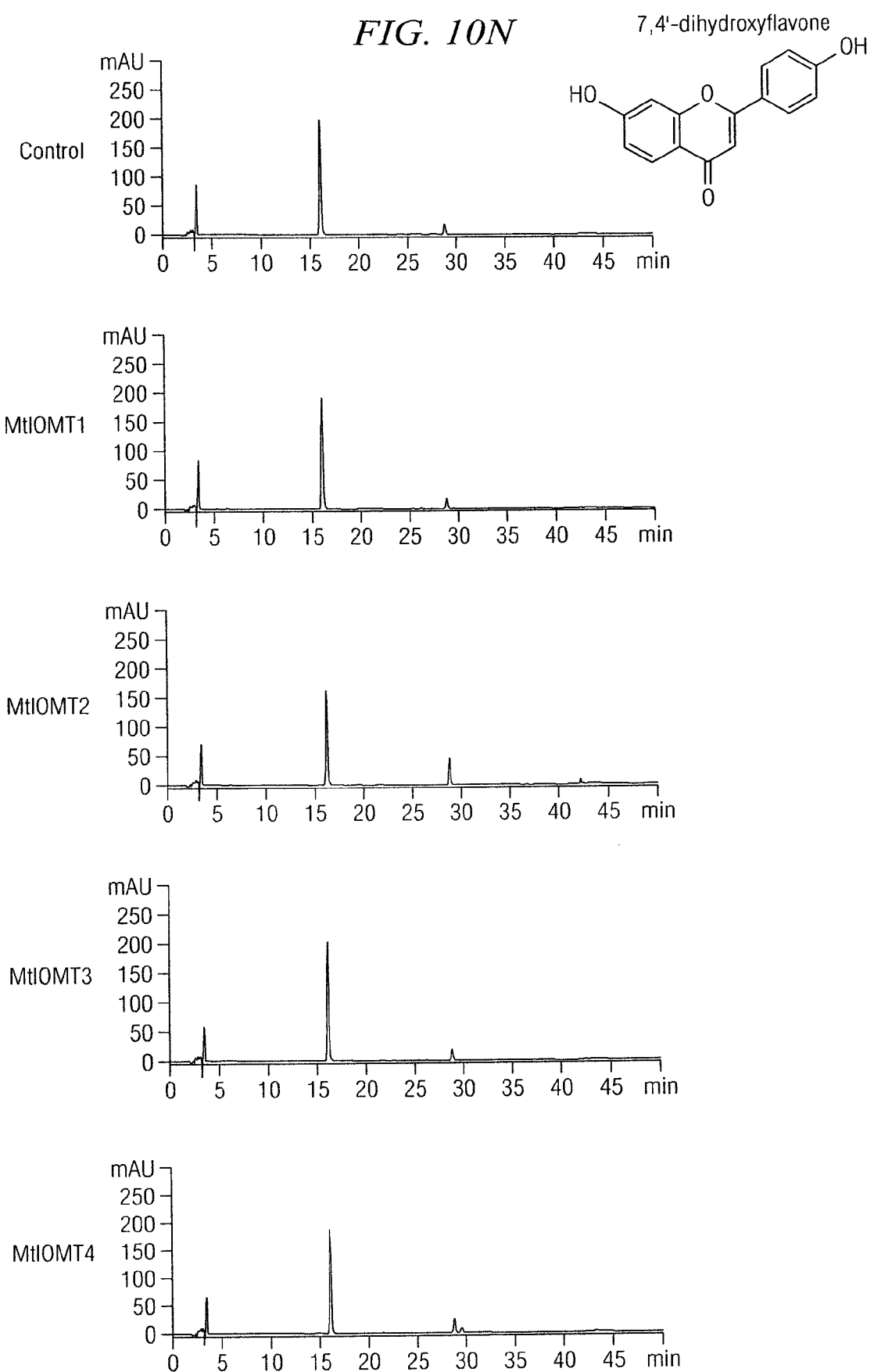
Figure 10N:
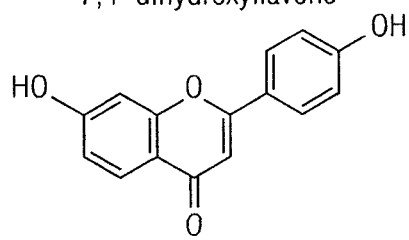
Figure 10N:
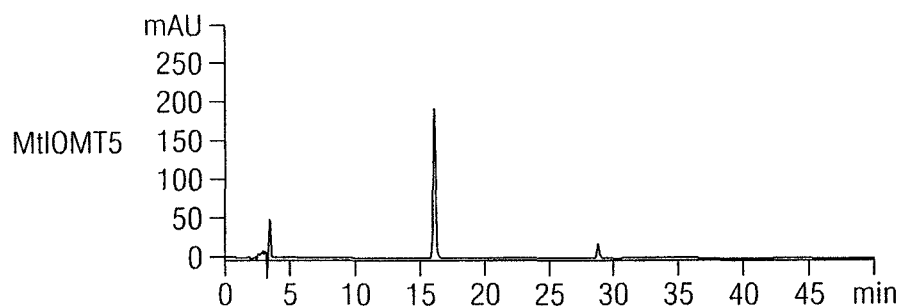
Figure 10N:
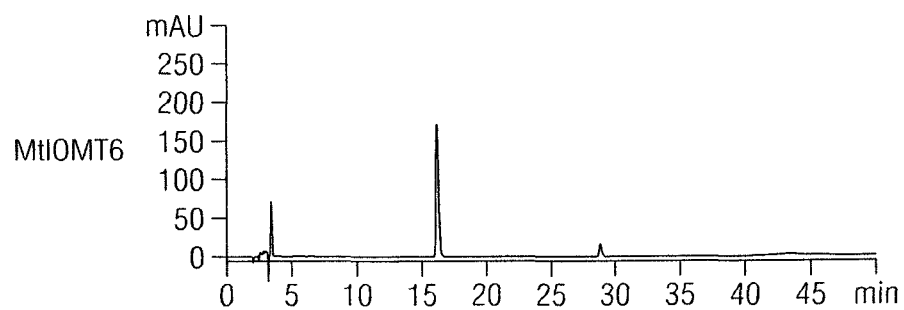
Figure 10N:
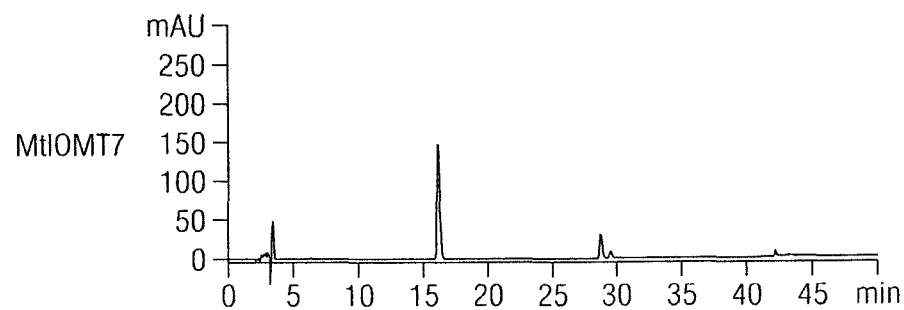

Naringenin and dihydrodaidzein are the best substrates for MtIOMT7 of the compounds tested. Almost all the naringenin is methylated after 2 h, suggesting that MtIOMT7 is able to methylate both (2S) and (2R)-enantiomers (FIG. 10L). Surprisingly, the liquiritigenin remaining in reactions after 2 h is the opposite enantiomer (2R) than that observed in reactions with MtIOMT5, indicating that MtIOMT7 preferentially methylates the (2S)-enantiomer (FIG. 5c). Multiple products are observed with both flavanones (FIGS. 10K, 10L). The major product with naringenin is 4'-O-methyl-naringenin; an additional peak, which elutes later on reverse phase HPLC, is most likely a dimethylated product (FIG. 10L). Three products are observed in reactions with liquiritigenin; these were identified as 7-O-methyl-liquiritigenin, 4'-O-methyl-liquiritigenin, and 7,4'-O-dimethyl-liquiritigenin (FIG. 11). Similarly, 4'-O-methylated, 7-O-methylated, and 4',7-di-O-methylated products are also observed in reactions with dihydrodaidzein (FIG. 13, Table 4). Two minor peaks are observed in reactions with 2,7,4'-trihydroxyisoflavanone, one of which corresponds to 2,7-dihydroxy, 4'-methoxyisoflavanone (FIG. 10J). MtIOMT7 also methylates vestitol and coumestrol (9-O-methylation). Minor peaks are observed in reactions with 7,3',4'-trihydroxyisoflavone and glycitein (both 7-O-methylated).

Example 8

Molecular Modeling Studies

To gain insight into the structural basis of IOMT substrate specificity, homology modeling of MtIOMTs from the 7-OMT clade was performed using the previously solved structure of MsI7OMT complexed with isoformononetin (PDB: 1FP2) (Zubieta et al., 2001). Homology modeling was performed using the program MODELLER. The quality of models was evaluated by PROCHECK and visualized using the 0 program. Subsequently, isoflavonoid substrates were docked using the GOLD program.

Superimposition of the modeled MtIOMT1 structure with that of MsI7OMT revealed that the active site of MtIOMT1 is nearly identical to that of MsI7OMT, consistent with the virtually identical activities of these two enzymes determined using in vitro assays (Table 3). Only one amino acid difference is found in the active site of the MtIOMT1 model; Tyr 25, which forms the back wall of the active site and is contributed from the dyad related monomer, is replaced by a conservative Phe substitution.

Figure 6:
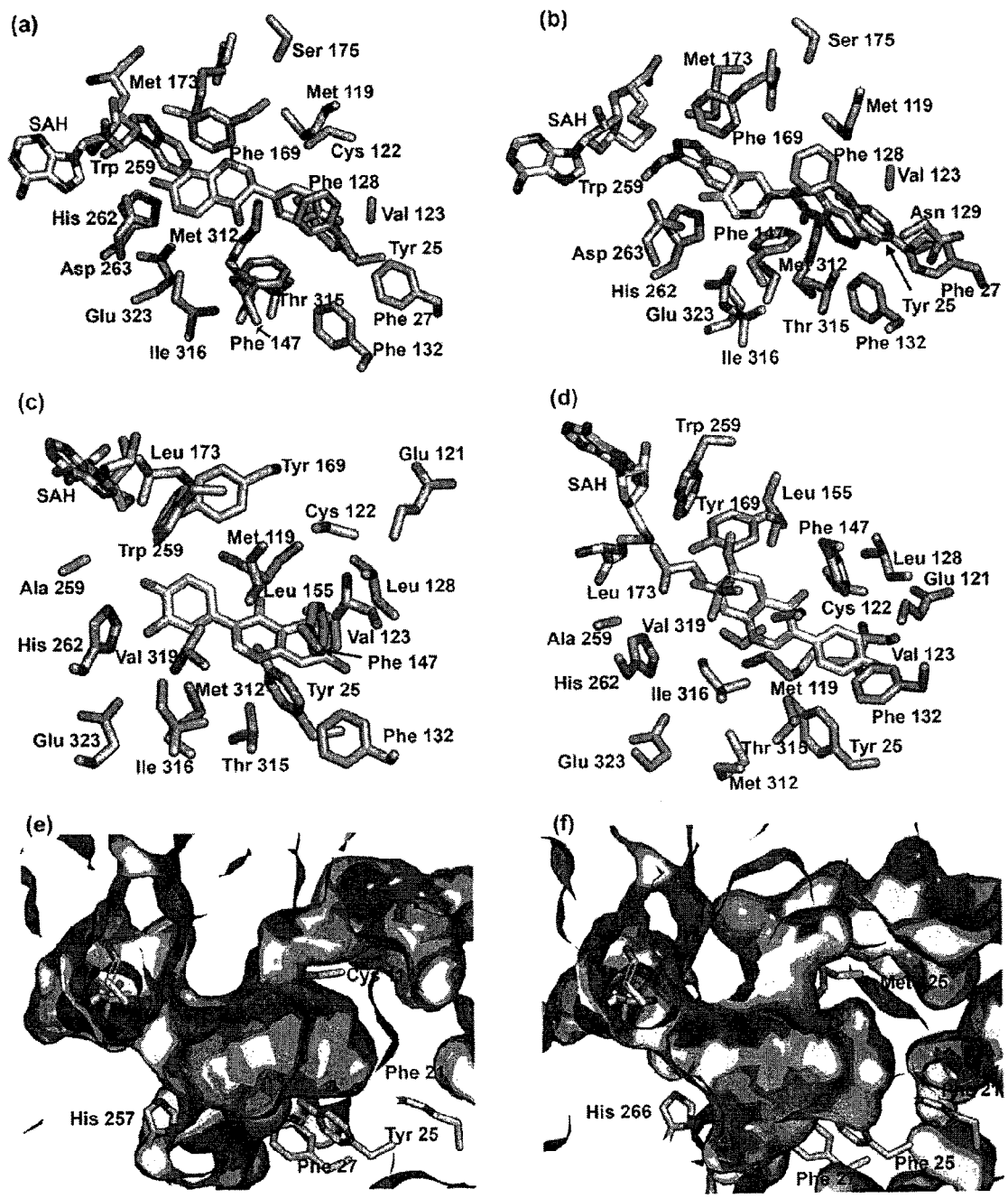
FIG. 6. Homology models of selected members of the MtI7OMT clade. (a, b) Close-up view of the MtIOMT2 active site with dihydrodaidzein docked for 7-O-methylation (a) or 4'-O-methylation (b). (c, d) View of 7,3',4'-trihyroxyisoflavone (c) and glycitein (d) docked into the MtIOMT3 active site. (e, f) Molecular surface views of the experimentally determined MsI7OMT active site (e) and the modeled MtIOMT4 active site (f).

In the active site of the MtIOMT2 model, Tyr 127, Asn310, Met311 and Phe150 in MsI7OMT are replaced by Phe132, Thr315, Ile316, and Leu155, respectively (FIG. 6a, b). In total, these changes result in a significant increase in the predicted volume of the substrate binding pocket of MtI-OMT2, particularly in the bottom part of the cavity. Furthermore, replacement of Met311 of MsIOMT7 by Ile316 in MtIOMT2 may alter the hydrophobic packing and thioether-mediated interaction of the side chain at this position with the bound substrate/product found experimentally in MsI7OMT complexed with isoformononetin (Zubieta et al., 2001). These structural alterations would be predicted to allow for greater flexibility in substrate positioning in the active site of MtIOMT2 compared with that of MsIOMT7.

To test this hypothesis, dihydrodaidzein, a substrate that is methylated at either the 7 or 4'-positions in vitro, was docked into the active site of the MtIOMT2 homology model by orienting either the 7- or 4'-hydroxy group toward the catalytic general base, His 262, and the reactive methyl group of SAM (FIG. 6a, b). When dihydrodaidzein is oriented for 7-O-methylation, the binding pattern is comparable to that determined experimentally for isoformononetin in the MsI7OMT structure; moreover, the enlarged binding pocket in MtIOMT2 compensates for the more bent isoflavanone conformation (FIG. 6a). This enlarged binding cavity also allows dihydrodaidzein to be docked with its 4'-hydroxyl moiety pointing toward the catalytic His and reactive SAM methyl donor (FIG. 6b). In particular, substitution of Asn 310 and Tyr 127 in MsI7OMT for Thr 315 and Phe 132 respectively in MtIOMT2 create the necessary volume in the binding cavity to accommodate the planes formed by the A- and C-rings of dihydrodaidzein. The edge to face van der Waal's interactions of the side chain of Phe 147 with the plane formed by the A- and C-rings of the modeled substrate may further accommodate the substrate, while the amide moiety of Asn 129 and the phenolic group of Tyr 25 can potentially form hydrogen bonds with the 7-hydroxyl moiety and the oxygen atom of the ketone group of dihydrodaidzein. Finally, Met 119, Met 173 and Met 312 form a three pronged clamp loosely packing around the modeled substrate molecule (FIG. 6b).

In the active site model of MtIOMT3, Phe 164 in MsI7OMT is changed to Tyr 169 in MtIOMT3 while the diagonally arranged residue, Tyr 127 in MsI7OMT, is replaced by Phe 132 in MtIOMT3 (FIGS. 6c and d). These substitutions in MtOMT3 diagonally alter the architecture and hydrophobic environment of the active site. As seen in the MtIOMT2 homology model, several active site substitutions increased the volume of the phenolic binding pocket, which may offer an explanation for the ability of MtIOMT3 to methylate at the 7 or 4'-positions. When 7,3',4'-trihydroxy-isoflavone is docked into the active site model of MtIOMT3, the 4'-hydroxyl moiety is placed proximal to the putative catalytic base, His 262, and oriented towards the reactive methyl group of SAM; the 3'-hydroxyl group projects into the extra space created by the substitution of Met 311 in MsI-OMT7 by Ile 316 in MtIOMT3. Finally, the A-ring 7-hydroxyl moiety inserts into the small cavity formed by Phe 132, Phe 147, Leu 128, Val 123, Tyr 25 and Phe 27, the latter two residues being contributed from the dyad related monomer (FIG. 6c).

When glycitein is docked into the active site of MtIOMT3, the energetically favorable orientation of the compound results in its being flipped horizontally and vertically relative to 7,3',4'-trihydroxyisoflavone, with the 6-methoxy moiety of the compound pointing into the hole formed by Leu 155, Trp 259, Tyr 169, and Leu 173 (FIG. 6d). Hydrophobic interactions with the 6-methoxyl moiety within this apolar crevice serve to lock down the bound conformation of glycitein modeled into MtIOMT3's active site pocket.

The active site residues of the modeled MtIOMT4 structure are notably different across the entire active site from those observed in MsI7OMT. These large scale changes likely result in extensive architectural changes of the phenolic substrate binding pocket relative to that of MsIOMT7 (FIG. 6e,f). The substitution of Phe 142 and Cys 117 in MsI7OMT by Tyr 150 and Met 125 respectively in MtIOMT4 shrink the available space of the top half of the substrate binding cavity (FIG. 6f), while the substitution of Asn 310, Tyr 127 and Tyr 25 in MsI7OMT by Ile 319, Phe 135, and Phe 25 in MtIOMT4 (the latter from the dyad related monomer) conversely enlarge the bottom half of the substrate binding cavity. Due to these extensive differences, most isoflavones examined computationally for docking were unable to be reasonably fitted into the active site model of MtIOMT4. In addition, amino acid residues that potentially contribute to hydrogen bond formation in MsI7OMT (including Asn 310, Cys 117, Cys 313 and the neighboring Tyr 25) are not present in MtIOMT4.

Example 9

Expression Analysis of MtIOMT Genes

Figure 7:
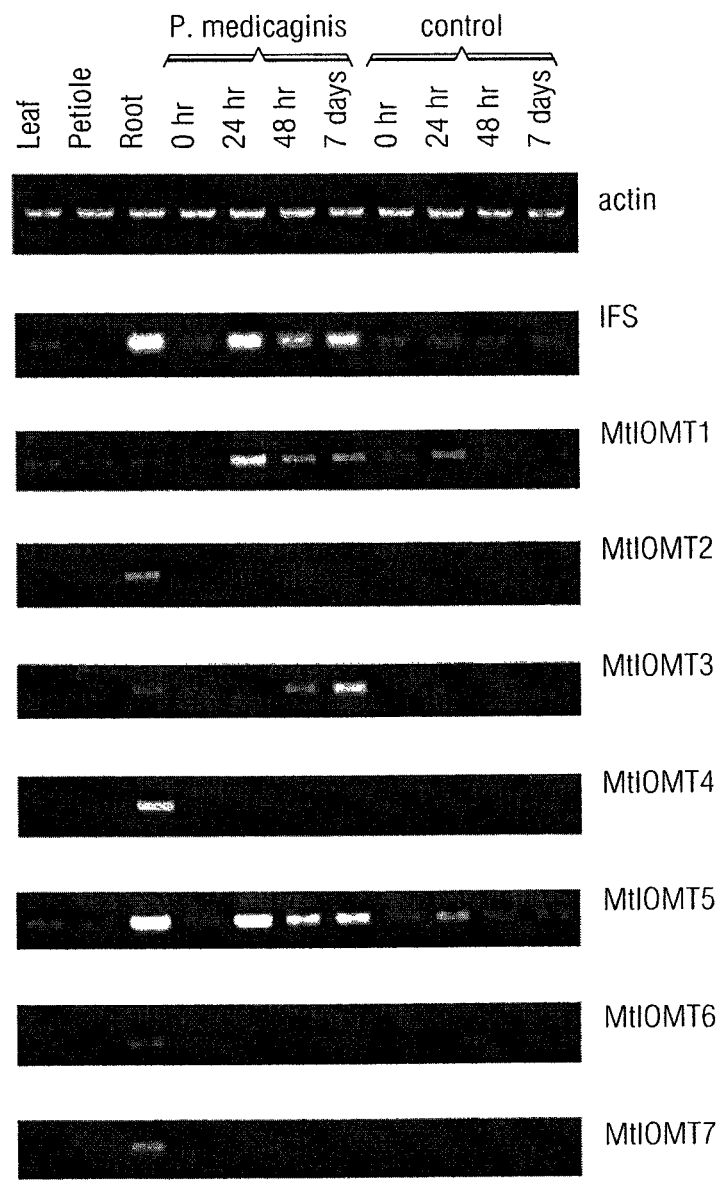
FIG. 7. Expression of MtIOMTs in healthy tissues of *M. truncatula* and in leaves infected with the leaf pathogen *P. medicaginis*. MtIOMT expression was determined by RT-PCR using primers specific for each MtIOMT. IFS, isoflavone synthase.

The expression patterns of MtIOMT genes in *M. truncatula* were examined by RT-PCR using primers specific for each gene (Table 1, FIG. 7). Most MtIOMTs, except MtIOMT1 and MtIOMT5, are primarily expressed in the roots of *M. truncatula*. MtIOMT1 has comparably low transcript levels in leaf, petiole, and root tissue. In addition to a significant level at root tissue, MtIOMT5 transcripts are also detectable in leaf and petiole.

The fungal leaf spot pathogen *Phoma medicaginis* is a known inducer of isoflavonoid biosynthesis in alfalfa and causes rapid increases in transcripts encoding isoflavonoid biosynthetic enzymes including MsI7OMT (Paiva et al., 1994; He and Dixon, 2000). Increased expression of three MtIOMTs is observed following inoculation of *M. truncatula* with *P. medicaginis*. MtIOMT1 and MtIOMT5 exhibit a similar induction profile to that of 2-hydroxyisoflavanone synthase (isoflavone synthase; IFS), with maximal transcript levels appearing 14-24 hours post-inoculation (FIG. 7). MtIOMT3 is also induced, although transcripts first appear 48 hours post-inoculation.

Figure 8:
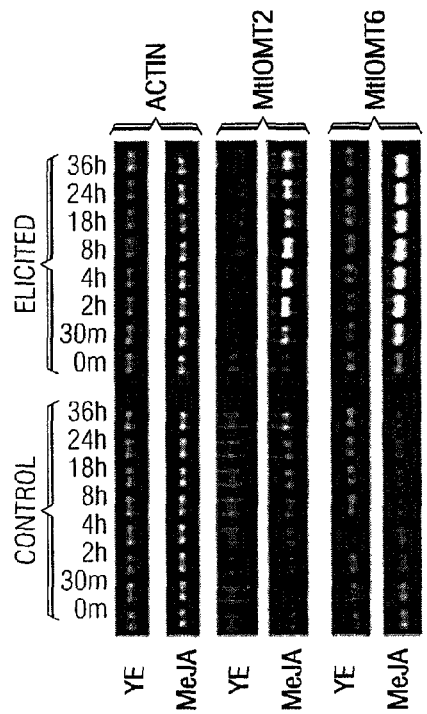
FIG. 8. Expression analysis of MtIOMT and IFS genes in elicitor-treated cell suspension cultures of *M. truncatula*. (a) Microarray analysis of seven MtIOMT genes in response to YE and MeJA treatment. TC numbers from TIGR MtGI v. 8/v.5 are given under the description. (b) RT-PCR analysis confirming induction of MtIOMT2 and MtIOMT6 by MeJA. (c) Microarray analysis of IFS expression in response to YE and MeJA treatment. The TC number is from TIGR MtGI v. 8. Note: for (a) and (c), numbers represent ratios of treatment vs. control samples. Ratios are coded according to the scheme at the bottom of the figure. Gray coded values had a "presence call" by the GCOS program (Affymetrix, Santa Clara, Calif.) in the higher expressed or both sample groups. The non-coded values indicate absence of a "presence call" in both control and treatment samples.

Differential induction of MtIOMTs in response to elicitation was also observed in *M. truncatula* cell cultures treated with yeast elicitor (YE) or methyl jasmonate (MeJA), which induce different global patterns of genetic re-programming (Suzuki et al., 2005). Changes in IOMT transcripts in elicited cells were inferred from microarray data generated utilizing Affymetrix Medicago genome arrays with 61K probe sets (www.affymetrix.com). Transcript levels for IFS and the MtIOMT 1, 2, 4, 5, 6, 7 and 8 present on the Affymetrix arrays were compared at 2 and 24 hours post-elicitation against corresponding control values (FIG. 8). MtIOMT4 was induced approximately 250-fold within 2 hours of exposure to YE, but was down-regulated by MeJA. MtIOMT5 was induced 4.6-fold by YE, but not by MeJA. In contrast, MtIOMT6 and MtIOMT7 were very strongly induced by MeJA, but only very weakly by YE (FIG. 8a). RT-PCR analysis confirmed the lack of induction of MtIOMT2 or MtIOMT6 by YE, and their strong induction by MeJA (FIG. 8B).

MtIOMTs 6-8 are annotated as encoding 2,7,4'-trihydroxyisoflavanone 4'-OMTs. 2,7,4'-Trihydroxyisoflavanone 4'-OMT is proposed to exist as the central enzyme in a metabolon also comprising IFS and 2,7,4'-trihydroxyisoflavanone dehydratase (2HID) (Akashi et al., 2000, 2003). Array data show that several IFS genes were slightly or moderately induced by YE, but consistently reduced by MeJA 24 h after treatment (FIG. 8C). Based on the array data, only MtIOMT4 and MtIOMT5 have similar expression profiles to that of IFS.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060; U.S. Pat. No. 5,302,523; U.S. Pat. No. 5,322,783; U.S. Pat. No. 5,384,253; U.S. Pat. No. 5,464,765; U.S. Pat. No. 5,508,184; U.S. Pat. No. 5,538,877; U.S. Pat. No. 5,538,880; U.S. Pat. No. 5,545,818; U.S. Pat. No. 5,550,318; U.S. Pat. No. 5,563,055; U.S. Pat. No. 5,591,616; U.S. Pat. No. 5,610,042
U.S. Patent Publication 20050150010
Abdullah et al., *Biotechnology*, 4:1087, 1986.
Akashi et al., *Biosci. Biotechnol. Biochem.*, 64:2276-2279, 2000.
Akashi et al., *Plant Cell Physiol.*, 44:103-112, 2003.
Altschul et al., *J. Mol. Biol.*, 215:403-410, 1990.
Asamizu et al., *DNA Res.*, 7:127-130, 2000.
Barnes, *J. Nutr.*, 134:1225 S-1228S, 2004.
Bates, *Mol. Biotechnol.*, 2(2):135-145, 1994.
Battraw and Hall, *Theor. App. Genet.*, 82(2):161-168, 1991.
Bevan et al., *Nucleic Acids Research*, 11(2):369-385, 1983.
Bhattacharjee et al., *J. Plant Bioch. and Biotech.* 6, (2):69-73. 1997.
Biocomputing: Informatics and Genome Projects, Smith (Ed.), Academic Press, NY, 1993.
Birren et al., *Genome Analysis*, 1:543-559, 1997.
Bisby et al., In: *Plants and their constituents*, Phytochemical Dictionary of the Leguminosae, Vol I, Chapman and Hall, NY, 1994.
Bower et al., *Plant J.*, 2:409-416. 1992.
Bradford, *Anal. Biochem.*, 72:248-254, 1976.
Buising and Benbow, *Mol Gen Genet*, 243(1):71-81, 1994.
Callis et al., *Genes Dev.*, 1:1183-1200, 1987.
Carillo and Lipman, *SIAM J Applied Math.*, 48:1073, 1988.
Casa et al., *Proc. Natl. Acad. Sci. USA*, 90(23):11212-11216, 1993.
Chandler et al., *Plant Cell*, 1:1175-1183, 1989.
Christou; et al., *Proc. Natl. Acad. Sci. USA*, 84(12):3962-3966, 1987.
Chu et al., *Scientia Sinica*, 18:659-668, 1975.
Computational Molecular Biology, Lesk (Ed.), Oxford University Press, NY, 1988.
Computer Analysis of Sequence Data, Part I, Griffin and Griffin (Eds.), Humana Press, NJ, 1994.
Conkling et al., *Plant Physiol.*, 93:1203-1211, 1990.
Coulson, *Trends in Biotech.*, 12:76-80, 1994.
D'Halluin et al., *Plant Cell*, 4(12):1495-1505, 1992.
DE 3642 829 A
Deavours and Dixon, *Plant Physiol.*, 138:2245-2259, 2005.
Dellaporta et al., In: *Chromosome Structure and Function: Impact of New Concepts*, 18th Stadler Genetics Symposium, 11:263-282, 1988.
Devereux et al., *Nucleic Acids Res.*, 12(1):387, 1984.
Dixon and Ferreira, *Phytochemistry*, 60:205-211, 2002.
Dixon and Steele, *Trends Plant Sci.*, 4:394-400, 1999.
Ebert et al., *Proc. Natl. Acad. Sci. USA*, 84:5745-5749, 1987.
Edwards and Dixon, *Phytochemistry*, 30:2597-2606, 1991.
European Patent Application 154,204
Ewing et al., J. Comput. Aided Mol. Des. 15:411-28, 2001.
Ferrer et al., *Plant Physiol.*, 137:1009-1017, 2005.
Fraley et al., *Bio/Technology*, 3:629-635, 1985.
Frick and Kutchan, *Plant J.*, 17:329-339, 1999.
Frick et al., *Phytochemistry*, 56:1-4, 2001.
Fromm et al., *Nature*, 319:791-793, 1986.
Gallie et al., *Plant Cell*, 1:301-311, 1989.
Gang et al., *Plant Cell*, 14:505-519, 2002.
Gelvin et al., In: *Plant Molecular Biology Manual*, 1990.
Ghosh-Biswas et al., *J. Biotechnol.*, 32(1):1-10, 1994.
Hagio et al., *Plant Cell Rep.*, 10(5):260-264, 1991.
Hamilton et al., *Proc. Natl. Acad. Sci. USA*, 93(18):9975-9979, 1996.
Harborne, In: *The Flavonoids, Advances in Research since 1986*, Chapman & Hall, London, 1994.
Harrison and Dixon, *Mol. Plant-Microbe Interact.*, 6:643-654, 1993.
Haseloff et al., *Proc. Natl. Acad. Sci. USA*, 94(6):2122-2127, 1997.
He and Dixon, *Arch. Biochem. Biophys.*, 336:121-129, 1996.
He and Dixon, *Plant Cell*, 12:1689-1702, 2000.
He et al., *Plant Cell Reports*, 14 (2-3):192-196, 1994.
He et al., *Plant Mol. Biol.*, 36:43-54, 1998.
Hensgens et al., *Plant Mol. Biol.*, 22(6):1101-1127, 1993.
Hentikoff and Hentikoff, *Proc. Natl. Acad. Sci. USA*, 89:10915-10919, 1992.
Hiei et al., *Plant. Mol. Biol.*, 35(1-2):205-218, 1997.
Hinchee et al., *Bio/technol.*, 6:915-922, 1988.
Hoffmann et al., *J. Biol. Chem.*, 276:36831-36838, 2001.
Hou and Lin, *Plant Physiology*, 111: 166, 1996.
Hudspeth and Grula, *Plant Mol. Biol.*, 12:579-589, 1989.
Ibrahim et al., *Phytochemistry*, 26:1237-1245, 1987.
Ikuta et al., *Bio/technol.*, 8:241-242, 1990.
Ishidia et al., *Nat. Biotechnol.*, 14(6):745-750, 1996.
Jones et al., *Acta. Crystallogr.*, A49:148-157, 1991.
Joshi and Chiang, *Plant Mol. Biol.*, 37:663-674, 1998.
Kaeppler et al., *Plant Cell Reports*, 9:415-418, 1990.
Kaeppler et al., *Theor. Appl. Genet.*, 84(5-6):560-566, 1992.
Katz et al., *J. Gen. Microbiol.*, 129:2703-2714, 1983.
Kim et al., *J. Biotechnol.*, 119(2): 155-162, 2005.
Klee et al., *Bio-Technology*, 3(7):637-642, 1985.
Knittel et al., *Plant Cell Reports*, 14(2-3):81-86, 1994.
Komblatt et al., *Biochem. Cell Biol.*, 82:531-537, 2004.
Kubasek et al., *Plant Cell*, 4:1229-1236, 1992.
Laskowski et al., *J. Appl. Cyst.*, 26:283-291, 1993.
Lawton et al., *Plant Mol. Biol.* 9:315-324, 1987.
Lazzeri, *Methods Mol. Biol.*, 49:95-106, 1995.
Lee et al., *Korean J. Genet.*, 11(2):65-72, 1989.

Liu and Dixon, *Plant Cell,* 13:2643-2658, 2001.
Lorz et al., *Mol Gen Genet,* 199:178-182, 1985.
Marcotte et al., *Nature,* 335:454, 1988.
Marti-Renom, et al., *Annu. Rev. Biophys. Biomol. Struct.,* 29:291-325, 2000.
Maxwell et al., *Plant J.,* 4:971-981, 1993.
McCabe and Martinell, *Bio-Technology,* 11(5):596-598, 1993.
McCormac et al., *Euphytica,* 99(1):17-25, 1998.
Murashige and Skoog, *Physiol. Plant.,* 15:473-497, 1962.
Nagatani et al., *Biotech. Tech.,* 11(7):471-473, 1997.
Needleman and Wunsch, *J. Mol. Biol.,* 48:443-453, 1970.
Noel et al., *Rec. Adv. Phytochemistry,* 37:37-58, 2003.
Odell et al., *Nature,* 313:810-812, 1985.
Ogawa et al., *Sci. Rep.,* 13:42-48, 1973.
Omirulleh et al., *Plant Mol. Biol.,* 21(3):415-428, 1993.
Otwinowski and Minor, In: *Methods in Enzymology: Macromolecular Crystallography,* Carter, and Sweet (Eds), Vol 276(A):307-326, Academic Press, NY, 1997.
Ow et al., *Science,* 234:856-859, 1986.
Paiva et al., *Plant Cell Tissue Organ Cult.,* 38:213-220, 1994.
PCT App. WO 9217598
PCT App. WO 94/09699
PCT App. WO 95/06128
PCT App. WO 97/4103
PCT App. WO 97/41228
Phillips and Kapulnik, *Trends Microbiol.,* 3:58-64, 1995.
Potrykus et al., *Mol. Gen. Genet.,* 199:183-188, 1985.
Preisig et al., *Plant Physiol.,* 91:559-566, 1989.
Reichel et al., *Proc. Natl. Acad. Sci. USA,* 93:5888-5893, 1996.
Rhodes et al., *Methods Mol. Biol.,* 55:121-131, 1995.
Ritala et al., *Plant Mol. Biol.,* 24(2):317-325, 1994.
Rogers et al., *Methods Enzymol.,* 153:253-277, 1987.
Sambrook et al., In: *Molecular Cloning-A Laboratoy Manual* (second edition), Cold Spring Harbour Laboratory Press, 1989.
Schroder et al., *Phytochemistry,* 59:1-8, 2002.
Schroder et al., *Phytochemistry,* 65:1085-1094, 2004.
Sequence Analysis in Molecular Biology, von Heinje (Ed.), Academic Press, 1987.
Sequence Analysis Primer, Gribskov and Devereux (Eds.), Stockton Press, NY, 1991.
Sheen et al., *Plant Journal,* 8(5):777-784, 1995.
Singsit et al., *Transgenic Res.,* 6(2):169-176, 1997.
Spencer et al., *Plant Molecular Biology,* 18:201-210, 1992.
Stalker et al., *Science,* 242:419-422, 1988.
Sullivan et al., *Mol. Gen. Genet.,* 215(3):431-440, 1989.
Sutcliffe, *Proc. Natl. Acad. Sci. USA,* 75:3737-3741, 1978.
Suzuki et al., *Planta,* 220:698-707, 2005.
Thillet et al., *J. Biol. Chem.,* 263:12500-12508, 1988.
Thompson et al., *Euphytica,* 85(1-3):75-80, 1995.
Thompson et al., *Nucl. Acids. Res.,* 22:4673-4680, 1994.
Thompson et al., *Nucleic Acids Res.,* 25:4876-4882, 1997.
Tian et al., *Plant Cell Rep.,* 16:267-271, 1997.
Tingay et al., *Plant J.,* 11(6):1369-1376. 1997.
Tomes et al., *Plant. Mol. Biol.* 14(2):261-268, 1990.
Torbet et al., *Crop Science,* 38(1):226-231, 1998.
Torbet et al., *Plant Cell Reports,* 14(10):635-640, 1995.
Toriyama et al., *Theor Appl. Genet.,* 73:16, 1986.
Tsukada et al., *Plant Cell Physiol.,* 30(4)599-604, 1989.
Uchimiya et al., *Mol. Gen. Genet.,* 204:204, 1986.
VanEck et al., *Plant Cell Reports,* 14(5):299-304, 1995.
VanEtten et al., In: *Phytoalexins,* Bailey and Mansfield (Eds), Blackie, Glasgow, 180-217, 1982.
Vasil et al., *Plant Physiol.,* 91:1575-1579, 1989.
Walker et al., *Proc. Natl. Acad. Sci. USA,* 84:6624-6628, 1987.
Wang et al., *Molecular Cell. Biol.,* 12(8):3399-3406, 1992.
Wengenmayer et al., *Eur. J. Biochem.,* 50:135-143, 1974.
Yamada et al., *Plant Cell Rep.,* 4:85, 1986.
Yang and Russell, *Proc. Natl. Acad. Sci. USA,* 87:4144-4148, 1990.
Yang et al., *J. Mol. Graph. Model.,* 23:77-87, 2004.
Zheng and Edwards, *J. Gen. Virol.,* 71:1865-1868, 1990.
Zhou et al., *Plant Cell Reports,* 12(11). 612-616, 1993.
Zubieta et al., *Nature Struct. Biol.,* 8:271-279, 2001.
Zubieta et al., *Plant Cell,* 14:1265-1277, 2002.
Zukowsky et al., *Proc. Natl. Acad. Sci. USA,* 80:1101-1105, 1983.

What is claimed is:

1. An isolated nucleic acid sequence selected from the group consisting of:
   (a) a nucleic acid sequence encoding the polypeptide of SEQ ID NO:9;
   (b) a nucleic acid sequence comprising the sequence of SEQ ID NO:2;
   (c) a nucleic acid sequence encoding a plant isoflavonoid O-methyltransferase that hybridizes to the full-length complementary sequence of SEQ ID NO:2 under conditions of 0.15 M NaCl and 70° C.; and
   (d) a nucleic acid sequence encoding a plant isoflavonoid O-methyltransferase, wherein the nucleic acid sequence has at least 90% sequence identity to the nucleic acid sequence of SEQ ID NO:2, wherein the isolated nucleic acid sequence is operably linked to a heterologous promoter.

2. A recombinant vector comprising a nucleic acid sequence operably linked to a heterologous promoter, wherein the nucleic acid sequence is selected from the group consisting of:
   (a) a nucleic acid sequence encoding the polypeptide of SEQ ID NO:9;
   (b) a nucleic acid sequence comprising the sequence of SEQ ID NO:2;
   (c) a nucleic acid sequence encoding a plant isoflavonoid O-methyltransferase that hybridizes to the full-length complementary sequence of SEQ ID NO:2 under conditions of 0.15 M NaCl and 70° C.; and
   (d) a nucleic acid sequence encoding a plant isoflavonoid O-methyltransferase, wherein the nucleic acid sequence has at least 90% sequence identity to the nucleic acid sequence of SEQ ID NO:2.

3. The recombinant vector of claim 2, further comprising at least one additional sequence chosen from the group consisting of: a regulatory sequence, a selectable marker, a leader sequence and a terminator.

4. The recombinant vector of claim 3, wherein the additional sequence is a heterologous sequence.

5. The recombinant vector of claim 3, wherein the promoter is a developmentally-regulated, organelle-specific, inducible, tissue-specific, constitutive, cell-specific, seed-specific, or germination-specific promoter.

6. The recombinant vector of claim 3, defined as an isolated expression cassette.

7. A transgenic plant transformed with the recombinant vector of claim 2.

8. The transgenic plant of claim 7, further defined as a monocotyledonous plant.

9. The transgenic plant of claim 7, further defined as a dicotyledonous plant.

10. The transgenic plant of claim 9, further defined as a legume.

11. The transgenic plant of claim 7, further defined as an $R_0$ transgenic plant.

12. The transgenic plant of claim 7, further defined as a progeny plant of any generation of an $R_0$ transgenic plant, wherein said progeny plant has inherited said recombinant vector from said $R_0$ transgenic plant.

13. A plant part of the plant of claim 7, wherein said plant part comprises the recombinant vector.

14. A seed of the transgenic plant of claim 7, wherein said seed comprises said recombinant vector.

15. A host cell transformed with the recombinant vector of claim 2.

16. The host cell of claim 15, wherein said host cell is a plant cell.

17. A method of increasing flavonoid biosynthesis in a plant, comprising introducing into said plant the recombinant vector of claim 2, wherein the nucleic acid sequence encoding isoflavonoid O-[ ]methyltransferase is expressed to increase flavonoid biosynthesis in the plant grown under stress conditions relative to a plant of the same genotype lacking the recombinant vector and grown under said stress conditions.

18. The method of claim 17, wherein the recombinant vector is inherited from a parent plant of said plant.

19. The method of claim 18, wherein the plant is an $R_0$ plant transformed with the recombinant vector.

* * * * *

UNITED STATES PATENT AND TRADEMARK OFFICE
CERTIFICATE OF CORRECTION

PATENT NO. : 8,809,627 B2  
APPLICATION NO. : 11/840032  
DATED : August 19, 2014  
INVENTOR(S) : Bettina E. Broeckling et al.

Page 1 of 1

It is certified that error appears in the above-identified patent and that said Letters Patent is hereby corrected as shown below:

In the Claims,

Column 78, Line 48, please delete "O-[ ]methyltransferase" and please insert --O-methyltransferase--

Signed and Sealed this  
Third Day of February, 2015

Michelle K. Lee  
*Deputy Director of the United States Patent and Trademark Office*

SEQUENCE LISTING

<160> NUMBER OF SEQ ID NOS: 32

<210> SEQ ID NO 1
<211> LENGTH: 615
<212> TYPE: DNA
<213> ORGANISM: Medicago truncatula

<400> SEQUENCE: 1

```
aaacaaacaa aaaatccact tgcaaaataa tggcttcatc aatcaataac cgaaaaccaa      60
gtgaaatttt taaagcacaa gctttattat acaaaaacat gtatgccttt gtagattcta     120
tgtctctgaa atggtcaatt gagatgaaca taccaaatat tatccacaat catggcaaac     180
caattactct ttcaaactta gtttcaattc ttcaaattcc atcaaccaaa gtcgataacg     240
tgcagcgtct catgcgttac ctcgcacaca atggattctt tgagataatt acaaatcaag     300
aattagaaaa tgaagaagaa gcttatgctc tcactgttgc ttcagagctt cttgttaaag     360
gaactgaact ttgtttagct ccaatggttg agtgtgttct tgatccaaca ctttcaactt     420
catttcataa cttaaagaaa tgggtttatg aggaagatct cactctattt gctgtcaatt     480
taggttgtga tttatgggag tttcttaaca aaaaccctga gtataataca ttatacaatg     540
```

| | |
|---|---|
| atgctttggc tagtgattcc aaatgattaa tttggcaatg aaagattgca atttggtgtt | 600 |
| tgagggggttg gaatc | 615 |

<210> SEQ ID NO 2
<211> LENGTH: 5875
<212> TYPE: DNA
<213> ORGANISM: Medicago truncatula

<400> SEQUENCE: 2

| | |
|---|---|
| aagtgacctc gttccaaggg atttctgggc tgctggttcg gtggtgtccg aaacttggtt | 60 |
| ggtatgtata acgaatggtt gcaagaattt tttgatttta acctactaaa tttagagttc | 120 |
| tgctggactt ttgggttctg agcttatgac ggcttgtgag cctgagactc tcggggagtg | 180 |
| cgtttatttt ccttccctgg ataccttggc cttgactttg tttggaatcg aaggtaggag | 240 |
| ttgtcttatt tcttatcact tgttggcagt ttatgtctac taattagtgg gcccccttcta | 300 |
| gtcggggctt acgggtcttt gatccctcgc tatagagtcc tggcacccat tattattacg | 360 |
| aattttggt gtgtcacaaa atagtttgcg acgagatttt ccccttttg cgacggattc | 420 |
| ttggtgtaac taaaagtgtg ttttttagtag tgttcctaag gttgactatt gaactttcta | 480 |
| tactgccaaa taatggtcaa agaaaacgtt aattattgtc acaaaataac tgattgtgtt | 540 |
| gtcagatatc caaacatatg gaggttttat aaaattcatc atccttcgta tgacaatcat | 600 |
| attgagccgc caggcgatgt gaagccttca catctgctcg tcgccctaca tcgggtgact | 660 |
| caagcagcat gcttccccta actatgttac tgtttaacgg tgttttttggt aaacaaatac | 720 |
| cgactggtgt ttattataac aagaaggacc aatccagaga tcctagtaca tgttgtgcat | 780 |
| tcgtttggtg tttgttcgtc gagttcgtag gttgcttaac gaacgagact agaccatgtg | 840 |
| gcgtcttttg acaggtttta atgcattaat aagtttaaa ttgcagaaac ttaaagaaaa | 900 |
| atacaaatgc aagtgcatta agataaaac tagttcgaca aatcctttac atacattctt | 960 |
| tatgactctt ttctctcgcg tcgatacttc gagtgtttta gaattctcta taggcgattt | 1020 |
| gcgacccgtt ttccctatgg aaatctaata tttatacata gcaaaatagc tggaaaaagc | 1080 |
| ctaacttcac gatcaacact tcttccatgt acacaaccgc ttgtctccct tgttctccct | 1140 |
| tgaggaaacc gcttctcttt tgaaattcga atcttcccgc cccaaaggca attgcttgac | 1200 |
| ttcgacgact tcactacttt ttatgtatct tgttgaactt caatgcttca agactcttta | 1260 |
| cgctaggtcc aacatctcgt cgaactcttt tgattgaagg aaatactttg atacctgcaa | 1320 |
| aattataagt caactaatgt tgaacacatt aaataaggca ggtgaaaata ccagctaaca | 1380 |
| gttacaaatc gtggtcaggc gaccgccaaa caaagataac aaaagttgct ctcagtgact | 1440 |
| tattgtactt ttccactcaa ctatgatcaa cctattaagc ttaacaaatg atgcaaataa | 1500 |
| aatggaaaga attatctggt tagggagaaa ttattaccat aaaaaatcta attgatataa | 1560 |
| aaaaaataaa agcaaaaata ttaacaaaaa ttcctagcta taaccaaaat tgcaatatac | 1620 |
| tacaacaaat aagactaaga tgacaataaa agacactaat aagtcattct tgataaagag | 1680 |
| ttatcagtac ccgatcatgt cttctaattt ttttattttt tttttgtgaa caaactctaa | 1740 |
| ttgattgtta atttagggggg ctatatgttg acaaaacttt tttgtattat attacatgtt | 1800 |
| ttttttttggg ttcgtagtat attccatgtg caattatagt ataataatat cttgtcgctc | 1860 |
| taggttgata aaattagtac gtagtgtatt acatcacatt acatgttgca attatagtat | 1920 |
| aaaaataaga gtaatgtgtt ggtctataaa ctgaatcaaa ttctgaaata caccaaaaca | 1980 |
| aaattttcat ttgcaggtgt atggcttctt caataaataa ccgtaaagca agtgaaattt | 2040 |

```
tcaaagcaca agctctatta tacaaaaaca tgtatgcttt catagattcc atgtctctta    2100
aatggtcagt tgaaatggac ataccaacta ttatctacaa tcatggcaaa ccaattactc    2160
tttcaaactt agtttcaatt cttcaaattc catcaaccaa agtcgataac gtgcagcgtc    2220
tcatgcgtct ccttgcacac aatggattct ttgagatagt aacgaatcaa gaattggaaa    2280
atgaagaaga agcttatgct ctcacagtta cttcagagct tcttgttaaa gggactgaac    2340
tttgtttagc tccaatggtt gagtgtgttc ttgatcctaa atttaatgtt tcatttcata    2400
atttcaagaa gtggatttat gaggaagatc tcaccctctt tgctacctct ttaggatgtg    2460
atttatggga gtttcttaac aaaaatcctg aatataatag attgttcaat gatgctatgg    2520
ctagtgattc caaaatgatt aatttggcat tgaaagattg caattttgtg tttgaggggt    2580
tggattcaat tgtggatgtt ggtggtggaa atggaacaac tggtaagatt atttgtgaga    2640
catatcctaa gttgagatgt gttgtttttg atcgtccaaa ggttgtagag aatttatgtg    2700
gaagtaacaa tttgacatat gtcggtgggg acatgttcat atctgttcct aaagctgatg    2760
cagttctgct taaggtatgc ttttctaaac tatatttac ctctgtcact ttattttaaa     2820
attcatattt atttacctc tcgagataaa ttagtagtat tcgtgatggg tgatcatgtg     2880
cgaacttgca tagtataaga agttaaaaat agtaaagtgt ctagtaattt aaaatagagc    2940
ttgtaagttt ttttttgaga taatttgtct tgtaaggagg ctttgtatat aatttaaatt    3000
aaaagaaaa attggaaaga caaaattatt attaataatg ttgatgacta caccctatac     3060
atttactttc tttgacttt tattttagtt atatatgtga ttgaagtagt atttcacaat     3120
gtgcgatgct atatatcccg agagaatttg tctcgagggg atcgtgaaac aacatttagc    3180
caataaactt acttactggc cggaaagcat gggatgtcat gggtataatt ctgaaaagac    3240
ttttattaaa tatggactcg tgaattattc gtgagactat ttttcgctat aagcaacaat    3300
atccgttcac atttgtttca cgtgagattc aaactctact ccttgagatt atgaagttaa    3360
actcttacca ttgacttgac aaatctttga aagacatgtt tataatcaat tgcaaattta    3420
gtactttttc tgaaatctga aactatgagt taagcacttt ccagatgaag ttattaaaga    3480
tcatttgaaa atttaattga gtccgtaact catttatcac aaagttatta gggaaattta    3540
taatatttct tctcttgctt tttgttactt tgcagtggat tttacatgat tggacggata    3600
gggattgcat aaagatattg aagaaatgta aagaagctgt tacaactgag gggaaaagag    3660
gaaaagtgat tgtgatagac atggtaataa atgaaaagaa agaagagaac gaacttactc    3720
aaataaagct cctaatgaat gtaacaattt catgtctaaa tggaaaagag agaaatgagg    3780
aagaatggaa gaaactcttc atggaagcag gctttgaaaa ctacaaaata tctccttgta    3840
ctggattatt gtctcttatt gagatctatc cttaaaacac taatgtgaac ttaataaatt    3900
tgtaatgttt ggttctgttt gatccagatt tgttatgttt tatgacatag gtttgttgct    3960
cttctccgat tcgtcatccc ttggatttgc attattgggt tgatattaca gaatctggaa    4020
ttggttcgtt tggtgggctt cattgcaagt cgtttcgcgc aacttcagct ttgtaccgtt    4080
aattttccgg gttgttgctt cattgttcca ctgttatgtg ttaactgatg ttcgatgctg    4140
tttctttgaa agtgtgtata caatctgtgg ttggtgttcc agatcgttg agatttacag      4200
gttttaaggt taaggtctac ctccttcgag caggtgtcgc tttaatatcc gtatttgtcc    4260
tcgtgattga ttttaaactg ttttgatatc ctcgttcttc tatctatttg atgttggatt    4320
gtttgtctgt acagatcgtt tgtgtgttgt tgttttaggg ggttgttggt tcttgcatcc    4380
```

```
attctgtgtt gacggtcggt caattctctt gtctatagac ctttgattag tactcttttg   4440
atgcaggttg ttttctgcaa ggtttcacca cgtttggctg cgttttcaag gatggtccat   4500
atagtgtata tttctcagcc tgcaagaagg aggaagtgag tactgaacct gttctggctg   4560
aagctctagc tacccgttgg tgtcttcatt tagcaaagga aaaaggtctt caagatgtta   4620
taattcaatc tgatgctctt gctgttgtta agtgttttag aggttctaac tctcttgcta   4680
gtattgattt tatagtctta gattgtaagg cccttatgaa agattttagt agtgtgtctg   4740
ctaactatgt ttgtagaaac ttaaagctca tagacttgtt ggccatgcta tgcaagctgg   4800
ttgcaattcc tgggtaggat atgcctttcc tactgttagt tctgctaatg tttgtaatgc   4860
tactgtttgt aacacttctg ccatttaatg aagttgtttg aatttcaaaa aaaaaaaaat   4920
atttgtatta cttgtttggg ttgacctaca cttttacttg gatttattga gttagatttt   4980
atgtcccgtt atatatatat atatatatat atatatatat atatatatat atatatatat   5040
atatatatat ataggggt gctactaatt ggaatgtcca attaaacact tcggtgcatg   5100
ttaatagttt taacttgtgt gtattacatt tgcttagtac tcatcctagt tttcctattt   5160
tgtaggacaa taatgggtag agtcggttat tggaaaataa atttgttgtg ttttattcct   5220
cttttggttc cttgattatt gaatgagtta ccatttttata ttcattactg caatgttttt   5280
tttttttttt gtcaggtaac ctagtggcta gaattcactt tataaggtga ataagtgggg   5340
tgtccggggt tcaaaccccg gcccttgcat ataacaatac atttgtccctg ccaactgagc   5400
tatgctcacg gggactcatt agtgcaatgt tatgccacat atacatgaat tatattaatt   5460
aagattgaca tttgaaatta accaagctta caaccttgat ataattgttt taaggcttaa   5520
tacatctcct gatcccttaa cttattttat tttctcagtt tgatccctta actataaagt   5580
gtgtcaattt ggtctcacaa gtcttttgcc gttatctact ttaatcctca caattagttt   5640
tttgatggat aatattttta atatgattat aaccgttaga ttgaaggtcc atagtatatt   5700
acagtgaacc acacatatct aattttttc ccttctattc ttctcctttc ctgttcttcc   5760
tcttgatctt aatcatcttc aacattgttc atataaaacc cagaaaattt cttcatcaca   5820
attagcaaca acatcaacct tttcataact ataatcacct agatctcaat ttcaa       5875
```

<210> SEQ ID NO 3
<211> LENGTH: 5702
<212> TYPE: DNA
<213> ORGANISM: Medicago truncatula

<400> SEQUENCE: 3

```
ggcatatcat tttgaacgac ttccctctgc gattgccatg gttgtgagac cttgaggctt     60
gatgataggt tggtcttcgc cgaccattct tttcgagatc gccgggaggg ttttaggttt    120
atgagaatgt cctaggttag ttttagcaag gtttccacag acggcgtcaa ctgtacttgc    180
agtgagtaca ataatagaat ttaaggttta gattgtttat gtgatgcctt gagaatgctc    240
tcaagaggtg tatttatagc cctccgtggg cttggttttc cgtgatgaaa accccaagta    300
atgtgggctt taagtctttt tacagagttc tagatgcttc tagaagttag ttgaggcgac    360
gcctcttgga gggcgtctaa ggcttatgag ctcttctgga gggcgcctta acctttctgg    420
agagtgatga gataaaaccg caagtgcacg gtcttaccga agtagtaaaa taagagtatc    480
gttccgacag ggagttatga attcaattat cttttaacaa tgattaaaat taagtatag     540
aaagtagaaa gttgtatttt tatatattta aaaggaaata ataataaaag ataaaagcct    600
tggaatcatt ggttcatcct aatgacaagt ccttcacaaa ccaaactatt aaacttataa    660
```

```
ccttatgtta gacctaattt ctcaagacag tttctcttat gttcctctag caaccaagcc    720
tatttcgctg acttgattac tattagattt tggttcctct aacaatcaag cctatttcgc    780
tgacttgatt gttattagtt cccttgaaga tcgaaactat atgtctcaaa gattgcaatg    840
caaagcctat ttcgctgact ttgcaatcct tgtctaaatt cacttgttcg aatatcaaag    900
ctccactttc gttttatgaa ttgatatttg agatgatgga taaacaatta tcaaaccctc    960
cactttcgtt tctacagttt gataatggtt gatccatgtt aaagcggtga atttagataa   1020
ggaattaggg ttacataaga ttaaggttta aagcttggtt tgattaggat tatgtcatta   1080
gacttatcca acaatcccaa gacaagagaa gtctactcac tgacgttcat cgtagacaag   1140
gggaagaaga gagaaagcat aaagataaat aacaagaaag taaaatgaac ttttattaga   1200
aagacaattg tcacatattg tattccaaga aaagatgaat atttgtgatg gctagctact   1260
ctatttatag tacacaattg acttcaaatc taagcaagta tattccaaga atattccacg   1320
gtagattgtg cgccaagata gaatagctta gagcccaagc aaaagcagca aaggtcttc    1380 tggagggtgg cacggccgtg ccaaggctag cacgggccgt gccaggcttc tgacttgtgg   1440
aagacatatt ttgtctccca atcttcatat tttcgtgtcc aatctgctcc aaatcccttt   1500
cttttgctcc aagactcaat ccatccaata ttcttccctg aaatataata aattgcaatt   1560
taaagtaaac tatcctaaaa aggaaataat actaatataa aattatataa aatctaaata   1620
aaactaaact aaaaagcata ttaaaatagt atataaatga ctcatcagag agcattcgaa   1680
cccttaggaa tatattgaga atctaataag cgagagacat cccttatcta caatacagtt   1740
ttattaggtt gagttaaaca taaaatgtaa taataattac atcgccttac atgtgcattt   1800
cttgcgacaa ttcaataatc aatcgtcata ctttttttat aagaagtcaa tattcatagt   1860
tcaaacaaac aagacttatt gagctgctga gtgatctcac ataatgaaaa tagggtgctt   1920
aaactttact atataaagca aatcaaattc taaaacctca caaagacata aaaacaaaca   1980
aaaaatccac ttgcaaaata atggcttcat caatcaataa ccgaaaacca agtgaaattt   2040
ttaaagcaca agcttttatta tacaaaaaca tgtatgcctt tgtagattct atgtctctga   2100
aatggtcaat tgagatgaac ataccaaata ttatccacaa tcatggcaaa ccaattactc   2160
tttcaaactt agtttcaatt cttcaaattc catcaaccaa agtcgataac gtgcagcgtc   2220
tcatgcgtta cctcgcacac aatggattct ttgagataat tacaaatcaa gaattagaaa   2280
atgaagaaga agcttatgct ctcactgttg cttcagagct tcttgttaaa ggaactgaac   2340
tttgtttagc tccaatggtt gagtgtgttc ttgatccaac actttcaact tcatttcata   2400
acttaaagaa atgggtttat gaggaagatc tcactctatt tgctgtcaat ttaggttgtg   2460
atttatggga gtttcttaac aaaaaccctg agtataatac attatacaat gatgctttgg   2520
ctagtgattc caaaatgatt aatttggcaa tgaaagattg caatttggtg tttgaggggt   2580
tggaatcaat tgtggatgtt ggtggtggaa atggaacaac tggtaagatt atttgtgaga   2640
catttcctaa gttgacttgt gttgtttttg atcgtccaaa ggttgtagag aatttatgtg   2700
gaagtaacaa tttgacatat gttggtgggg acatgttcat atctgttcct aaagctgatg   2760
ctgttttgct taaggtatgc ttttctaaac taagatattt tttctcagtc actttgtttt   2820
aaaattctaa ttttaggcc ctttagaatt ttcaatccta aaattgttgt gtagcaaaac   2880
catcataatg tttatgtcat gtcaagaaaa aacttactag gtcaccactt ttggatgcta   2940
aaacatgagc aggaccaaaa gcataattta aaaaaatgaa aaatttaaaa tgataaatgg   3000
```

```
gaaagataaa gttattatta ataatgttga cactaatttt agaagttttt ttcttctttt    3060
attttgtgtt aatcctgcgg tgtttaggaa aaagagccct cataattcga agattgatgg    3120
gagataaata aactccgaca aaaaattgtt acatctagaa attgaactca ggttctctta    3180
aacaattgct tagttactaa attccttgct tactttttatt ttttaaaact acaagtattg    3240
cttggttact tttttttttt aaaactacaa gttgatcagt ttacatatga agttatgaaa    3300
gataatttga aaatttattt atttgagtct gtaattcaat tcacataaag ttattaagga    3360
aatttatagt ttttcctcta ttgctttctt ttcctttgca ggcggttttg catgattgga    3420
ctgataagga ttgcataaag atactaaaga aatgtaaaga agctgttaca agtgatggaa    3480
aaagaggaaa agtgattgtg atagatatgg taataaatga aaagaaagat gagaaccaac    3540
ttactcaaat aaagctactc atgaatgtta caatttcatg tgttaatgga aaagagagaa    3600
atgaggaaga atggaaaaag ctctttatag aagcaggctt ccaagattac aaaatatctc    3660
cttttactgg attaatgtct cttatagaga tctatcctta aaatactaat ggtttaatcc    3720
atttagtagt ttacatgctg ttataacaaa ataaattttat aataagcaca acccatttgg    3780
gttggtctgg tggtattggc ttgggatctt gaagtgtgct cctttttgaag atcttaggtt    3840 cgattctcca gcacttgatt gatgttgtga acttaataaa gtcacatgtc ttatgataat    3900
ttggggaaga aagacactga ccttgacttg tgtgattttc ttggacctaa attgtgatgt    3960
ttcctttgta taaattttga ttttcgtatt ttgtaccaca ataatagcaa gagcaagtta    4020
ttgataaaac aaatgttggt gttttattgc tcttttgtta ccttgatatg aattatgatt    4080
taaccactct atattcaaag atttgcatat gcaagatttt gactcatata gtatgaaatg    4140
aatcaaattt cattcattga ttgattcaag tgataaaaac atactcttaa aaattgggcc    4200
ggactggccg gtccgatcgg ttagattgga aaccggacaa tcctgcatta cattaactag    4260
accgatcatg caattgaatt gttagagttt cttgaaccga tcaaattcgc atataccgat    4320
ggctccagtt caacgaaaac aatcagtgc tattatttaa agggtatgtc taacatgtgt    4380
aatattgcac atgttaaagg aactaaaagt agtaacttt tgttgttggt ctagtagcct    4440
agtggctcga gctcatgcat atatatgtgg agatgtgggg tgtatgggt tcgaactccg    4500 acccctgcat aaaattatgca atgtccatac cagttgattt aacctcttgg ggacctggaa    4560
aatattaatt aaaaattata taatatgaag cacaagtttt gatacaatat tactttttta    4620
aacttcctaa catgaggtgc tataattaat tgggcagcgc tataattaat tgacttccta    4680
gctgtatttg tagaaaacac gggaaaccaa ccaatcatat agcctttgta ttacctcgca    4740
acattcaaca tttccgtatt taaaggaatg catgttgaaa gtgtctagtg tagaatatat    4800
accaatatat tttaagaaca attgagtagt ggttgaacaa gtaactgagt tcagttgttt    4860
ctcatataaa attattgacc ctaaagatat agtaggaaaa tcatggcaca attcttcctg    4920
ggtcttagta ctatataaga cttcattttt caattgtctt agtactatat aagacttcat    4980
ttttcaatta ttttagtggc ttaaagatag agaatcttga taaccaaatg gggaaacttt    5040
tcaagtaaaa aggttaaggg ttaagtgtct ttaggtgaga ttttgggtt gataaatact    5100 tcacaaatat cttgggtagt gatatctcat ttgagaaagg atgaaaagc tttcttaat    5160 atgttttctg ttatgattca ttatgggttt gaatgacttg aaaataagt agaaattatg    5220 atttgttctt tgtgagttgg aatctacttt cttgtaacca ctttgtatta gtcatatcat    5280
agtggattgg agagttattc tctcccctag gtgtaggata aatttatccg aactggattt    5340
tatcttctct cttaaccttg ttgctttgtt atgcttctct cttaaccttg ttgttttaca    5400
```

```
cttctttgat tttgattact ctttccttta ctccacatat aatataaatt tatattggta    5460
tgatttttaa gtctcgaatt cgcaacactt ttacttatga ttttaagcaa accctgaggc    5520
cctgtctatc cccccaattc tacacattct aatgaataaa ttttttaaaa atatttgacg    5580
aatctcacaa gtcactcctt atttatgcac ttaaatcata atataattca ctactaaatt    5640
gtgatctcaa attaattata agccaaacaa cccttagcct ttttacttaa ttgtatttaa    5700
tt                                                                   5702

<210> SEQ ID NO 4
<211> LENGTH: 1257
<212> TYPE: DNA
<213> ORGANISM: Medicago truncatula

<400> SEQUENCE: 4
accaatttaa acataactaa atatcaattg tagtattatg gcttcaacaa ataaccagtt      60
agaagcaact gaacttttg aaggccaatc tctcttatac atgcacatgt ttggttttct     120
aaaatccatg gctcttaaat gggctattca actaaacatt ccagacataa tctacaacca     180
tggaaaacct attactctct ctgacttagt ttcaactcta caagttccaa tatctaaaca     240
aagtcttgtg gaaagactca tgcgttttct agcacacaat ggaatatttg taatccatga     300
gaaaggtgaa aatgatgatg atgatgatca agcatatgct ttgactcctg catcaaaact     360
cctttcaaaa tcatgttgca agaccattg tttaacacca atggttctta tgtctactga     420
tccaattttg atgggtaaat ttcatcaatt gggtgattgg atttgtggag aaattccaac     480
tttatatgag gcagctttag gatcaactgt gtgggaattt cttgagggaa aacctgaata     540
tttgagtctg tttaatcagg ctatggctag tgattctcaa atggtgaatt tggctttgaa     600
aaattgtagt aaggtgtttg aagggattga ttctattgtg gatgttggtg gtggaactgg     660
aaccacagct agaattatat gtgaggcttt tcctaagttg aaatgtgttg tttatgatct     720
tccacaggtt gtagcaaact tgtcatcagc atgtgataat ttaagttacg ttggtggaga     780
catgttcaaa tctatccctc aagctgatgc aattatgcta agtggatttt tacatgactg     840
gactgatgaa atatgcataa agattctaaa aacttgtaaa gagtctgttt caagcaacgg     900
caaaaaagga aaagtgatta ttatggatat aataataaat gaagaggatg atgagaaaga     960
tatgactgaa acaaagttat gtttggattt aatcatgatg gggattaatg gaaaagagag    1020
aactggaaaa gaatggaagc acctcttcgt tgaagcaggg ttcaaagact ataaaatatt    1080
tccattattt gaaaatagat ctcttattga agcttatcct taattaggca tattgatacg    1140
gtcgtatgga tttggtagtt tttacatgtt atgaattgaa taatgttttt tgccatttgg    1200
taacactttt atgtttttta catgatactt atagcgacaa tctttttcac gaaaaaa      1257

<210> SEQ ID NO 5
<211> LENGTH: 1478
<212> TYPE: DNA
<213> ORGANISM: Medicago truncatula
<220> FEATURE:
<221> NAME/KEY: misc_feature
<222> LOCATION: (1457)..(1457)
<223> OTHER INFORMATION: n is a, c, g, or t

<400> SEQUENCE: 5
atataacatt tgaaacatat aaaaaggtcc acactatagt ttatttcttc atatccattt      60
ccatcataac acatcaatca cataaacaaa gttcaccccc aaaacaaaca gcaaaaagag     120
```

-continued

```
agaatagaaa tggctttcag taccaacggt tctgaagaaa gtgaactgta tcatgctcaa      180
atccatttgt acaaacatgt atacaacttt gttagttcca tggctctcaa atcagccatg      240
gaactaggca tagctgatgc aattcacaac catggaaaac caatgactct ttctgaacta      300
gcctcatctt tgaaacttca cccttctaaa gttaatatac ttcaccgatt cttacgcctt      360
ttaacacata atggtttctt tgcaaaaaca atagtgaaag gcaagaagg agatgaagaa       420
gaagaaatag catattctct cacacctcct tcaaagcttc tcataagtgg aaaaccaaca      480
tgtttatctt caattgttaa aggagcactt catccaagtt ctttagacat gtggagttcc      540
tcaaagaaat ggttcaatga agataaggaa caaacattgt ttgagtgtgc aacaggggag      600
agttttggg attttcttaa caaagattct gaatctagta ctttgagtat gtttcaagat       660
gctatggcat ctgattctag aatgtttaag cttgttctcc aagagaataa acgcgttttc      720
gagggtttgg agtctcttgt tgatgttgga ggtggtactg gtggtgttac aaaactcatt     780
catgaaattt ttcctcacct taaatgtact gtttttgatc aaccacaggt tgttggtaac      840
ttaactggaa atgaaaattt gaactttgtt ggtggagata tgttcaaatc tatcccttct     900
gctgatgctg ttttacttaa gtgggttctg catgattgga atgatgaaca atccttaaag     960
atattgaaga acagcaaaga agctatttca cacaaaggaa aggatggaaa agtgattatc     1020
attgacatat caattgatga aacaagtgat gaccggggat taactgagtt gcaattggac    1080
tatgatttgg tgatgcttac aatgtttctt ggtaaagaaa gaacaaagca agaatgggaa   1140
aaactcatat atgatgcagg ttttagcagc tacaaaatta ccccccatttc tggcttcaag   1200
tcactcatcg aagtttatcc ttgatcctga agttgctgca aagttataaa ttccgaatta    1260
ataagtttcg attcagagag tcaagttaat agtatttatc acttcctgtt acaaattaat    1320
ttcccaaatt tgttcttttc atagagatca ttgttcccta ctgcaaaagt aggtgtttac    1380
atcactactc aagtaaagag gaaaataatg tcatgtttgt ttctgcaaga cagatttatt    1440
tgagatcgta tgaacanatt tatttgagat cgttacag                            1478
```

<210> SEQ ID NO 6
<211> LENGTH: 1260
<212> TYPE: DNA
<213> ORGANISM: Medicago truncatula

<400> SEQUENCE: 6

```
ggcacgagga acaacacaca cataagacat caccaaagct taatctataa acaaatggga      60
tttcaagagc aatggcagtg aagaaactca gctgtatcat gctcaaatcc atttatacaa     120
acatgtatac agctttataa gttccatggc actcaaatct gctgtggaac taggaatagt     180
agatgcaatc cacaaacatg gaaagccat gactgttcct gaattagcct catctttgaa    240
acttcacccct ctaaagtta gtgtcctata taggttcttg cgcttgctaa cacacgatgg    300
tttcttcgca aaaacaacag tgaaagaaga aacagcttat gctctcacac ctccttcaaa   360
gcttctcatc aatggtgaat caacttgttt tgcaccactt gttaagggaa ttcttcatcc    420
atgttctctg gatatgtggc actcctctaa gaaatggttc tcagaggaga aggatcttgc    480
actttatgaa agtgcaatgg gggagacatt ttttaacttt cttaacaaag attctgaatc    540
tgataaactt ggtctgtttc aagggccat ggcagctgat tcacaaatgt ttaagcttgc      600
tctcaaggac tgcagccatg tgtttgaggg tttggaatct ttggttgatg tggcaggtgg    660
gactggagtt gtgtcaaaac tcattcatga agaatttcca cacatcaaat gcacagtttt   720
agatcaacca caggttgtgg ctaacttatc tggaactcaa aatttgaact tgttggtgg    780
```

| | |
|---|---|
| agatatgttc aaatcaatcc ctcctgcaga tgctgtttta ctcaagtggg ttctgcatga | 840 |
| ttgggatgat gaactctccc taaggatatt gaagaactgc aaagaagcta tttcaggaaa | 900 |
| agggaaaaaa ggaaagataa taatcataga cgtatcaatt gatgaaacaa gtgatgatca | 960 |
| tgaattaacc gagttgcaat tgcactttga catggtaatg atgactctgc ataatggaaa | 1020 |
| agaaagagaa aagaaagaat ggaagaaact catctatgac gctggcttca gcagctacaa | 1080 |
| gattactcca atatgtggct tcaagtcact catagaagtt tatccctaat tttaattagt | 1140 |
| agttgttgca ataacttat ttacaaattt aataagtcaa atttgtaatg tttattgttc | 1200 |
| ttctttgcat caaatgttta ttgtttccta tcaaacatga atttcccaag attgcttttt | 1260 |

<210> SEQ ID NO 7
<211> LENGTH: 1242
<212> TYPE: DNA
<213> ORGANISM: Medicago truncatula

<400> SEQUENCE: 7

| | |
|---|---|
| ggcacgaggt agaaacacaa gacatcaccc aagaaaatgg attccagtag caatggcagt | 60 |
| gaagaaagtc agttgtatca tgctcaaatc catctgtaca acatatata cagctttata | 120 |
| aattccatgg cactcaaatc tgctgtggaa ctaggcatag ctgatgcaat ccacaaccat | 180 |
| ggaaaaccaa tgactcttac tgaattagct tcatctttga aactccatcc ttcgaaagtt | 240 |
| agtgtcctgt atcgtctctt gcgcctgcta acacacaatg gtttctttgc aaaaacaaca | 300 |
| ctgatgaatg gcaaagaagg agaagaagaa acaacatatt ctctcactcc tccttcaatg | 360 |
| cttctcataa gtggcaaatc aacatgtttg tcaccatttg ttagcggagt gcttcatcca | 420 |
| tgtcgtctga acgtgtggca ctcctctaag aaatggctca ctgaggacaa ggaactcagc | 480 |
| ctatttgaga gcgcaagagg agagacattt tgggactatc ttaacaaaga tactgaatct | 540 |
| gatgaactga gtatgtttca agaggctatg gctgctgatt ctcaaatctt caaccttgct | 600 |
| ctaaaagagt gcaatcatgt gttgaaggt ttggagtcta tagttgatgt tggaggtgga | 660 |
| agaggaggtt tcacaaaact catccatgaa gcttttcctg acctcaaatg cacagtattt | 720 |
| gatcaaccac aggttgtggc taacttgtct ggagatgaaa atttgaaatt tgttggtgga | 780 |
| gatatgttca aatctatccc tcctgcagat gctgttttac tcaagtggat tttgcatgat | 840 |
| tggaatgatg aattgtcctt aaagatattg gagaattgca aaaaagctat ttcaggaaaa | 900 |
| gggaaaaaag gaaaggtgat aatcattgac atatcaattg acgaaacaag tgacaatcat | 960 |
| gaaacaaatg agttgaaatt ggactttgat ttcatgatga tgactttgtt aaatggaaaa | 1020 |
| gaaagagaga agaagaatg ggagaaactt atactcgacg caggcttcag cagctataag | 1080 |
| attactccta tatgcggctt caagtctatc atcgaagttt atccttaatt ttgattagaa | 1140 |
| cttgttttcac ttaagttatg attaaaattc aataagtttg tactcaaaag tcaaattgat | 1200 |
| agtcacaact gaataatgtt aattaaaaaa aaaaaaaaaa aa | 1242 |

<210> SEQ ID NO 8
<211> LENGTH: 1202
<212> TYPE: DNA
<213> ORGANISM: Medicago sativa

<400> SEQUENCE: 8

| | |
|---|---|
| atggcacgag gggatttcag tagcaatggc agtgaagaaa atcaactgta tcacgctcaa | 60 |
| atccatctgt acaaacatat atacggcttt ataaaattcca tggcactcaa atcagccgtg | 120 |

-continued

```
gaactaggca tagcagatgc aatccaaaac catggaaaac caatgactct tactgaatta      180
gcttcatctt tgaaactcca cccttctaaa gttagtgtcc tttatcgtct cttgcgcttg      240
ctaacacaca atggtttctt tgcgaaaaca acactgatga gtggcaaaga aggagaagaa      300
gaaacaatat attctctcac tcctccttca atgcttctca taagtggcaa atcaacatgt      360
ttgtcaccat ttgttaccgg aacggttcat ccatgtcgtc tgaacatatg gtactcctct      420
acgaaatggc tcactgagga aaggaactc agtctctttg agagcgcaag aggagagaca       480
ttttgggact atcttaacaa agatactgaa tctgatgaac tgagtatgtt tcaagaggct      540
atggctgctg attctcaaat cttcaacctt gctctaaaag agtgcaatca tgtgtttgaa      600
ggtttgaggt ctatagttga tgttggaggt ggaagaggag gtttcacaaa actcatccat      660
gaagcttttc ctgacctcaa atgcacagta tttgatcaac cacaggttgt ggccaattta      720
tctggagatg aaaatttgaa atttgttggt ggagatatgt tcgaatctat cccttctgca      780
gatgctgttt tacttaagtg gattctgcat gattggaatg atgatctctc tttaaagata      840
ttgaagaact gcaaaacagc tatttcagga aaagggaaaa cggaaaaggt gataatcatt      900
gacatatcaa ttgatgaaac aagtgacaat catgaaacaa atgagttgaa attggacttt      960
gacttcatga tgatgacttt gttaaatgga aagaaaagag agaagaaaga atgggagaaa     1020
ctcatattcg acgcaggttt cagcagctat aagattacac ctatatgcgg tttcaagtct     1080
ctcatcgaag tatatccata attttaagtt atgcaactaa ataatttaaa ttaaggcatt     1140
atgtaatcct tcgactcgat atttattgaa aatatgttaa tcgcaaaaaa aaaaaaaaa      1200 aa                                                                    1202
```

<210> SEQ ID NO 9
<211> LENGTH: 357
<212> TYPE: PRT
<213> ORGANISM: Medicago truncatula

<400> SEQUENCE: 9

```
Met Ala Ser Ser Ile Asn Asn Arg Lys Ala Ser Glu Ile Phe Lys Ala
1               5                   10                  15

Gln Ala Leu Leu Tyr Lys Asn Met Tyr Ala Phe Ile Asp Ser Met Ser
            20                  25                  30

Leu Lys Trp Ser Val Glu Met Asp Ile Pro Thr Ile Ile Tyr Asn His
        35                  40                  45

Gly Lys Pro Ile Thr Leu Ser Asn Leu Val Ser Ile Leu Gln Ile Pro
    50                  55                  60

Ser Thr Lys Val Asp Asn Val Gln Arg Leu Met Arg Leu Leu Ala His
65                  70                  75                  80

Asn Gly Phe Phe Glu Ile Val Thr Asn Gln Glu Leu Glu Asn Glu Glu
                85                  90                  95

Glu Ala Tyr Ala Leu Thr Val Thr Ser Glu Leu Leu Val Lys Gly Thr
            100                 105                 110

Glu Leu Cys Leu Ala Pro Met Val Glu Cys Val Leu Asp Pro Lys Phe
        115                 120                 125

Asn Val Ser Phe His Asn Phe Lys Lys Trp Ile Tyr Glu Glu Asp Leu
    130                 135                 140

Thr Leu Phe Ala Thr Ser Leu Gly Cys Asp Leu Trp Glu Phe Leu Asn
145                 150                 155                 160

Lys Asn Pro Glu Tyr Asn Arg Leu Phe Asn Asp Ala Met Ala Ser Asp
                165                 170                 175
```

```
Ser Lys Met Ile Asn Leu Ala Leu Lys Asp Cys Asn Phe Val Phe Glu
            180                 185                 190

Gly Leu Asp Ser Ile Val Asp Val Gly Gly Asn Gly Thr Thr Gly
            195                 200                 205

Lys Ile Ile Cys Glu Thr Tyr Pro Lys Leu Arg Cys Val Val Phe Asp
            210                 215                 220

Arg Pro Lys Val Val Glu Asn Leu Cys Gly Ser Asn Asn Leu Thr Tyr
225                 230                 235                 240

Val Gly Gly Asp Met Phe Ile Ser Val Pro Lys Ala Asp Ala Val Leu
            245                 250                 255

Leu Lys Trp Ile Leu His Asp Trp Thr Asp Arg Asp Cys Ile Lys Ile
            260                 265                 270

Leu Lys Lys Cys Lys Glu Ala Val Thr Thr Glu Gly Lys Arg Gly Lys
            275                 280                 285

Val Ile Val Ile Asp Met Val Ile Asn Glu Lys Lys Glu Glu Asn Glu
            290                 295                 300

Leu Thr Gln Ile Lys Leu Leu Met Asn Val Thr Ile Ser Cys Leu Asn
305                 310                 315                 320

Gly Lys Glu Arg Asn Glu Glu Glu Trp Lys Lys Leu Phe Met Glu Ala
            325                 330                 335

Gly Phe Glu Asn Tyr Lys Ile Ser Pro Cys Thr Gly Leu Leu Ser Leu
            340                 345                 350

Ile Glu Ile Tyr Pro
            355

<210> SEQ ID NO 10
<211> LENGTH: 357
<212> TYPE: PRT
<213> ORGANISM: Medicago truncatula

<400> SEQUENCE: 10

Met Ala Ser Ser Ile Asn Asn Arg Lys Pro Ser Glu Ile Phe Lys Ala
1               5                   10                  15

Gln Ala Leu Leu Tyr Lys Asn Met Tyr Ala Phe Val Asp Ser Met Ser
            20                  25                  30

Leu Lys Trp Ser Ile Glu Met Asn Ile Pro Asn Ile Ile His Asn His
            35                  40                  45

Gly Lys Pro Ile Thr Leu Ser Asn Leu Val Ser Ile Leu Gln Ile Pro
        50                  55                  60

Ser Thr Lys Val Asp Asn Val Gln Arg Leu Met Arg Tyr Leu Ala His
65                  70                  75                  80

Asn Gly Phe Phe Glu Ile Ile Thr Asn Gln Glu Leu Glu Asn Glu Glu
            85                  90                  95

Glu Ala Tyr Ala Leu Thr Val Ala Ser Glu Leu Leu Val Lys Gly Thr
            100                 105                 110

Glu Leu Cys Leu Ala Pro Met Val Glu Cys Val Leu Asp Pro Thr Leu
            115                 120                 125

Ser Thr Ser Phe His Asn Leu Lys Lys Trp Val Tyr Glu Glu Asp Leu
            130                 135                 140

Thr Leu Phe Ala Val Asn Leu Gly Cys Asp Leu Trp Glu Phe Leu Asn
145                 150                 155                 160

Lys Asn Pro Glu Tyr Asn Thr Leu Tyr Asn Asp Ala Leu Ala Ser Asp
            165                 170                 175

Ser Lys Met Ile Asn Leu Ala Met Lys Asp Cys Asn Leu Val Phe Glu
            180                 185                 190
```

Gly Leu Glu Ser Ile Val Asp Val Gly Gly Asn Gly Thr Thr Gly
            195                 200                 205

Lys Ile Ile Cys Glu Thr Phe Pro Lys Leu Thr Cys Val Val Phe Asp
210                 215                 220

Arg Pro Lys Val Val Glu Asn Leu Cys Gly Ser Asn Asn Leu Thr Tyr
225                 230                 235                 240

Val Gly Gly Asp Met Phe Ile Ser Val Pro Lys Ala Asp Ala Val Leu
            245                 250                 255

Leu Lys Ala Val Leu His Asp Trp Thr Asp Lys Asp Cys Ile Lys Ile
            260                 265                 270

Leu Lys Lys Cys Lys Glu Ala Val Thr Ser Asp Gly Lys Arg Gly Lys
            275                 280                 285

Val Ile Val Ile Asp Met Val Ile Asn Glu Lys Lys Asp Glu Asn Gln
            290                 295                 300

Leu Thr Gln Ile Lys Leu Leu Met Asn Val Thr Ile Ser Cys Val Asn
305                 310                 315                 320

Gly Lys Glu Arg Asn Glu Glu Trp Lys Lys Leu Phe Ile Glu Ala
            325                 330                 335

Gly Phe Gln Asp Tyr Lys Ile Ser Pro Phe Thr Gly Leu Met Ser Leu
            340                 345                 350

Ile Glu Ile Tyr Pro
            355

<210> SEQ ID NO 11
<211> LENGTH: 361
<212> TYPE: PRT
<213> ORGANISM: Artificial Sequence
<220> FEATURE:
<223> OTHER INFORMATION: Synthetic Peptide

<400> SEQUENCE: 11

Met Ala Ser Thr Asn Asn Gln Leu Glu Ala Thr Glu Leu Phe Glu Gly
1               5                   10                  15

Gln Ser Leu Leu Tyr Met His Met Phe Gly Phe Leu Lys Ser Met Ala
            20                  25                  30

Leu Lys Trp Ala Ile Gln Leu Asn Ile Pro Asp Ile Tyr Asn His
        35                  40                  45

Gly Lys Pro Ile Thr Leu Ser Asp Leu Val Ser Thr Leu Gln Val Pro
    50                  55                  60

Ile Ser Lys Gln Ser Leu Val Glu Arg Leu Met Arg Phe Leu Ala His
65                  70                  75                  80

Asn Gly Ile Phe Val Ile His Glu Lys Gly Glu Asn Asp Asp Asp
            85                  90                  95

Asp Gln Ala Tyr Ala Leu Thr Pro Ala Ser Lys Leu Leu Ser Lys Ser
            100                 105                 110

Cys Cys Lys Asp His Cys Leu Thr Pro Met Val Leu Met Ser Thr Asp
            115                 120                 125

Pro Ile Leu Met Gly Lys Phe His Gln Leu Gly Asp Trp Ile Cys Gly
            130                 135                 140

Glu Ile Pro Thr Leu Tyr Glu Ala Ala Leu Gly Ser Thr Val Trp Glu
145                 150                 155                 160

Phe Leu Glu Gly Lys Pro Glu Tyr Leu Ser Leu Phe Asn Gln Ala Met
            165                 170                 175

Ala Ser Asp Ser Gln Met Val Asn Leu Ala Leu Lys Asn Cys Ser Lys
            180                 185                 190

```
Val Phe Glu Gly Ile Asp Ser Ile Val Asp Val Gly Gly Thr Gly
            195                 200                 205

Thr Thr Ala Arg Ile Ile Cys Glu Ala Phe Pro Lys Leu Lys Cys Val
210                 215                 220

Val Tyr Asp Leu Pro Gln Val Val Ala Asn Leu Ser Ser Ala Cys Asp
225                 230                 235                 240

Asn Leu Ser Tyr Val Gly Gly Asp Met Phe Lys Ser Ile Pro Gln Ala
            245                 250                 255

Asp Ala Ile Met Leu Lys Trp Ile Leu His Asp Trp Thr Asp Glu Ile
            260                 265                 270

Cys Ile Lys Ile Leu Lys Thr Cys Lys Glu Ser Val Ser Ser Asn Gly
            275                 280                 285

Lys Lys Gly Lys Val Ile Ile Met Asp Ile Ile Ile Asn Glu Glu Asp
            290                 295                 300

Asp Glu Lys Asp Met Thr Glu Thr Lys Leu Cys Leu Asp Leu Ile Met
305                 310                 315                 320

Met Gly Ile Asn Gly Lys Glu Arg Thr Gly Lys Glu Trp Lys His Leu
            325                 330                 335

Phe Val Glu Ala Gly Phe Lys Asp Tyr Lys Ile Phe Pro Leu Phe Glu
            340                 345                 350

Asn Arg Ser Leu Ile Glu Ala Tyr Pro
            355                 360

<210> SEQ ID NO 12
<211> LENGTH: 364
<212> TYPE: PRT
<213> ORGANISM: Artificial Sequence
<220> FEATURE:
<223> OTHER INFORMATION: Synthetic Peptide

<400> SEQUENCE: 12

Met Ala Phe Ser Thr Asn Gly Ser Glu Glu Ser Glu Leu Tyr His Ala
1               5                   10                  15

Gln Ile His Leu Tyr Lys His Val Tyr Asn Phe Val Ser Ser Met Ala
            20                  25                  30

Leu Lys Ser Ala Met Glu Leu Gly Ile Ala Asp Ala Ile His Asn His
        35                  40                  45

Gly Lys Pro Met Thr Leu Ser Glu Leu Ala Ser Leu Lys Leu His
    50                  55                  60

Pro Ser Lys Val Asn Ile Leu His Arg Phe Leu Arg Leu Leu Thr His
65                  70                  75                  80

Asn Gly Phe Phe Ala Lys Thr Ile Val Lys Gly Lys Glu Gly Asp Glu
                85                  90                  95

Glu Glu Glu Ile Ala Tyr Ser Leu Thr Pro Ser Lys Leu Leu Ile
            100                 105                 110

Ser Gly Lys Pro Thr Cys Leu Ser Ser Ile Val Lys Gly Ala Leu His
            115                 120                 125

Pro Ser Ser Leu Asp Met Trp Ser Ser Lys Lys Trp Phe Asn Glu
        130                 135                 140

Asp Lys Glu Gln Thr Leu Phe Glu Cys Ala Thr Gly Glu Ser Phe Trp
145                 150                 155                 160

Asp Phe Leu Asn Lys Asp Ser Glu Ser Ser Thr Leu Ser Met Phe Gln
                165                 170                 175

Asp Ala Met Ala Ser Asp Ser Arg Met Phe Lys Leu Val Leu Gln Glu
            180                 185                 190
```

```
Asn Lys Arg Val Phe Glu Gly Leu Glu Ser Leu Val Asp Val Gly Gly
            195                 200                 205

Gly Thr Gly Gly Val Thr Lys Leu Ile His Glu Ile Phe Pro His Leu
210                 215                 220

Lys Cys Thr Val Phe Asp Gln Pro Gln Val Val Gly Asn Leu Thr Gly
225                 230                 235                 240

Asn Glu Asn Leu Asn Phe Val Gly Gly Asp Met Phe Lys Ser Ile Pro
            245                 250                 255

Ser Ala Asp Ala Val Leu Leu Lys Trp Val Leu His Asp Trp Asn Asp
                260                 265                 270

Glu Gln Ser Leu Lys Ile Leu Lys Asn Ser Lys Glu Ala Ile Ser His
            275                 280                 285

Lys Gly Lys Asp Gly Lys Val Ile Ile Asp Ile Ser Ile Asp Glu
290                 295                 300

Thr Ser Asp Asp Arg Gly Leu Thr Glu Leu Gln Leu Asp Tyr Asp Leu
305                 310                 315                 320

Val Met Leu Thr Met Phe Leu Gly Lys Glu Arg Thr Lys Gln Glu Trp
                325                 330                 335

Glu Lys Leu Ile Tyr Asp Ala Gly Phe Ser Ser Tyr Lys Ile Thr Pro
            340                 345                 350

Ile Ser Gly Phe Lys Ser Leu Ile Glu Val Tyr Pro
            355                 360

<210> SEQ ID NO 13
<211> LENGTH: 357
<212> TYPE: PRT
<213> ORGANISM: Artificial Sequence
<220> FEATURE:
<223> OTHER INFORMATION: Synthetic Peptide

<400> SEQUENCE: 13

Met Asp Phe Lys Ser Asn Gly Ser Glu Glu Thr Gln Leu Tyr His Ala
1               5                   10                  15

Gln Ile His Leu Tyr Lys His Val Tyr Ser Phe Ile Ser Ser Met Ala
            20                  25                  30

Leu Lys Ser Ala Val Glu Leu Gly Ile Val Asp Ala Ile His Lys His
        35                  40                  45

Gly Lys Pro Met Thr Val Pro Glu Leu Ala Ser Leu Lys Leu His
50                  55                  60

Pro Ser Lys Val Ser Val Leu Tyr Arg Phe Leu Arg Leu Leu Thr His
65                  70                  75                  80

Asp Gly Phe Phe Ala Lys Thr Thr Val Lys Glu Glu Thr Ala Tyr Ala
                85                  90                  95

Leu Thr Pro Pro Ser Lys Leu Leu Ile Asn Gly Glu Ser Thr Cys Phe
            100                 105                 110

Ala Pro Leu Val Lys Gly Ile Leu His Pro Cys Ser Leu Asp Met Trp
        115                 120                 125

His Ser Ser Lys Lys Trp Phe Ser Glu Glu Lys Asp Leu Ala Leu Tyr
130                 135                 140

Glu Ser Ala Met Gly Glu Thr Phe Phe Asn Phe Leu Asn Lys Asp Ser
145                 150                 155                 160

Glu Ser Asp Lys Leu Gly Leu Phe Gln Gly Ala Met Ala Ala Asp Ser
                165                 170                 175

Gln Met Phe Lys Leu Ala Leu Lys Asp Cys Ser His Val Phe Glu Gly
            180                 185                 190
```

```
Leu Glu Ser Leu Val Asp Val Ala Gly Gly Thr Gly Val Val Ser Lys
            195                 200                 205

Leu Ile His Glu Glu Phe Pro His Ile Lys Cys Thr Val Leu Asp Gln
        210                 215                 220

Pro Gln Val Val Ala Asn Leu Ser Gly Thr Gln Asn Leu Asn Phe Val
225                 230                 235                 240

Gly Gly Asp Met Phe Lys Ser Ile Pro Pro Ala Asp Ala Val Leu Leu
                245                 250                 255

Lys Trp Val Leu His Asp Trp Asp Glu Leu Ser Leu Arg Ile Leu
            260                 265                 270

Lys Asn Cys Lys Glu Ala Ile Ser Gly Lys Gly Lys Gly Lys Ile
        275                 280                 285

Ile Ile Ile Asp Val Ser Ile Asp Glu Thr Ser Asp Asp His Glu Leu
            290                 295                 300

Thr Glu Leu Gln Leu His Phe Asp Met Val Met Thr Leu His Asn
305                 310                 315                 320

Gly Lys Glu Arg Glu Lys Lys Glu Trp Lys Lys Leu Ile Tyr Asp Ala
                325                 330                 335

Gly Phe Ser Ser Tyr Lys Ile Thr Pro Ile Cys Gly Phe Lys Ser Leu
            340                 345                 350

Ile Glu Val Tyr Pro
        355

<210> SEQ ID NO 14
<211> LENGTH: 363
<212> TYPE: PRT
<213> ORGANISM: Artificial Sequence
<220> FEATURE:
<223> OTHER INFORMATION: Synthethic Peptide

<400> SEQUENCE: 14

Met Asp Ser Ser Ser Asn Gly Ser Glu Glu Ser Gln Leu Tyr His Ala
1               5                   10                  15

Gln Ile His Leu Tyr Lys His Ile Tyr Ser Phe Ile Asn Ser Met Ala
            20                  25                  30

Leu Lys Ser Ala Val Glu Leu Gly Ile Ala Asp Ala Ile His Asn His
        35                  40                  45

Gly Lys Pro Met Thr Leu Thr Glu Leu Ala Ser Ser Leu Lys Leu His
    50                  55                  60

Pro Ser Lys Val Ser Val Leu Tyr Arg Leu Leu Arg Leu Leu Thr His
65                  70                  75                  80

Asn Gly Phe Phe Ala Lys Thr Thr Leu Met Asn Gly Lys Glu Gly Glu
                85                  90                  95

Glu Glu Thr Thr Tyr Ser Leu Thr Pro Pro Ser Met Leu Leu Ile Ser
            100                 105                 110

Gly Lys Ser Thr Cys Leu Ser Pro Phe Val Ser Gly Val Leu His Pro
        115                 120                 125

Cys Arg Leu Asn Val Trp His Ser Ser Lys Lys Trp Leu Thr Glu Asp
    130                 135                 140

Lys Glu Leu Ser Leu Phe Glu Ser Ala Arg Gly Glu Thr Phe Trp Asp
145                 150                 155                 160

Tyr Leu Asn Lys Asp Thr Glu Ser Asp Glu Leu Ser Met Phe Gln Glu
                165                 170                 175

Ala Met Ala Ala Asp Ser Gln Ile Phe Asn Leu Ala Leu Lys Glu Cys
            180                 185                 190
```

Asn His Val Phe Glu Gly Leu Glu Ser Ile Val Asp Val Gly Gly
            195                 200                 205

Arg Gly Gly Phe Thr Lys Leu Ile His Glu Ala Phe Pro Asp Leu Lys
    210                 215                 220

Cys Thr Val Phe Asp Gln Pro Gln Val Val Ala Asn Leu Ser Gly Asp
225                 230                 235                 240

Glu Asn Leu Lys Phe Val Gly Gly Asp Met Phe Lys Ser Ile Pro Pro
                245                 250                 255

Ala Asp Ala Val Leu Leu Lys Trp Ile Leu His Asp Trp Asn Asp Glu
            260                 265                 270

Leu Ser Leu Lys Ile Leu Glu Asn Cys Lys Lys Ala Ile Ser Gly Lys
        275                 280                 285

Gly Lys Lys Gly Lys Val Ile Ile Ile Asp Ile Ser Ile Asp Glu Thr
    290                 295                 300

Ser Asp Asn His Glu Thr Asn Glu Leu Lys Leu Asp Phe Asp Phe Met
305                 310                 315                 320

Met Met Thr Leu Leu Asn Gly Lys Glu Arg Glu Lys Lys Glu Trp Glu
                325                 330                 335

Lys Leu Ile Leu Asp Ala Gly Phe Ser Ser Tyr Lys Ile Thr Pro Ile
            340                 345                 350

Cys Gly Phe Lys Ser Ile Ile Glu Val Tyr Pro
        355                 360

<210> SEQ ID NO 15
<211> LENGTH: 366
<212> TYPE: PRT
<213> ORGANISM: Artificial Sequence
<220> FEATURE:
<223> OTHER INFORMATION: Synthethic Peptide

<400> SEQUENCE: 15

Met Ala Arg Gly Asp Phe Ser Ser Asn Gly Ser Glu Glu Asn Gln Leu
1               5                   10                  15

Tyr His Ala Gln Ile His Leu Tyr Lys His Ile Tyr Gly Phe Ile Asn
            20                  25                  30

Ser Met Ala Leu Lys Ser Ala Val Glu Leu Gly Ile Ala Asp Ala Ile
        35                  40                  45

Gln Asn His Gly Lys Pro Met Thr Leu Thr Glu Leu Ala Ser Ser Leu
    50                  55                  60

Lys Leu His Pro Ser Lys Val Ser Val Leu Tyr Arg Leu Leu Arg Leu
65                  70                  75                  80

Leu Thr His Asn Gly Phe Phe Ala Lys Thr Thr Leu Met Ser Gly Lys
                85                  90                  95

Glu Gly Glu Glu Glu Thr Ile Tyr Ser Leu Thr Pro Pro Ser Met Leu
            100                 105                 110

Leu Ile Ser Gly Lys Ser Thr Cys Leu Ser Pro Phe Val Thr Gly Thr
        115                 120                 125

Val His Pro Cys Arg Leu Asn Ile Trp Tyr Ser Ser Thr Lys Trp Leu
    130                 135                 140

Thr Glu Glu Lys Glu Leu Ser Leu Phe Glu Ser Ala Arg Gly Glu Thr
145                 150                 155                 160

Phe Trp Asp Tyr Leu Asn Lys Asp Thr Glu Ser Asp Glu Leu Ser Met
                165                 170                 175

Phe Gln Glu Ala Met Ala Ala Asp Ser Gln Ile Phe Asn Leu Ala Leu
            180                 185                 190

Lys Glu Cys Asn His Val Phe Glu Gly Leu Arg Ser Ile Val Asp Val
            195                 200                 205

Gly Gly Gly Arg Gly Gly Phe Thr Lys Leu Ile His Glu Ala Phe Pro
210                 215                 220

Asp Leu Lys Cys Thr Val Phe Asp Gln Pro Gln Val Val Ala Asn Leu
225                 230                 235                 240

Ser Gly Asp Glu Asn Leu Lys Phe Val Gly Gly Asp Met Phe Glu Ser
            245                 250                 255

Ile Pro Ser Ala Asp Ala Val Leu Leu Lys Trp Ile Leu His Asp Trp
            260                 265                 270

Asn Asp Asp Leu Ser Leu Lys Ile Leu Lys Asn Cys Lys Thr Ala Ile
            275                 280                 285

Ser Gly Lys Gly Lys Thr Gly Lys Val Ile Ile Asp Ile Ser Ile
            290                 295                 300

Asp Glu Thr Ser Asp Asn His Glu Thr Asn Glu Leu Lys Leu Asp Phe
305                 310                 315                 320

Asp Phe Met Met Met Thr Leu Leu Asn Gly Lys Glu Arg Glu Lys Lys
                325                 330                 335

Glu Trp Glu Lys Leu Ile Phe Asp Ala Gly Phe Ser Ser Tyr Lys Ile
            340                 345                 350

Thr Pro Ile Cys Gly Phe Lys Ser Leu Ile Glu Val Tyr Pro
            355                 360                 365

<210> SEQ ID NO 16
<211> LENGTH: 21
<212> TYPE: DNA
<213> ORGANISM: Artificial Sequence
<220> FEATURE:
<223> OTHER INFORMATION: Synthetic Primer

<400> SEQUENCE: 16
cttcttctcc ttctttgcca t                                         21

<210> SEQ ID NO 17
<211> LENGTH: 23
<212> TYPE: DNA
<213> ORGANISM: Artificial Sequence
<220> FEATURE:
<223> OTHER INFORMATION: Synthetic Primer

<400> SEQUENCE: 17
agaaacacaa gacatcaccc aag                                       23

<210> SEQ ID NO 18
<211> LENGTH: 21
<212> TYPE: DNA
<213> ORGANISM: Artificial Sequence
<220> FEATURE:
<223> OTHER INFORMATION: Synthetic Primer

<400> SEQUENCE: 18
acacaactcc agtcccacct g                                         21

<210> SEQ ID NO 19
<211> LENGTH: 23
<212> TYPE: DNA
<213> ORGANISM: Artificial Sequence
<220> FEATURE:
<223> OTHER INFORMATION: Synthetic Primer

<400> SEQUENCE: 19

```
acatggaaag cctatgactg ttc                                        23

<210> SEQ ID NO 20
<211> LENGTH: 20
<212> TYPE: DNA
<213> ORGANISM: Artificial Sequence
<220> FEATURE:
<223> OTHER INFORMATION: Synthetic Primer

<400> SEQUENCE: 20
aactttgcag caacttcagg                                            20

<210> SEQ ID NO 21
<211> LENGTH: 27
<212> TYPE: DNA
<213> ORGANISM: Artificial Sequence
<220> FEATURE:
<223> OTHER INFORMATION: Synthetic Primer

<400> SEQUENCE: 21
acaatagtga aaggcaaaga aggagat                                    27

<210> SEQ ID NO 22
<211> LENGTH: 22
<212> TYPE: DNA
<213> ORGANISM: Artificial Sequence
<220> FEATURE:
<223> OTHER INFORMATION: Synthetic Primer

<400> SEQUENCE: 22
atacgaccgt atcaatatgc ct                                         22

<210> SEQ ID NO 23
<211> LENGTH: 26
<212> TYPE: DNA
<213> ORGANISM: Artificial Sequence
<220> FEATURE:
<223> OTHER INFORMATION: Synthetic Primer

<400> SEQUENCE: 23
ttaacaccaa tggttcttat gtctac                                     26

<210> SEQ ID NO 24
<211> LENGTH: 19
<212> TYPE: DNA
<213> ORGANISM: Artificial Sequence
<220> FEATURE:
<223> OTHER INFORMATION: Synthetic Primer

<400> SEQUENCE: 24
tccaatcatg caaaaccgc                                             19

<210> SEQ ID NO 25
<211> LENGTH: 23
<212> TYPE: DNA
<213> ORGANISM: Artificial Sequence
<220> FEATURE:
<223> OTHER INFORMATION: Synthetic Primer

<400> SEQUENCE: 25
gttcttgatc caacactttc aac                                        23

<210> SEQ ID NO 26
<211> LENGTH: 24
<212> TYPE: DNA
```

```
<213> ORGANISM: Artificial Sequence
<220> FEATURE:
<223> OTHER INFORMATION: Synthetic Primer

<400> SEQUENCE: 26
ggatcaaaca gaaccaaaca ttac                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic Primer

<400> SEQUENCE: 27
ggatcaaaca gaaccaaaca ttac                                          24

<210> SEQ ID NO 28
<211> LENGTH: 24
<212> TYPE: DNA
<213> ORGANISM: Artificial Sequence
<220> FEATURE:
<223> OTHER INFORMATION: Synthetic Primer

<400> SEQUENCE: 28
gaatgcatga tggatcaata caaa                                          24

<210> SEQ ID NO 29
<211> LENGTH: 20
<212> TYPE: DNA
<213> ORGANISM: Artificial Sequence
<220> FEATURE:
<223> OTHER INFORMATION: Synthetic Primer

<400> SEQUENCE: 29
cgggttcgta tcatgagctg                                               20

<210> SEQ ID NO 30
<211> LENGTH: 40
<212> TYPE: PRT
<213> ORGANISM: Medicago truncatula

<400> SEQUENCE: 30

Thr Tyr Val Gly Gly Asp Met Phe Thr Ser Ile Pro Asn Ala Asp Ala
1               5                   10                  15

Val Leu Leu Lys Tyr Ile Leu His Asn Trp Thr Asp Lys Asp Cys Thr
            20                  25                  30

Arg Ile Leu Lys Lys Cys Lys Glu
        35                  40

<210> SEQ ID NO 31
<211> LENGTH: 40
<212> TYPE: PRT
<213> ORGANISM: Medicago truncatula

<400> SEQUENCE: 31

Asn Phe Val Gly Gly Asp Met Phe Lys Ser Val Pro Ser Ala Asp Ala
1               5                   10                  15

Val Leu Leu Lys Trp Val Leu His Asp Trp Asn Asp Glu Leu Cys Leu
            20                  25                  30

Lys Ile Leu Lys Asn Cys Lys Glu
        35                  40
```

-continued

```
<210> SEQ ID NO 32
<211> LENGTH: 40
<212> TYPE: PRT
<213> ORGANISM: Medicago truncatula

<400> SEQUENCE: 32

Thr Tyr Val Gly Gly Asp Met Phe Ile Ser Val Pro Lys Ala Asp Ala
1               5                   10                  15

Val Leu Leu Lys Ala Val Leu His Asp Trp Thr Asp Lys Asp Cys Ile
            20                  25                  30

Lys Ile Leu Lys Lys Cys Lys Glu
            35                  40
```